(12) United States Patent
Itotani et al.

(10) Patent No.: US 11,992,942 B2
(45) Date of Patent: May 28, 2024

(54) CONTROL APPARATUS, CONTROL METHOD, AND MASTER-SLAVE SYSTEM

(71) Applicant: Sony Corporation, Tokyo (JP)

(72) Inventors: Yuki Itotani, Tokyo (JP); Hiromasa Masuda, Tokyo (JP); Atsushi Miyamoto, Kanagawa (JP); Kazuhito Wakana, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 919 days.

(21) Appl. No.: 16/980,858

(22) PCT Filed: Mar. 4, 2019

(86) PCT No.: PCT/JP2019/008433
§ 371 (c)(1),
(2) Date: Sep. 15, 2020

(87) PCT Pub. No.: WO2019/188022
PCT Pub. Date: Oct. 3, 2019

(65) Prior Publication Data
US 2021/0008709 A1  Jan. 14, 2021

(30) Foreign Application Priority Data

Mar. 28, 2018 (JP) ................................ 2018-061789
Jan. 21, 2019 (JP) ................................ 2019-007798

(51) Int. Cl.
*B25J 3/00* (2006.01)
*A61B 1/00* (2006.01)
(Continued)

(52) U.S. Cl.
CPC ............. *B25J 3/00* (2013.01); *A61B 1/00188* (2013.01); *A61B 34/37* (2016.02); *H04N 23/69* (2023.01);
(Continued)

(58) Field of Classification Search
None
See application file for complete search history.

(56) References Cited

U.S. PATENT DOCUMENTS

| 4,661,032 A | 4/1987 | Arai |
| 2003/0023346 A1 | 1/2003 | Salisbury, Jr. et al. |

(Continued)

FOREIGN PATENT DOCUMENTS

| JP | 04-101787 A | 4/1992 |
| JP | 08-187246 A | 7/1996 |

(Continued)

OTHER PUBLICATIONS

International Search Report and Written Opinion dated May 28, 2019 for PCT/JP2019/008433 filed on Mar. 4, 2019, 24 pages including English Translation of the International Search Report and Written Opinion.

*Primary Examiner* — Jaime Figueroa
*Assistant Examiner* — Arslan Azhar
(74) *Attorney, Agent, or Firm* — XSENSUS LLP

(57) ABSTRACT

[Problem to be Solved] There are provided a control apparatus, a control method, and a master-slave system.

[Solution] A control apparatus includes: a detector that detects whether or not a master apparatus used for an operation of a slave apparatus is located at a movable range limit; and a controller that controls, on the basis of a detection result, a slave parameter related to control of the slave apparatus and an image parameter related to an image displayed on the basis of imaging.

17 Claims, 25 Drawing Sheets

(51) Int. Cl.
  *A61B 34/30* (2016.01)
  *A61B 34/37* (2016.01)
  *H04N 23/50* (2023.01)
  *H04N 23/69* (2023.01)

(52) U.S. Cl.
  CPC ...... *A61B 2034/301* (2016.02); *H04N 23/555* (2023.01)

(56) References Cited

U.S. PATENT DOCUMENTS

| | | | | |
|---|---|---|---|---|
| 2010/0161129 | A1* | 6/2010 | Costa | B25J 9/1697 |
| | | | | 901/47 |
| 2017/0112368 | A1* | 4/2017 | Stern | A61B 34/37 |
| 2017/0172675 | A1* | 6/2017 | Jarc | A61B 90/361 |
| 2017/0245954 | A1* | 8/2017 | Beira | A61B 34/37 |
| 2018/0025666 | A1* | 1/2018 | Ho | G09B 9/00 |
| | | | | 434/262 |

FOREIGN PATENT DOCUMENTS

| | | |
|---|---|---|
| JP | 08-215211 A | 8/1996 |
| JP | 2001-150368 A | 6/2001 |
| JP | 2001-334481 A | 12/2001 |
| JP | 2016-068237 A | 5/2016 |
| WO | 2015/146850 A1 | 10/2015 |

\* cited by examiner

FIG. 17
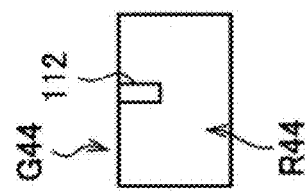
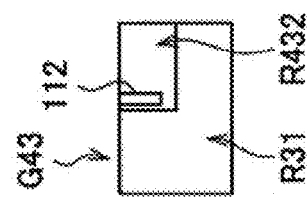
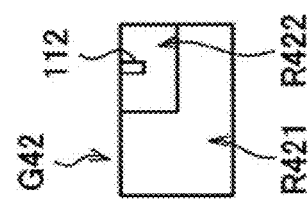
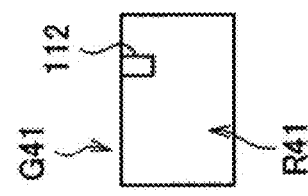

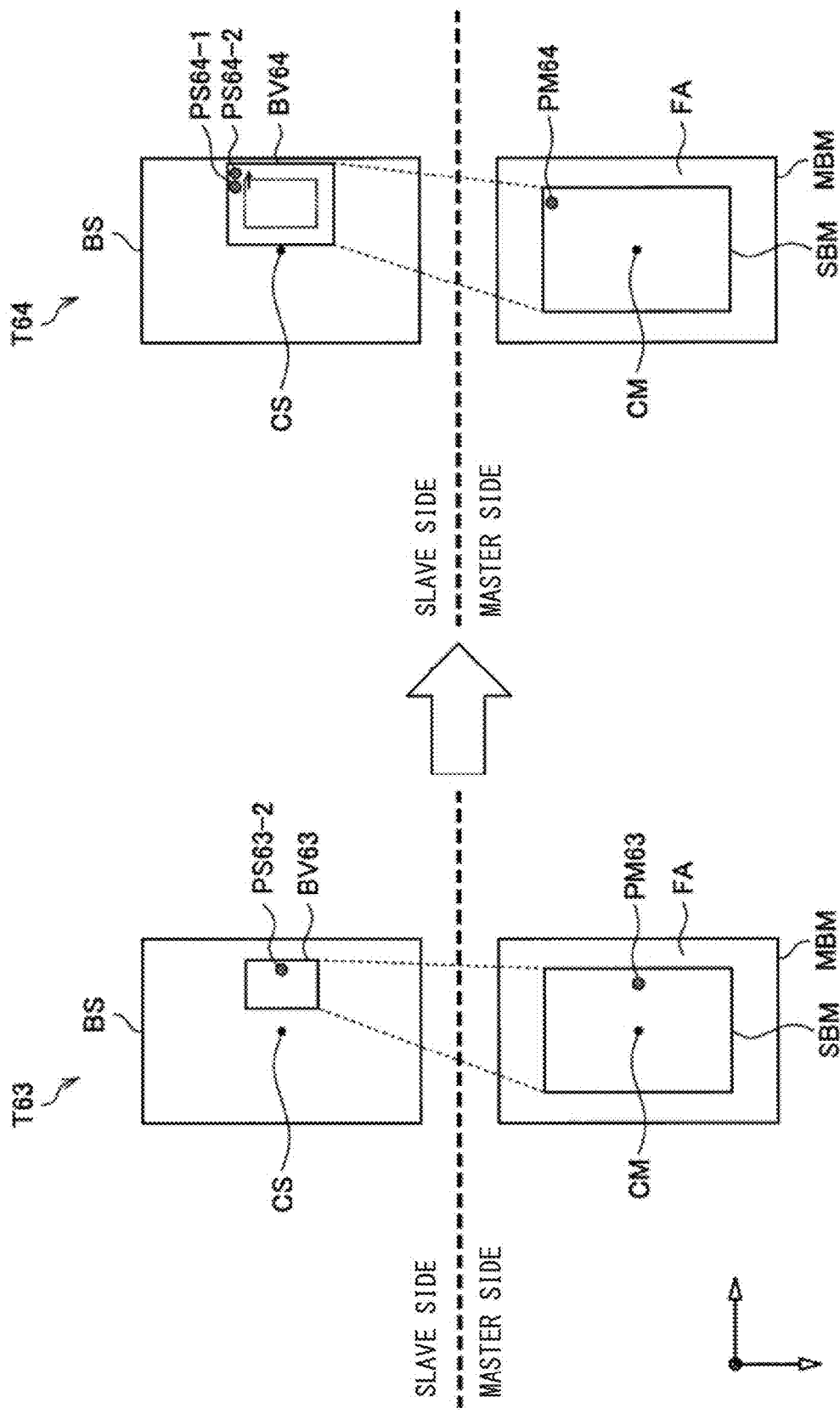

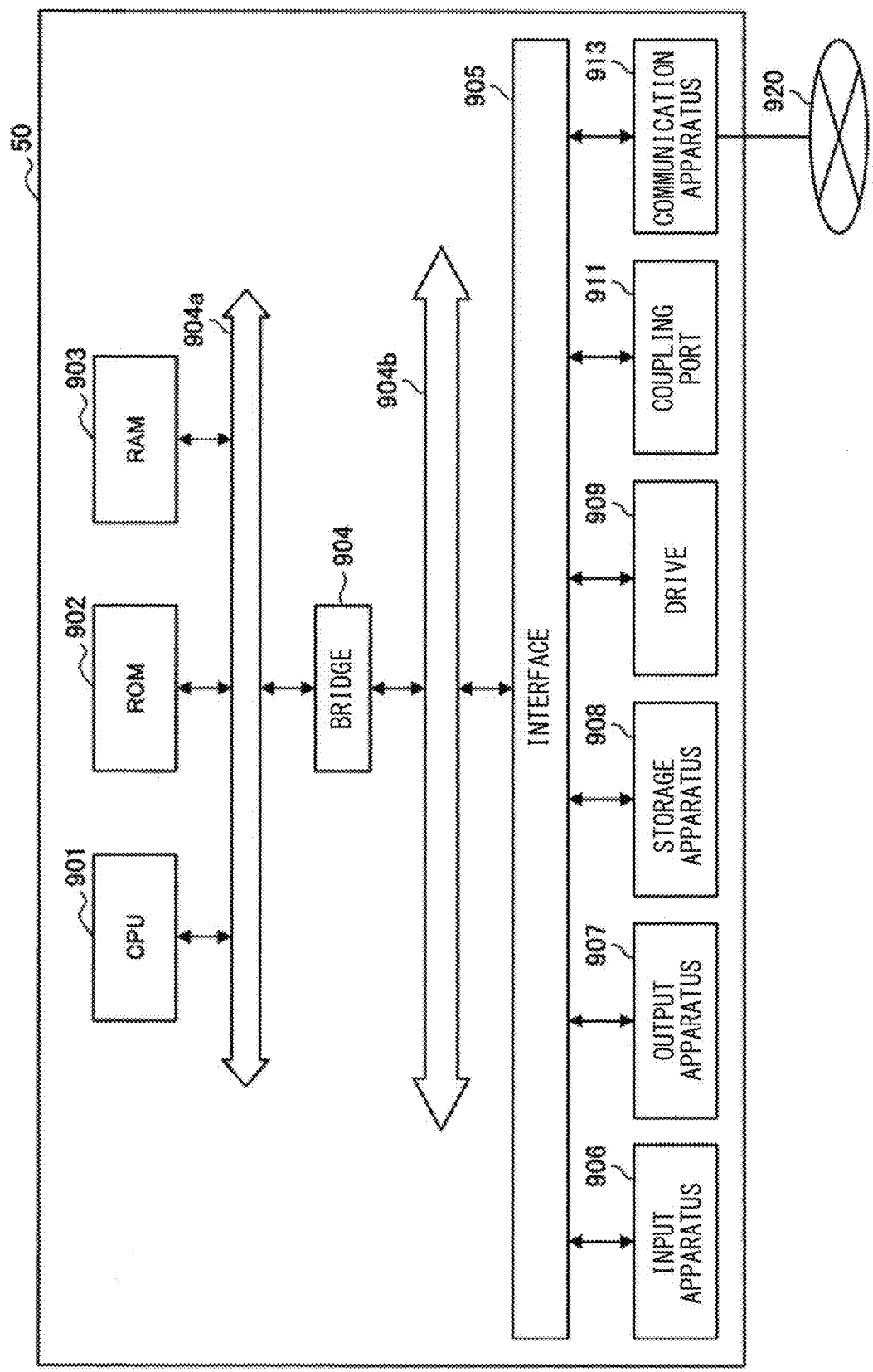

CONTROL APPARATUS, CONTROL METHOD, AND MASTER-SLAVE SYSTEM

CROSS-REFERENCE TO RELATED APPLICATIONS

The present application is based on PCT filing PCT/JP2019/008433, filed Mar. 4, 2019, which claims priority to JP 2018-061789, filed Mar. 28, 2018, and JP 2019-007798, filed Jan. 21, 2019, the entire contents of each are incorporated herein by reference.

TECHNICAL FIELD

The present disclosure relates to a control apparatus, a control method, and a master-slave system.

BACKGROUND ART

In recent years, as an operation system used in a case where endoscopic surgery is carried out, a master-slave mode system (hereinafter, also referred to as "master-slave system") has been known that make it possible to approach an affected site without making a large incision on the body of a patient. In such a master-slave system, a surgeon (a user) such as a doctor operates a master apparatus including an input interface, and a slave apparatus including a medical instrument such as forceps or tweezers is remotely controlled in accordance with an operation of the master apparatus by the surgeon. The slave apparatus is configured, for example, as an arm apparatus with a surgical instrument held at a front end, and is able to change the position or attitude of the surgical instrument in an abdomen.

A master-slave system as described above uses a display apparatus that displays an image of an affected site acquired by an endoscope or the like, and a surgeon conducts a procedure by operating while looking at the image displayed on the display apparatus (for example, see the following PTL 1).

CITATION LIST

Patent Literature

PTL 1: Japanese Unexamined Patent Application Publication No. 2013-17513

SUMMARY OF THE INVENTION

Problems to be Solved by the Invention

In a master-slave system as described above, a mechanism is desired to further reduce a burden on a user.

Means for Solving the Problems

According to the present disclosure, there is provided a control apparatus including: a detector that detects whether or not a master apparatus used for an operation of a slave apparatus is located at a movable range limit; and a controller that controls, on the basis of a detection result, a slave parameter related to control of the slave apparatus and an image parameter related to an image displayed on the basis of imaging.

In addition, according to the present disclosure, there is provided a control method including: detecting whether or not a master apparatus used for an operation of a slave apparatus is located at a movable range limit, and controlling, on the basis of a detection result, a slave parameter related to control of the slave apparatus and an image parameter related to an image displayed on the basis of imaging.

In addition, according to the present disclosure, there is provided a master-slave system including: a slave apparatus; a master apparatus used for an operation of the slave apparatus; and a control apparatus including a detector and a controller, the detector that detects whether or not the master apparatus is located at a movable range limit, and the controller that controls, on the basis of a detection result, a slave parameter related to control of the slave apparatus and an image parameter related to an image displayed on the basis of imaging.

Effects of the Invention

As described above, according to the present disclosure, it is possible to further reduce a burden on a user who operates the master-slave system.

It is to be noted that the effects described above are not necessarily limitative. Any of the effects indicated in this description or other effects that may be understood from this description may be exerted in addition to the effects described above or in place of the effects described above.

BRIEF DESCRIPTION OF DRAWINGS

FIG. 17 is an explanatory diagram for describing the modification example 1.

FIG. 27 is an explanatory diagram for describing the modification example 5.

FIG. 28 is an explanatory diagram illustrating a hardware configuration example.

MODES FOR CARRYING OUT THE INVENTION

Figure 1:
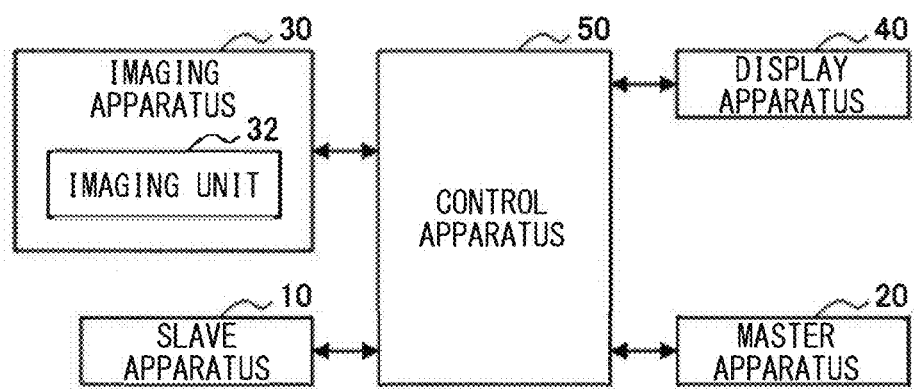
FIG. 1 is a schematic configuration diagram of a master-slave system 1000 according to a first embodiment of the present disclosure.

The following describes a preferred embodiment of the present disclosure in detail with reference to the accompanying drawings. It is to be noted that, in this description and the accompanying drawings, components that have substantially the same functional configuration are denoted by the same reference numerals, and thus redundant description thereof is omitted.

In addition, in this description and the accompanying drawings, there are cases in which a plurality of components having substantially the same functional configuration are distinguished by adding different alphabets after the same reference numeral. However, in a case where it is not necessary to particularly distinguish a plurality of components having substantially the same functional configuration, only the same reference numeral is attached.

It is to be noted that description is given in the following order.

<<1. Background>>
<<2. First Embodiment>>
<<3. Second Embodiment>>
<<4. Modification Examples>>
<<5. Hardware Configuration Example>>
<<6. Conclusion>>

1. Background

A background to creation of an embodiment of the present disclosure is first described before describing the embodiment of the present disclosure.

In recent years, a master-slave system that is a master-slave mode operation system has been used in endoscopic surgery and the like. The master-slave system includes a master apparatus and a slave apparatus. The master apparatus is an apparatus used to operate the slave apparatus, and includes an input interface to be operated by a surgeon such as a doctor (hereinafter also referred to as "user"). In addition, the slave apparatus includes a medical instrument such as forceps or tweezers, and is remotely operated in accordance with an operation of the master apparatus by the user.

In the master-slave system, a movement amount inputted in the master apparatus (hereinafter simply referred to as "movement amount for the master apparatus") and a movement amount of a medical instrument or the like in the slave apparatus (hereinafter simply referred to as "movement amount for the slave apparatus") may be controlled to correspond to each other. For example, the slave apparatus is controlled in accordance with the movement amount for the master apparatus to cause a ratio of the movement amount for the slave apparatus to the movement amount of the master apparatus to be constant. In this description, a ratio of the movement amount for the master apparatus to the movement amount for the corresponding slave apparatus is referred to as "operation magnification".

In addition, each of the master apparatus and the slave apparatus has an origin point, and an offset distance from a point in the slave apparatus corresponding to the origin point in the master apparatus to the origin point in the slave apparatus is referred to as "operation offset" in this description. A movable range of an input interface included in the master apparatus (hereinafter also simply referred to as "movable range of the master apparatus") and a region where the medical instrument or the like of the slave apparatus is movable by an operation on the master apparatus (hereinafter also simply referred to as "operation region") may correspond to each other on the basis of the operation magnification and the operation offset. Accordingly, the operation region becomes smaller with an increase in the operation magnification, and the operation region is moved in accordance with an offset.

It is to be noted that in this description, parameters related to control of the slave apparatus such as the operation magnification and the operation offset are collectively referred to as "slave parameter". It is to be noted that the slave parameter may include parameters related to control of the slave apparatus other than the operation magnification and the operation offset.

In the master-slave system, the operation magnification may be dynamically settable. For example, setting the operation magnification to be large makes it possible to perform work on a magnified fine region. However, the movable range of the master apparatus is fixed irrespective of the operation magnification; therefore, setting the operation magnification to be large may cause a possibility that the operation region becomes smaller and large movement becomes difficult. In addition, in a case where the operation magnification is set to be large, to perform a large and fast action in the slave apparatus, it is necessary to perform a larger and faster action in the master apparatus, and such an action my become difficult.

Accordingly, in the slave apparatus, to simultaneously perform an extremely fine action and a large action that needs rapidity, for example, it is desirable that the operation magnification be seamlessly changeable. However, to change the operation magnification in an existing master-slave system, it is necessary to suspend remote control of the slave apparatus or it is necessary to use an input device other than the master apparatus such as a foot pedal, which results in a large burden on the user.

In addition, to move the operation region without changing the operation magnification, it is desirable to change the operation offset. For example, to further move a medical instrument included in the slave apparatus in the same direction without changing the operation magnification irrespective of having reached a movable range limit of the master apparatus, it is desirable to change the operation offset. The movable range limit is a position where a master position is not allowed to be moved in a specific direction or a position close to such a position. It is to be noted that although the movable range limit of the master apparatus is described later, the movable range limit of the master apparatus may be a movable range limit of an input interface included in the master apparatus, for example.

In the existing master-slave system, also to change the operation offset, it is necessary to suspend the remote control of the slave apparatus and it is necessary to use an input device other than the master apparatus, which causes a factor in an increase in a burden on the user.

In addition, the master-slave system as described above uses a display apparatus that displays an image of an affected site acquired on the basis of imaging by an endoscope or the like, and a surgeon operates the master apparatus while looking at the image displayed on the display apparatus. Accordingly, even if it is possible to change the operation magnification or the operation offset as described above without imposing a burden on the user, to allow the user to comfortably perform an operation, it is desirable to change a magnification of the image displayed on the display apparatus (hereinafter also referred to as "image magnification") or an offset of the image (hereinafter also referred to as "image offset").

It is to be noted that in this description, parameters related to an image displayed on the basis of imaging such as the image magnification and the image offset are collectively referred to as "image parameter". It is to be noted that the image parameter may include parameters related to the image displayed on the basis of imaging other than the image magnification and the image offset.

In the existing master-slave system, also to change such an image parameter, an explicit and intentional operation by the user is necessary. Further, also to change such an image parameter, it is necessary to suspend remote control of the slave apparatus and it is necessary to use an input device other than the master apparatus, which cause a factor in an increase in a burden on the user.

Accordingly, respective embodiments of the present disclosure have been created with circumstances described above as a single viewpoint. In a master-slave system according to each of the embodiments described below, whether or not the master apparatus has reached the movable range limit is detected, and the operation magnification or the operation offset is controlled on the basis of a detection result. Such a configuration makes it possible to appropriately change the operation magnification or the operation offset without suspending remote control of the slave apparatus and without using an input device other than the master apparatus, and makes it possible to reduce a burden on the user. In addition, in the master-slave system according to each of the embodiments described below, the image magnification or the image offset is also controlled on the basis of a detection result of whether or not the master apparatus is located at the movable range limit. Such a configuration makes it possible to change the image magnification or the image offset automatically in accordance with change in the operation magnification or the operation offset, and makes it possible to further reduce the burden on the user. The respective embodiments of the present disclosure having such effects are successively described in detail below. It is to be noted that in the master-slave system according to each of the embodiments described below, whether or not the master position of the master apparatus has reached the movable range limit is detected.

2. First Embodiment

2-1. System Configuration

FIG. 1 is a schematic configuration diagram of a master-slave system 1000 according to a first embodiment of the present disclosure. As illustrated in FIG. 1, the master-slave system 1000 is a master-slave mode operation system including a slave apparatus 10, a master apparatus 20, an imaging apparatus 30, a display apparatus 40, and a control apparatus 50.

The slave apparatus 10 is a slave-side apparatus in the master-slave system 1000. The slave apparatus 10 may be a robot (a robot having a link mechanism including an active joint) for moving in association with an input operation to the master apparatus 20, for example. The slave apparatus 10 includes one or two or more active joints and a link coupled to the active joints. In addition, the slave apparatus 10 includes, for example, driving mechanisms for driving the active joints at respective positions corresponding to the active joints. Examples of the driving mechanisms described above include a motor and a driver. The driving mechanisms may be controlled by the control apparatus 50 to be described later.

Figure 2:
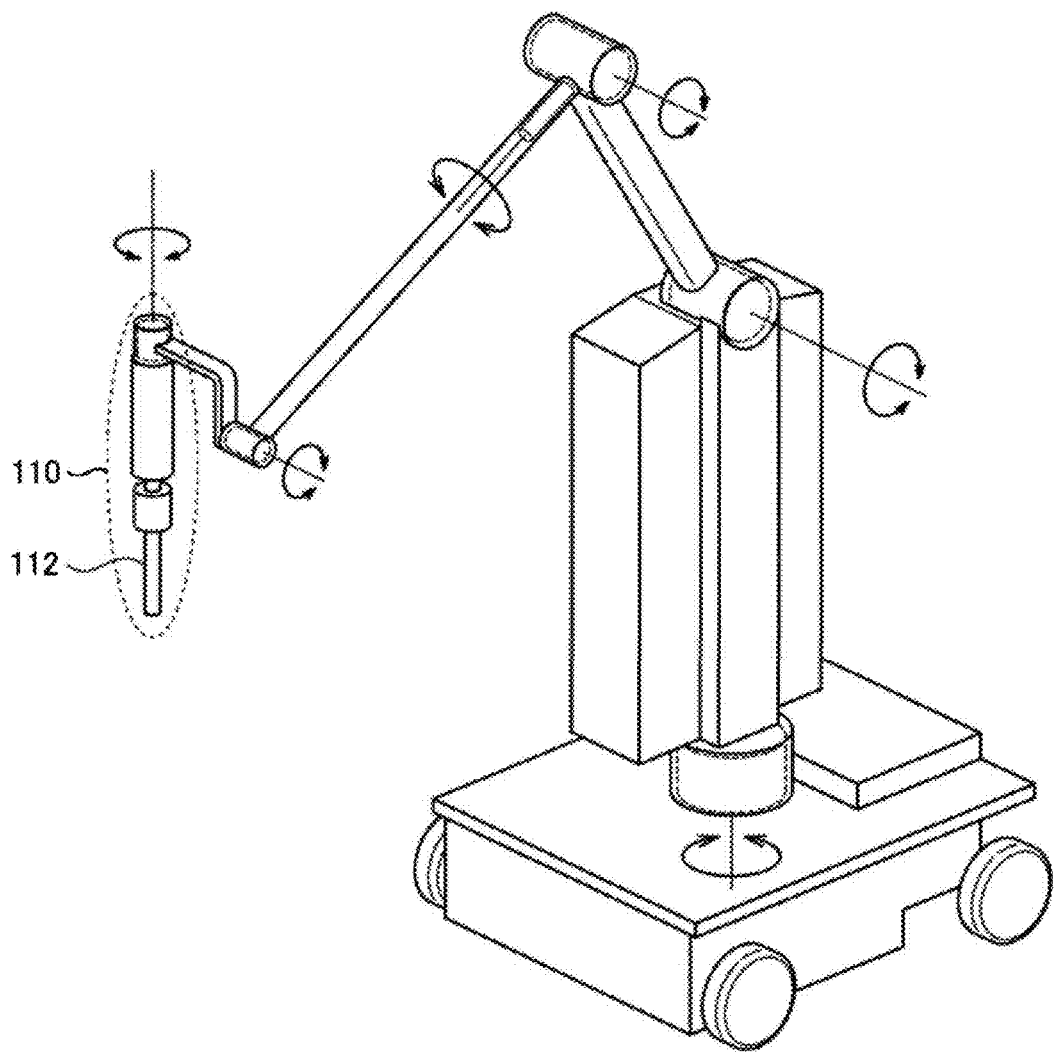
FIG. 2 illustrates an example of a slave apparatus 10 according to the same embodiment.

FIG. 2 illustrates an diagram illustrating an example of the slave apparatus 10 according to the present embodiment. In the example illustrated in FIG. 2, a front end section 110 is a front end portion of an arm of the slave apparatus 10, and includes a contact section 112 where a surgical instrument comes into contact with a patient. A user operates the master apparatus 20 to remotely control the position of the contact section 112. Hereinafter, the position of the contact section 112 included in the slave apparatus 10 is also simply referred to as "slave position". In addition, in the present embodiment, an operation region of the slave apparatus 10 described above may correspond to a region where the contact section 112 is movable by an operation on the master apparatus, for example.

It is to be noted that the example illustrated in FIG. 2 is only one example, and the configuration of the slave apparatus 10 according to the present embodiment is not limited to the example illustrated in FIG. 2.

Figure 3:
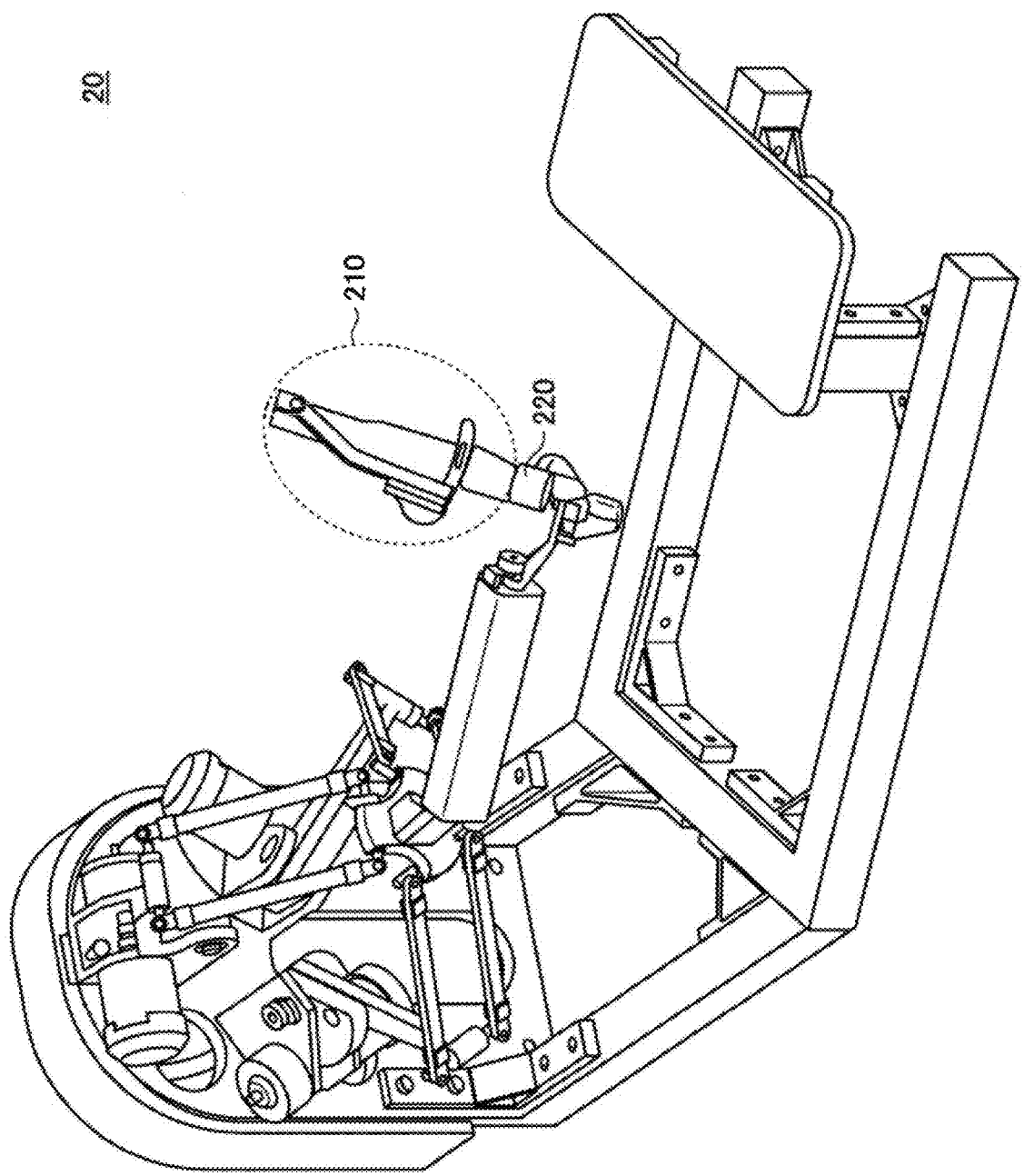
FIG. 3 illustrates an example of a master apparatus 20 according to the same embodiment.

The master apparatus 20 is a master-side apparatus in the master-slave system 1000. The master apparatus 20 may be a robot (a robot having a link mechanism including a passive joint) including one or two or more joints including a passive joint and a link coupled to the joints, for example. FIG. 3 illustrates an example of the master apparatus 20 according to the present embodiment.

In the example illustrated in FIG. 3, the master apparatus 20 includes an operation body 210 and a force sensor 220. The operation body 210 is provided to a link coupled to a passive joint. The force sensor 220 measures force applied to the operation body 210. Here, examples of the force sensor 220 according to the present embodiment include any sensor that is able to measure force applied to the operation body 210, such as a "force sensation sensor having any system such as a system using a strain gauge" or a "tactile sensor having any system such as a system in which a tactile sensation is obtained by measuring vibration using a piezoelectric element, a microphone, and the like". In addition, the master apparatus 20 includes, for example, motion sensors for measuring motions of the joints at the respective positions corresponding to the joints.

In the present embodiment, the operation body 210 is an input interface of the master apparatus 20, and the user is able to move (remotely control) the position of the contact section 112 described above by an operation of moving the position of the operation body 210. Hereinafter, the position of the operation body 210 included in the master apparatus 20 is also simply referred to as "master position". In addition, in the present embodiment, a movable range of the master apparatus 20 means a movable range of the operation body 210, and a movable range limit of the master apparatus 20 means a movable range limit of the operation body 210.

It is to be noted that FIG. 3 illustrates an example in which the operation body 210 provided to the master apparatus 20 is a stylus-shaped operation device, but the operation body 210 according to the present embodiment is not limited to the example illustrated in FIG. 3. Examples of the operation body 210 according to the present embodiment include an operation device having any shape such as a glove-shaped operation device. In addition, the operation body 210 according to the present embodiment may be any operation device that is applicable to a haptic device. In addition, the master apparatus 20 may have a configuration in which the operation body 210 is replaceable. It is to be noted that the configuration of the master apparatus 20 according to the present embodiment is not limited to the example illustrated in FIG. 3, and may have any configuration.

The imaging apparatus 30 includes an imaging unit 32 that acquires an image of an affected site by imaging. The imaging unit 32 may include an endoscope and the like, for example. In addition, the imaging unit 32 may include a stereo camera.

The imaging apparatus 30 according to the present embodiment has a zoom mechanism, and may make a zoom magnification (an imaging magnification) of the imaging unit 32 changeable. In addition, the imaging apparatus 30 includes, for example, a robot arm that grasps the imaging unit 32, and the position and the attitude of the imaging unit 32 may be changeable. The zoom magnification of the imaging unit 32, and the position and the attitude of the imaging unit 32 may be controlled by the control apparatus 50 to be described later.

The display apparatus 40 displays an image outputted from the control apparatus 50 to be described later. The display apparatus 40 may be an installation type display or a HMD (Head Mounted Display) mounted on a head of the user.

The control apparatus 50 is an apparatus that controls each of other apparatuses included in the master-slave system 1000. The control apparatus 50 is coupled to each of other apparatuses included in the master-slave system 1000 in any communication scheme. For example, the control apparatus 50 receives, from the master apparatus 20, information measured by a sensor included in the master apparatus 20, and acquires the master position (the position of the operation body 210 included in the master apparatus 20) on the basis of the received information. The control apparatus 50 then controls the slave position (the contact section 112 included in the slave apparatus 10) on the basis of the acquired master position, and the operation magnification and the operation offset described above.

In addition, the control apparatus 50 according to the present embodiment detects whether or not the master apparatus 20 has reached the movable range limit, and controls the slave parameter and the image parameter on the basis of a detection result. It is to be noted that, as described above, the slave parameter is a parameter related to control of the slave apparatus 10, and includes the operation magnification and the operation offset. In addition, the image parameter is a parameter related to an image displayed on the display apparatus 40 on the basis of imaging by the imaging apparatus 30, and includes the image magnification and the image offset. It is to be noted that in the present embodiment, the image magnification means a zoom magnification of the imaging apparatus 30, and control of the image offset may be performed by control for moving the position of the imaging unit 32 included in the imaging apparatus 30.

With such a configuration, the slave parameter and the image parameter are controlled without suspending remote control of the slave apparatus 10 and without necessity of an operation using an input device other than the master apparatus 20, thereby reducing a burden on the user. The following describes control of the slave parameter and the image parameter on the basis of a detection result of whether or not such a master apparatus has reached the movable range limit.

2-2. Control on Basis of Detection Result of Whether or Not Movable Range Limit Has Been Reached In a case where it is detected that the master apparatus 20 has reached the movable range limit, the control apparatus 50 according to the present embodiment performs at least one of decrease control of the operation magnification and the image magnification (hereinafter also simply referred to as "decrease control") or control of the operation offset and the image offset (hereinafter also simply referred to as "offset control"). Whether the control apparatus 50 performs the decrease control or the offset control may be switched in accordance with an operation on the master apparatus 20 by the user, for example, and an operation for such switching is described later.

In the following, the decrease control by the control apparatus 50 according to the present embodiment is described with reference to FIGS. 4 to 6, and then the offset control by the control apparatus 50 according to the present embodiment is described with reference to FIGS. 7 to 9.

Figure 4:
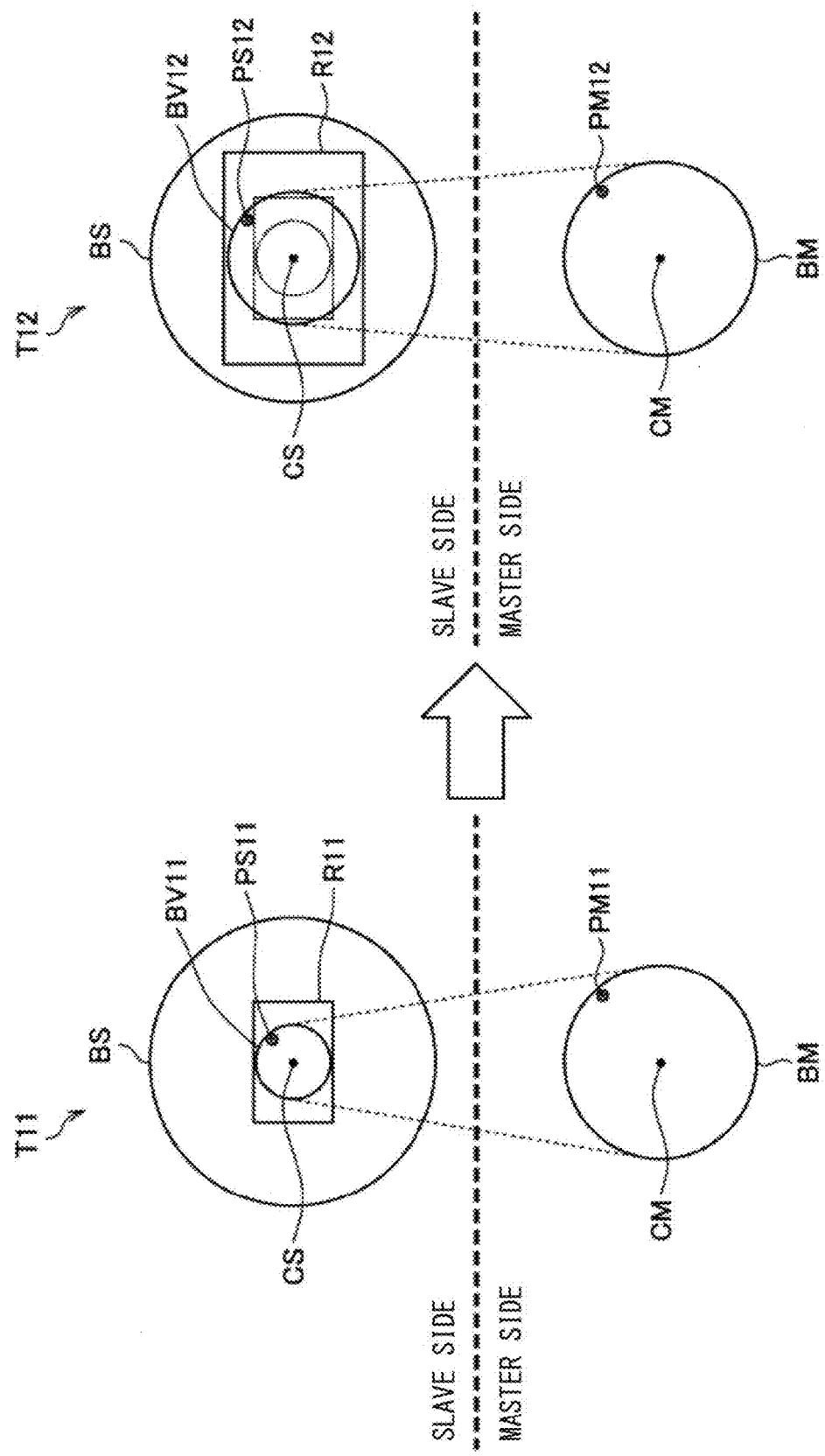
FIG. 4 is a conceptual diagram for describing decrease control by a control apparatus 50 according to the same embodiment.

FIG. 4 is a conceptual diagram for describing the decrease control by the control apparatus 50 according to the present embodiment. FIG. 4 illustrates a center CM of the movable range of the operation body 210 included in the master apparatus and a boundary BM of the movable range of the operation body 210. In addition, FIG. 4 illustrates a center CS of a movable range of the contact section 112 included in the slave apparatus 10 and a boundary BS of the movable range of the contact section 112.

As described above, the control apparatus 50 may control the slave apparatus 10 on the basis of the operation magnification and the operation offset to move the contact section 112 of the slave apparatus 10 to a position corresponding to the master position. In an example illustrated in FIG. 4, the operation magnification may be controlled by the control apparatus 50 without changing the operation offset. In the example illustrated in FIG. 4, the operation offset is 0; however, a state in which the operation offset is added in advance may be adopted. The size of the operation region of the slave apparatus 10 corresponding to the movable range of the master apparatus 20 may be then changed in accordance with control of the operation magnification.

In a state T11 illustrated in FIG. 4, a boundary of the operation region of the slave apparatus 10 corresponding to the movable range of the master apparatus 20 is a boundary BV11. In addition, a center of the operation region in the state T11 coincides with the center CS of the movable range of the contact section 112.

In addition, FIG. 4 also illustrates an imaging range of which an image is captured by the imaging unit 32 of the imaging apparatus 30. It is to be noted that in the present embodiment, the imaging range may be a display range displayed on the display apparatus 40. In the example illustrated in FIG. 4, an imaging range R11 in the state T11 includes the entire operation region of the slave apparatus 10. In addition, in the example illustrated in FIG. 4, a center of the imaging range R11 coincides with the center CS of the movable range of the contact section 112 and the center of the operation region.

In addition, the operation body 210 included in the master apparatus 20 is able to move a movable range inside the boundary BM, and the position of the operation body 210 in the state T11 is indicated as a master position PM11. In addition, in the state T11, the slave apparatus 10 is controlled to move the contact section 112 of the slave apparatus 10 to a slave position PS11 corresponding to the master position PM11.

Here, as illustrated in FIG. 4, the master position PM11 in the state T11 is in contact with the boundary BM of the movable range of the operation body 210, and the master position (that is, the operation body 210) is not movable any further in a direction away from the center CM of the movable range. In a case where the master position is located at a position where the master position is not movable in a specific direction in such a manner or at a position close to the position, in this description, it is detected that the master apparatus 20 has reached the movable range limit.

In the state T11 in FIG. 4, the master apparatus 20 has reached the movable range limit; therefore, the slave position PS11 is in contact with the boundary BV11 of the operation region of the slave apparatus 10 corresponding to the movable range of the master apparatus 20. However, a distance from the slave position PS11 to the boundary BS of the movable range of the contact section 112 is large, and as performance of the slave apparatus 10 itself, it is possible to further move the contact section 112 in the direction away from the center CS.

Accordingly, in a case where it is detected that the master apparatus 20 has reached the movable range limit, the control apparatus 50 according to the present embodiment may perform decrease control for decreasing both the operation magnification and the image magnification. It is to be noted that, in this description, "controlling both the operation magnification and the image magnification" may mean controlling the operation magnification and the image magnification substantially simultaneously to cause a change rate of the operation magnification and a change rate of the image magnification to be substantially the same as each other. Such a configuration makes it possible to enlarge the operation region and enlarge the imaging range without necessity of an additional operation by the user. Further, the control apparatus 50 according to the present embodiment controls the slave apparatus 10 to maintain a relationship between the master position in the movable range of the master apparatus 20 and the slave position in the operation region calculated from the operation magnification and the operation offset of the slave apparatus while performing the decrease control. Such a configuration makes it possible to move the contact section 112 of the slave apparatus 10 in a direction away from the center of the operation region while performing the decrease control and perform the decrease control without suspending the operation of the contract section 112 of the slave apparatus 10.

In the example illustrated in FIG. 4, transition from the state T11 to a state T12 takes place by the decrease control of the control apparatus 50. It is to be noted that FIG. 4 illustrates an example in which the user does not move the master position from the state T11 to the state T12, and the master position PM11 in the state T11 is the same as a master position PM12 in the state T12.

In the state T12, the operation region of the slave apparatus 10 corresponding to the movable range of the master apparatus 20 is larger than the operation region in the state T11, and a boundary BV12 of the operation region in the state T12 exists outside the boundary BV11 in the state T11. It is to be noted that in the example illustrated in FIG. 4, in transition from the state T11 to the T12, the operation offset is not changed; therefore, the center of the operation region in the state T12 also coincides with the center CS of the movable range of the contact section 112.

As described above, the control apparatus 50 according to the present embodiment controls the slave apparatus 10 to maintain the relationship between the master position in the movable range of the master apparatus 20 and the slave position in the operation region calculated from the operation magnification and the operation offset of the slave apparatus 10 while performing the decrease control. Accordingly, a slave position PS12 in the state T12 is moved to a position different from the slave position PS11 in the state T11 in accordance with enlargement of the operation region. Specifically, the slave position PS12 in the state T12 is moved in a direction away from the center of the operation region in the state T11 of the contact section 112 (the center CS of the movable range of the contact section 112). Such a moving direction corresponds to a direction from the center CM of the movable range of the master apparatus 20 to the master position PM12; therefore, such control is considered to be control that gives less discomfort to the user and reflects an intention of the user.

In addition, as described above, the control apparatus 50 according to the present embodiment controls the image magnification together with the operation magnification. An imaging range R12 in the state T12 is larger than the imaging range R11 in the state T11. As described above, the control apparatus 50 according to the present embodiment performs the decrease control to cause the change rate of the operation magnification and the change rate of the image magnification to be substantially the same as each other; therefore, even in the state T12, the imaging range R12 includes the entire operation region of the slave apparatus 10. It is to be noted that in the example illustrated in FIG. 4, the image offset is not changed in transition from the state T11 to the state T12; therefore, the center of the imaging range R12 in the state T12 also coincides with the center CS of the movable range of the contact section 112 and the center of the operation region. With such a configuration, the user does not lose track of the slave position PS12 (that is, the contact section 112 of the slave apparatus 10) while performing the decrease control.

Figure 5:
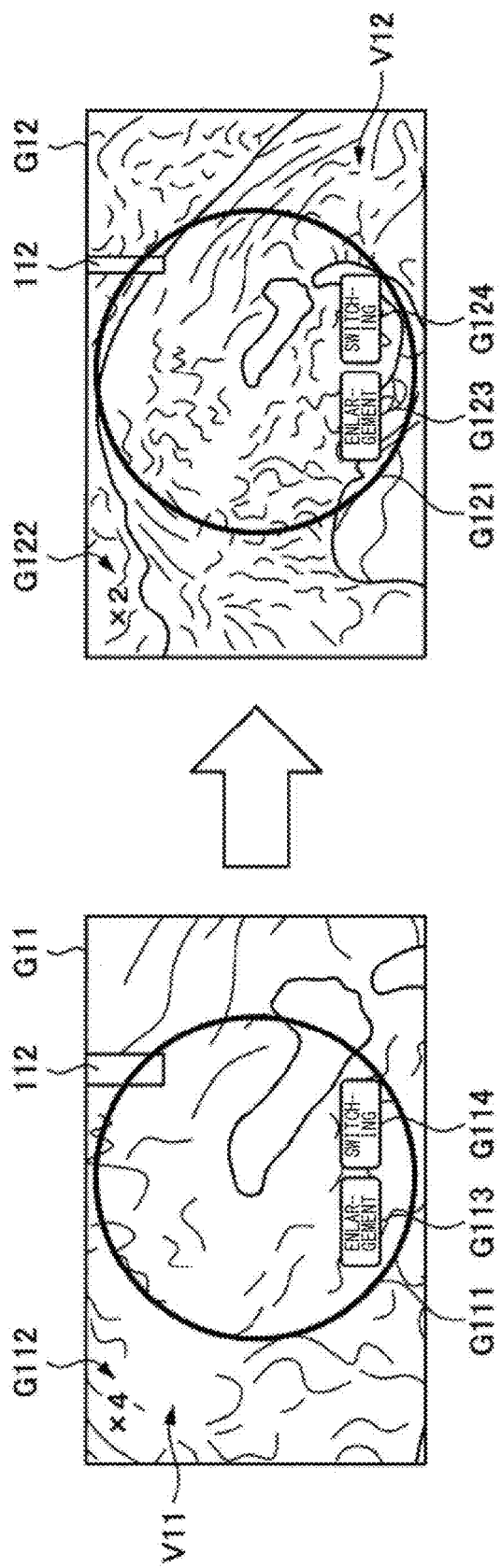
FIG. 5 illustrates an example of a display image displayed by a display apparatus 40 while performing decrease control on the basis of a detection result of whether or not a movable range limit has been reached.
Figure 6:
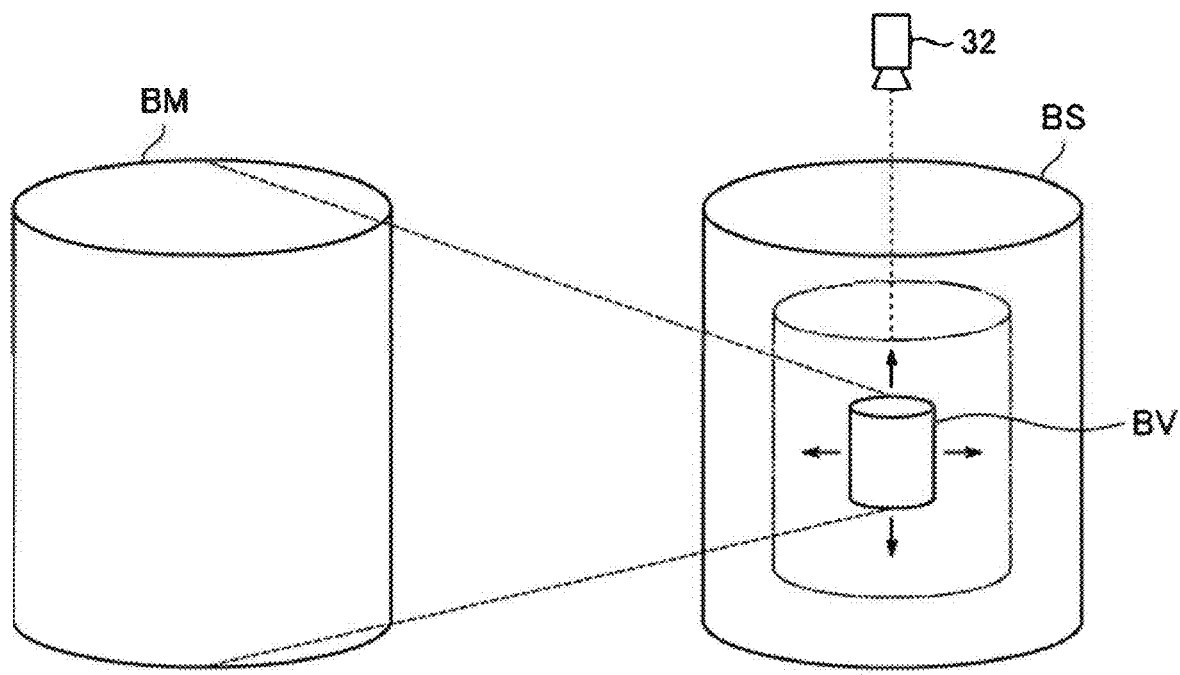
FIG. 6 three-dimensionally illustrates a movable range and an operation region in a case where decrease control is performed.

FIG. 5 illustrates an example of a display image displayed by the display apparatus 40 while performing the decrease control on the basis of a detection result of whether or not the master apparatus 20 has reached the movable range limit. FIG. 5 illustrates a display image G11 and a display image G12 respectively displayed on the display apparatus 40 in the state T11 and the state T12 illustrated in FIG. 4.

The display image G11 displayed in the state T11 is an image that is acquired by superimposing user interfaces G111 to G114 on a captured image V11 acquired by capturing an image of the imaging range illustrated in FIG. 4 by the imaging apparatus 30. Similarly, the display image G12 displayed in the state T12 is an image that is acquired by superimposing user interfaces G121 to G124 on a captured image V12 acquired by capturing an image of the imaging range R12 illustrated in FIG. 4 by the imaging apparatus 30. It is to be noted that the captured image V12 is an image acquired by capturing an image of a wider range, as compared with the captured image V11. In addition, for example, the control apparatus 50 may perform a process of superimposing the user interfaces G111 to G114 and G121 to G124.

The user interfaces G111 and G121 each indicate the boundary of the operation region, and are respectively the visualized boundaries BV11 and BV12 of the operation region illustrated in FIG. 4. Displaying the user interfaces G111 and G121 allows the user to grasp the operation region. In addition, as described above, the decrease control is performed to cause the change rate of the operation magnification and the change rate of the image magnification to be substantially the same as each other from the state T11 to the state T12, which causes the position of the user interface G111 and the position of the user interface G121 to be substantially the same as each other on a screen. The operation region on the screen is always fixed; therefore, a relationship between the master position and the slave position (the position of the contact section 112) on the screen is always fixed, which makes it possible for the user to grasp the operation region more easily and perform an operation more intuitively.

In addition, the user interfaces G112 and G122 each indicate the operation magnification. As described above, the decrease control is performed in transition from the state T11 to the state T12; therefore, as illustrated in FIG. 5, the operation magnification (a factor of two) indicated by the user interface G122 is smaller than the operation magnification (a factor of four) indicated by the user interface G112.

In addition, the user interfaces G113 and G123 are buttons for an increasing operation of the operation magnification and the image magnification. For example, the user operates the master apparatus 20 to superimpose the slave position on the user interfaces G113 and G123, thereby performing increase control for increasing the operation magnification and the image magnification. It is to be noted that the increasing operation is not limited to the example, and the increase control may be performed by any other operation.

In addition, the user interfaces G114 and G124 are buttons for an operation of switching a control mode on the basis of detection of whether or not the movable range limit has been reached (hereinafter also simply referred to as "control mode"). For example, the user operates the master apparatus 20 to superimpose the slave position on the user interfaces G114 and G124, thereby switching the control mode. In the present embodiment, there are two control modes including the decrease control and offset control to be described later, and the control mode may be switched by ON or OFF of an offset control flag, for example. In the example illustrated in FIG. 5, the control mode is the decrease control, and in a case where the operation of switching the control mode is performed, the offset control flag is turned on, and the control mode is switched to the offset control to be described later.

It is to be noted that FIGS. 4 and 5 two-dimensionally illustrate the movable ranges and the operation region, but in actuality, the movable ranges and the operation region may be three-dimensionally represented. FIG. 6 three-dimensionally illustrates the movable ranges and the operation region in performing the decrease control. FIG. 6 illustrates the boundary BM of the movable range of the master apparatus 20, the boundary BS of the movable range of the save apparatus 10, and the boundary BV of the operation region of the slave apparatus 10 corresponding to the movable range of the master apparatus 20. As illustrated in FIG. 6, in a case where the decrease control is performed to decrease the operation magnification, the operation region may be three-dimensionally increased.

The decrease control by the control apparatus 50 according to the present embodiment has been described above. Next, the offset control by the control apparatus 50 according to the present embodiment is described with reference to FIGS. 7 to 9.

Figure 7:
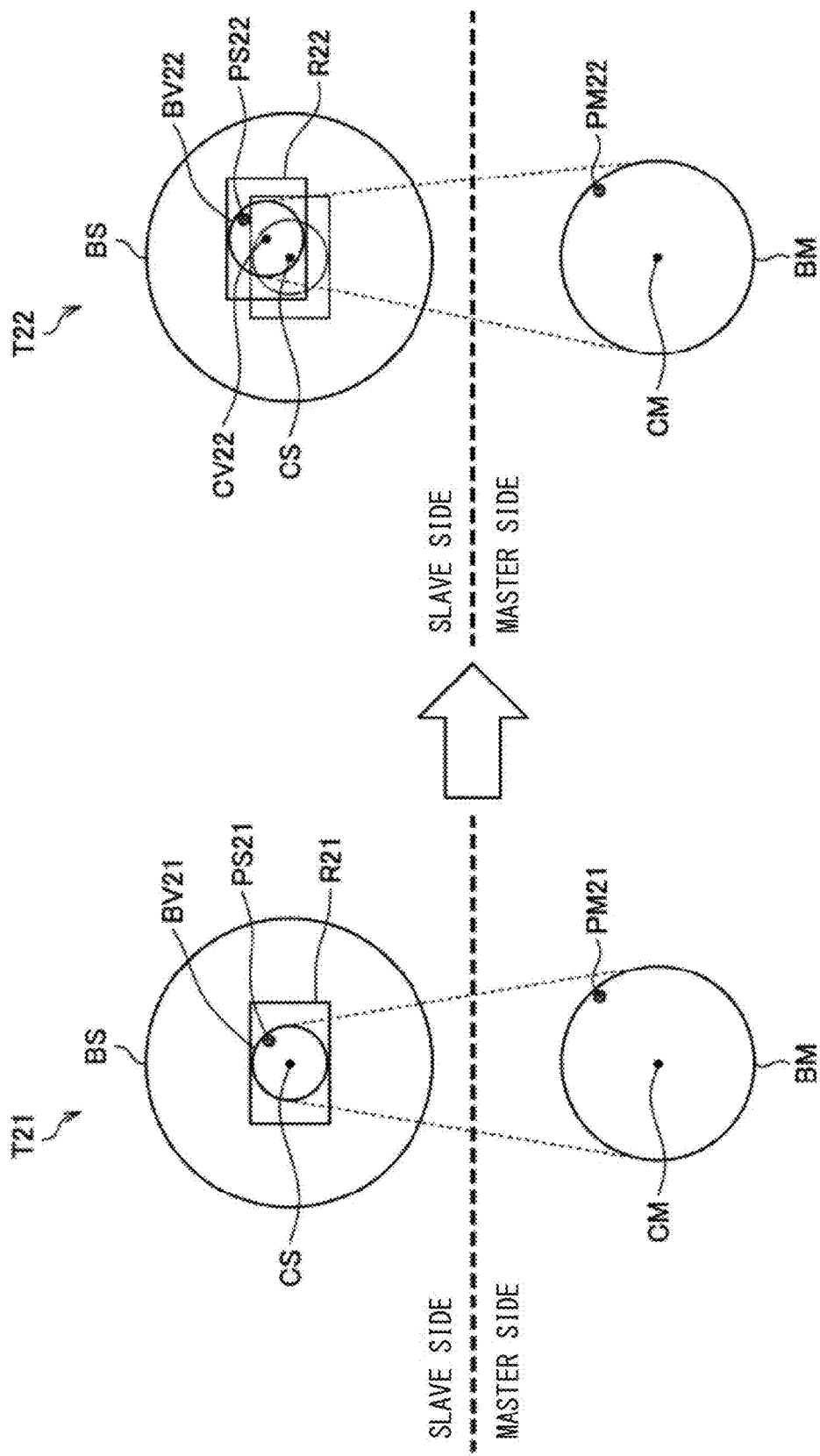
FIG. 7 is a conceptual diagram for describing offset control by the control apparatus 50 according to the present embodiment.

FIG. 7 is a conceptual diagram for describing the offset control by the control apparatus 50 according to the present embodiment. Of components illustrated in FIG. 7, the same components as those described with reference to FIG. 4 are denoted by the same reference numerals, and thus redundant description thereof is omitted.

As described above, the control apparatus 50 may control the slave apparatus 10 to move the contact section 112 of the slave apparatus 10 to a position corresponding to the master position on the basis of the operation magnification and the operation offset. In an example illustrated in FIG. 7, the operation offset may be controlled by the control apparatus 50 without changing the operation magnification. The operation region of the slave apparatus 10 corresponding to the movable range of the master apparatus 20 may be then moved in accordance with control of the operation offset.

In a state T21 illustrated in FIG. 7, the boundary of the operation region of the slave apparatus 10 corresponding to the movable range of the master apparatus 20 is a boundary BV21. In addition, the center of the operation region in the state T21 coincides with the center CS of the movable range of the contact section 112. In addition, in the example illustrated in FIG. 7, a center of an imaging range R21 of which an image is captured by the imaging unit 32 of the imaging apparatus 30 coincides with the center CS of the movable range of the contact section 112 and the center of the operation region.

In addition, the operation body 210 included in the master apparatus 20 is able to move the movable range inside the boundary BM, and the position of the operation body 210 in the state T21 is indicated as a master position PM21. In addition, in the state T21, the slave apparatus 10 is controlled to move the contact section 112 of the slave apparatus 10 to a slave position PS21 corresponding to the master position PM21.

Here, as illustrated in FIG. 7, the master position PM21 in the state T21 is in contact with the boundary BM of the movable range of the operation body 210, and the master apparatus 20 has reached the movable range limit. In the state T21, the master apparatus 20 has reached the movable range limit; therefore, the slave position PS21 is in contact with the boundary BV21 of the operation region of the slave apparatus 10 corresponding to the movable range of the master apparatus 20. However, a distance from the slave position PS21 to the boundary BS of the movable range of the contact section 112 is large, and as performance of the slave apparatus 10 itself, it is possible to further move the contact section 112 in a direction away from the center CS.

Accordingly, in a case where it is detected that the master apparatus 20 has reached the movable range limit, the control apparatus 50 according to the present embodiment may perform offset control for controlling both the operation offset and the image offset. It is to be noted that, in this description, "controlling both the operation offset and the image offset" may mean controlling the operation offset and the image offset substantially simultaneously to cause a moving direction and a movement amount of the operation region in actual space to be substantially the same as a moving direction and a movement amount of a display range (an imaging range in the present embodiment). Such a configuration makes it possible to move the operation region without necessity of an additional operation by the user, and also move the display range (the imaging range) to follow the operation region.

In a case where the master apparatus 20 has reached the movable range limit, it is considered that the user has an intention of moving the slave position in a direction away from the center of the operation region. For example, moving the operation region in a direction from the center of the operation region toward the slave position makes it possible to achieve such movement of the slave position. Accordingly, the control apparatus 50 according to the present embodiment may perform the offset control to move the operation region and the display range in the direction from the center of the operation region toward the slave position. Further, the control apparatus 50 according to the present embodiment controls the slave apparatus 10 to maintain a relationship between the master position in the movable range of the master apparatus 20 and the slave position in the operation region calculated from the operation magnification and the operation offset of the slave apparatus 10 while performing the offset control. Such a configuration makes it possible to move the contact section 112 of the slave apparatus 10 in a direction away from the center of the operation region while performing the offset control, and perform the decrease control without suspending the operation of the contract section 112 of the slave apparatus 10.

In the example illustrated in FIG. 7, transition from the state T21 to a state T22 takes place by the decrease control of the control apparatus 50. It is to be noted that FIG. 7 illustrates an example in which the user does not move the master position from the state T21 to the state T22, and the master position PM21 in the state T21 is the same as a master position PM22 in the state T22.

In the state T22, the operation region of the slave apparatus 10 corresponding to the movable range of the master apparatus 20 is moved to a position different from the operation region in the state T21. Specifically, a center CV22 of the operation region in the state T22 is moved in a direction from the center of the operation region in the state T21 (the center CS of the movable range of the contact section 112) toward the slave position PS21. In addition, similarly, a boundary BV22 of the operation region in the state T22 is also moved in a direction similar to the center CV22 of the operation region. It is to be noted that in the example illustrated in FIG. 7, in transition from the state T21 to the state T22, the operation magnification is not changed; therefore, the size of the operation region in the state T21 (the size of the boundary BV21) is the same as the size of the operation region in the state T22 (the size of the boundary BV22).

As described above, the control apparatus 50 according to the present embodiment controls the slave apparatus 10 to maintain the relationship between the master position in the movable range of the master apparatus 20 and the slave position in the operation region calculated from the operation magnification and the operation offset of the slave apparatus 10 while performing the offset control. Accordingly, the slave position PS22 in the state T22 is moved to a position different from the slave position PS21 in the state T22 in accordance with movement of the operation region. Specifically, the slave position PS22 in the state T22 is moved in a direction away from the center of the operation region in the state T21 (the center CS of the movable range of the contact section 112). Such a moving direction corresponds to a direction from the center CM of the movable range of the master apparatus 20 toward the master position PM22; therefore, such control is considered to be control that gives less discomfort to the user and reflects an intention of the user.

In addition, as described above, the control apparatus 50 according to the present embodiment controls the image offset together with the operation offset. An imaging range R22 in the state T22 is moved to a position different from the imaging range R21 in the state T21. As described above, in the present embodiment, the image offset is controlled to cause the moving direction and the movement amount of the operation region in actual space to be substantially the same as the moving direction and the movement amount of the imaging range. Accordingly, even in the state T22, the imaging range R22 includes the entire operation region of the slave apparatus 10, and a center of the imaging range R22 in the state T22 coincides with the center CV22 of the operation region. With such a configuration, the user does not lose track of the slave position PS22 (that is, the contact section 112 of the slave apparatus 10) while performing the offset control. It is to be noted that in the example illustrated in FIG. 7, in transition from the state T21 to the state T22, the image magnification is not changed; therefore, the size of the imaging range R22 in the state T22 is the same as the size of the imaging range R21 in the state T21.

Figure 8:
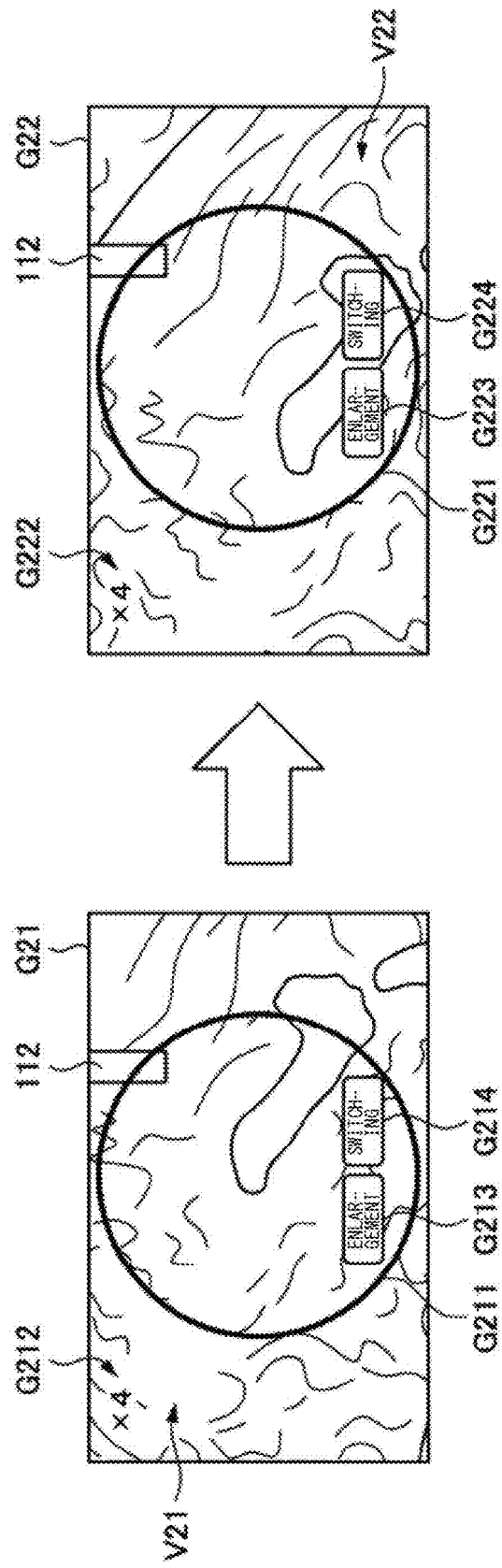
FIG. 8 illustrates an example of a display image displayed by the display apparatus 40 while performing offset control on the basis of a detection result of whether or not the movable range limit has been reached.
Figure 9:
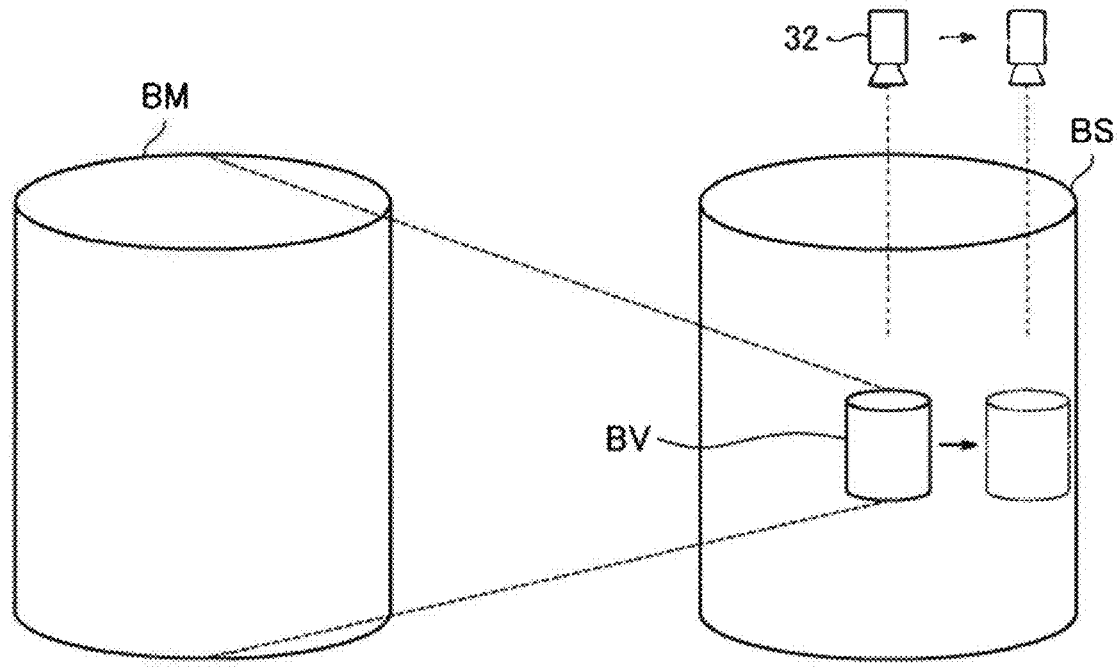
FIG. 9 three-dimensionally illustrates a movable range and an operation region in a case where offset control is performed.

FIG. 8 illustrates an example of a display image displayed by the display apparatus 40 while performing the offset control on the basis of a detection result of whether or not the movable range limit has been reached. FIG. 8 illustrates a display image G21 and a display image G22 respectively displayed on the display apparatus 40 in the state T21 and the state T22 illustrated in FIG. 7.

The display image G21 displayed in the state T21 is an image that is acquired by superimposing user interfaces G211 to G214 on a captured image V21 acquired by capturing an image of the imaging range R21 illustrated in FIG. 7 by the imaging apparatus 30. Similarly, the display image G22 displayed in the state T12 is an image that is acquired by superimposing user interfaces G221 to G224 on a captured image V22 acquired by capturing an image of the imaging range R22 illustrated in FIG. 7 by the imaging apparatus 30.

The user interfaces G211 and G221 each indicate the boundary of the operation region, and are respectively the visualized boundaries BV21 and BV22 of the operation region illustrated in FIG. 7. Displaying the user interfaces G211 and G221 allows the user to grasp the operation region. In addition, as described above, the offset control is performed to cause the moving direction and the movement amount of the operation region in actual space to be substantially the same as the moving direction and the movement amount of the imaging range from the state T21 to the state T22, which causes the position of the user interface G211 and the position of the user interface G221 to be substantially the same as each other on a screen. The operation region on the screen is always fixed; therefore, a relationship between the master position and the slave position (the position of the contact section 112) on the screen is always fixed, which makes it possible for the user to grasp the operation region more easily and perform an operation more intuitively.

In addition, the user interfaces G212 and G222 each indicate the operation magnification. As described above, the operation magnification is not changed in transition from the state T21 to the state T22; therefore, as illustrated in FIG. 8, the operation magnification (a factor of four) indicated by the user interface G212 is the same as the operation magnification (a factor of four) indicated by the user interface G222.

The user interfaces G213 and G223 are substantially the same as the user interfaces G113 and G123 described with reference to FIG. 5, and are not described here.

In addition, the user interfaces G214 and G224 are buttons for an operation of switching a control mode as with the user interfaces G114 and G124 described with reference to FIG. 5. For example, the user operates the master apparatus 20 to superimpose the slave position on the user interfaces G214 and G224, thereby switching the control mode. In the example illustrated in FIG. 8, the control mode is the offset control, and in a case where the operation of switching the control mode is performed, the offset control flag is turned off, and the control mode is switched to the decrease control.

It is to be noted that FIGS. 7 and 8 two-dimensionally illustrate the movable ranges and the operation region, but in actuality, the movable ranges and the operation region may be three-dimensionally represented. FIG. 9 three-dimensionally illustrates the movable ranges and the operation region in performing the offset control. FIG. 9 illustrates the boundary BM of the movable range of the master apparatus 20, the boundary BS of the movable range of the save apparatus 10, and the boundary BV of the operation region of the slave apparatus 10 corresponding to the movable range of the master apparatus 20. As illustrated in FIG. 6, in a case where the offset control is performed, the operation region is moved, and the imaging unit 32 is also moved in the substantially the same moving direction as a moving direction of the operation region by the substantially the same movement amount as a movement amount of the operation region.

2-3. Configuration of Control Apparatus

Figure 10:
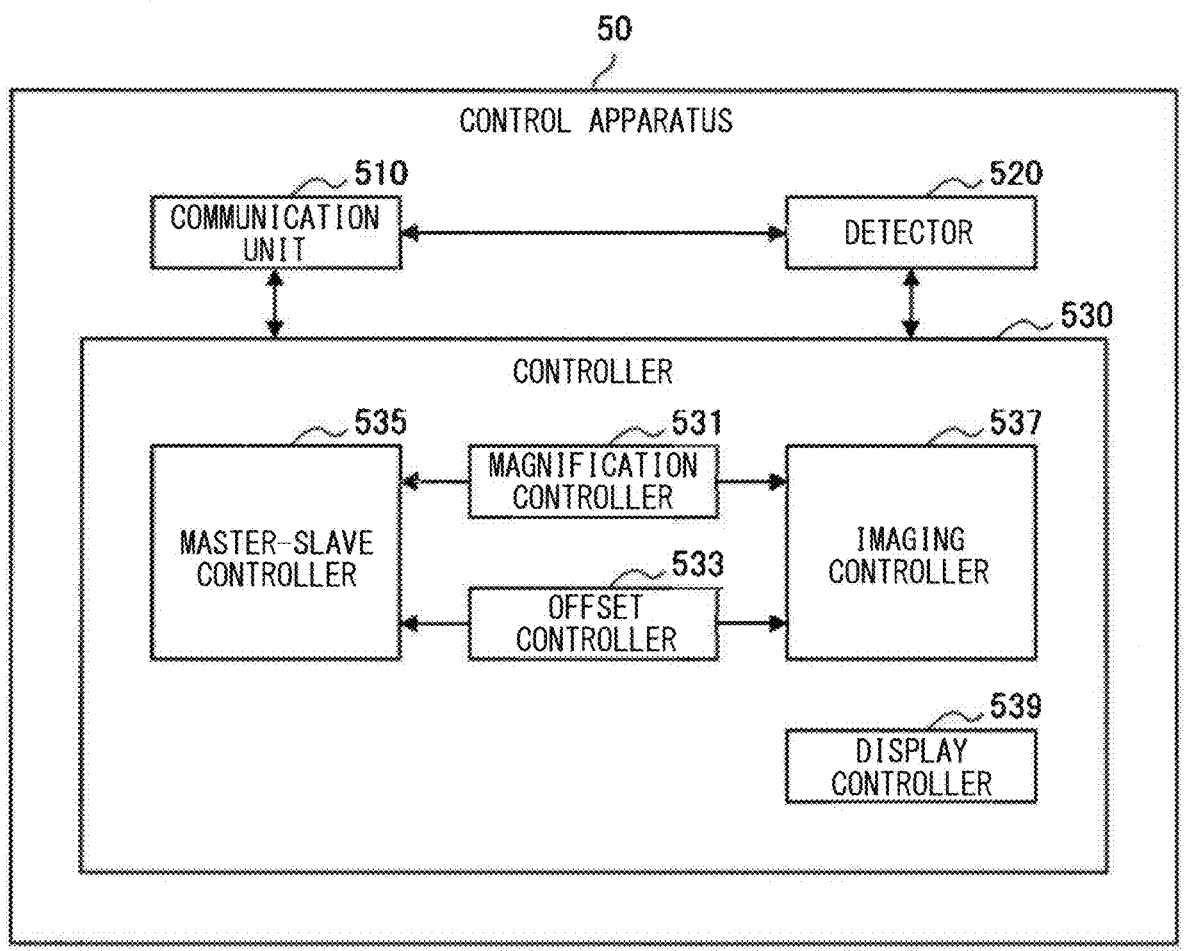
FIG. 10 is a block diagram illustrating a functional configuration example of the control apparatus 50 according to the same embodiment.

The control by the control apparatus 50 according to the present embodiment on the basis of a detection result of whether or not the movable range limit has been reached has been described above. Next, description is given of a functional configuration of the control apparatus 50 according to the present embodiment that may achieve the control described above with reference to FIG. 10. FIG. 10 is a block diagram illustrating a functional configuration example of the control apparatus 50 according to the present embodiment.

Referring to FIG. 10, the control apparatus 50 according to the present embodiment includes a communication unit 510, a detector 520, and a controller 530.

The communication unit 510 is a communication interface that mediates communication between the control apparatus 50 and another apparatus. The communication unit 510 supports any wireless communication protocol or any wired communication protocol, and performs communication with the slave apparatus 10, the master apparatus 20, the imaging apparatus 30, and the display apparatus 40 that have been described with reference to FIG. 1 directly or via an unillustrated network.

The detector 520 detects whether or not the master apparatus 20 has reached the movable range limit on the basis of information from the master apparatus 20 received by the communication unit 510. As described above, in the present embodiment, the movable range limit of the master apparatus 20 means the movable range limit of the operation body 210 that is an input interface included in the master apparatus 20. In addition, the movable limit of the master apparatus 20 is a state in which the operation body 210 is not movable in a specific direction or a state close to such a state.

The detector 520 may detect that the master apparatus 20 has reached the movable range limit, for example, in a case where the master position (the position of the operation body 210) specified on the basis of information received from the master apparatus 20 is in contact with the boundary of the movable range of the operation body 210 (the boundary BM illustrated in FIGS. 4 and 7). The detector 520 calculates the master position from a measurement value (for example, a joint angle) of an encoder provided at a joint included in the master apparatus 20, for example. Alternatively, the detector 520 may detect that the master apparatus 20 has reached the movable range limit, for example, in a case where the master position exists within a predetermined distance range from the boundary of the movable range of the operation body 210. Alternatively, in a case where the master apparatus 20 itself has a function of transmitting information indicating that the master apparatus 20 has reached the movable range limit, the detector 520 may detect that the master apparatus 20 has reached the movable range limit on the basis of the information from the master apparatus 20 received by the communication unit 510. Alternatively, the detector 520 may detect that the master apparatus 20 has reached the movable range limit in a case where the position of the operation body 210 specified on the basis of information received from the master apparatus 20 is in contact with or in proximity to a screen end of a screen displayed on the display apparatus 40 at present. In addition, the detector 520 may detect whether or not the master apparatus 20 has reached the movable range limit on the basis of a distance from a predetermined origin point to the master position. For example, in a case where the detector 520 monitors the distance from the predetermined origin point to the master position and the distance coincides with a distance from the predetermined origin point to the boundary of the movable range, the detector 520 may detect that the master apparatus 20 has reached the movable range limit.

The detector 520 outputs, to the controller 530, a detection result of whether or not the movable range limit has been reached.

The controller 530 controls the slave apparatus 10, the imaging apparatus 30, and the display apparatus 40 that are illustrated in FIG. 1. In addition, the controller 530 according to the present embodiment controls both the slave parameter and the image parameter on the basis of a detection result, by the detector 520, of whether or not the master apparatus 20 has reached the movable range limit, as described with reference to FIGS. 4 to 9. The controller 530 has functions as a magnification controller 531, an offset controller 533, a master-slave controller 535, an imaging controller 537, and a display controller 539.

The magnification controller 531 performs control of the operation magnification and the image magnification. The magnification controller 531 outputs the operation magnification to the master-slave controller 535, and outputs the image magnification to the imaging controller 537. For example, as described with reference to FIGS. 4 to 6, the magnification controller 531 performs decrease control of the operation magnification and the image magnification in a case where the detector 520 detects that the master apparatus 20 has reached the movable range limit. In addition, the magnification controller 531 may continuously perform the decrease control of the operation magnification and the image magnification while the detector 520 is detecting that the master apparatus 20 has reached the movable range limit.

For example, the magnification controller 531 may control the operation magnification and the image magnification substantially simultaneously, as described above. With such a configuration, it is not necessary for the user to perform an additional operation related to an image displayed in accordance with change in the operation magnification, thereby reducing a burden on the user.

In addition, the magnification controller 531 may control the operation magnification and the image magnification to cause the change rate of the operation magnification and the change rate of the image magnification to be substantially the same as each other. With such a configuration, a relationship between the size of the operation region and the size of the display range (which is the same as the imaging range in the present embodiment) is maintained, which makes it possible for the user to perform an operation more comfortably.

In addition, as described with reference to FIG. 4, the magnification controller 531 may control the operation magnification and the mage magnification to cause the center of the operation region and a center of the image displayed (the center of the imaging range in the present embodiment) to coincide with each other. With such a configuration, the center position of the operation region is not changed on a screen seen by the user; therefore, it is less likely to give discomfort to the user.

In addition, as described with reference to FIG. 5, the magnification controller 531 may perform increase control for increasing the operation magnification and the image magnification in accordance with a predetermined increasing operation. In addition, as described with reference to FIG. 5, the predetermined increasing operation may be an operation on the basis of an input to the master apparatus 20 by the user. With such a configuration, the user is able to increase the operation magnification and the image magnification without using an input device other than the master apparatus 20.

The offset controller 533 performs control of the operation offset and the image offset. The offset controller 533 outputs the operation offset to the master-slave controller 535, and outputs the image offset to the imaging controller 537. For example, as described with reference to FIGS. 7 to 9, the offset controller 533 performs control of the operation offset and the image offset (offset control) in a case where the detector 520 detects that the master apparatus 20 has reached the movable range limit. In addition, the magnification controller 531 may continuously perform control of the operation offset and the image offset while the detector 520 is detecting that the master apparatus 20 has reached the movable range limit.

In addition, as described with reference to FIG. 7, the offset controller 533 may control the operation offset and the image offset substantially simultaneously. With such a configuration, it is not necessary for the user to perform an additional operation related to the image displayed in accordance with change in the operation offset, thereby reducing a burden on the user.

In addition, as described with reference to FIG. 7, the offset controller 533 may control the operation offset and the image offset to cause the moving direction and the movement amount of the operation region of the slave apparatus 10 corresponding to the movable range of the master apparatus 20 to be substantially the same as the moving direction and the movement amount of the display range (which is the same as the imaging range in the present embodiment) of the image displayed. With such a configuration, a relationship between the position of the operation region and the position of the display range (which is the same as the imaging range in the present embodiment) is maintained, which makes it possible for the user to perform an operation more comfortably.

In addition, as described with reference to FIG. 7, the offset controller 533 may control the operation offset and the image offset to cause the center of the operation region and the center of the image displayed (the center of the imaging range in the present embodiment) to coincide with each other. With such a configuration, the center position of the operation region is not changed on the screen seen by the user; therefore, it is less likely to give discomfort to the user.

The master-slave controller 535 performs control of the slave apparatus 10 (master-slave control) on the basis of the master position specified on the basis of information from the master apparatus 20 received by the communication unit 510, the operation magnification controlled by the magnification controller 531, and the operation offset controlled by the offset controller 533.

It is to be noted that the master-slave control by the master-slave controller 535 according to the present embodiment may be similar to control of the slave apparatus in the existing master-slave system except that the operation magnification controlled by the magnification controller 531 and the operation offset controlled by the offset controller 533 are applied, and thus detailed description thereof is omitted.

The imaging controller 537 performs control of the imaging apparatus 30 (imaging control) on the basis of the image magnification controlled by the magnification controller 531 and image offset controlled by the offset controller 533. For example, in the present embodiment, the image magnification may be a zoom magnification (imaging magnification) of the imaging apparatus, and the imaging controller 537 may control the zoom magnification of the imaging apparatus to apply the image magnification controlled by the magnification controller 531 to the imaging control. In addition, in the present embodiment, the imaging controller 537 may move the imaging unit 32 by performing drive control of the robot arm included in the imaging apparatus 30 to apply the image offset to the imaging control.

The display controller 539 generates the display image displayed on the display apparatus 40 on the basis of a captured image acquired by imaging by the imaging apparatus 30. For example, the display controller 539 according to the present embodiment may perform a process of superimposing the user interfaces G111 to G114 and G211 to G214 described with reference to FIGS. 5 and 8 on the captured image to generate the display image.

Respective functions possessed by the controller 530 have been described above. The respective functions possessed by the controller 530 described above allows for achievement of control of the slave parameter and the image parameter on the basis of a detection result of whether or not the movable range limit has been reached as described with reference to FIGS. 4 to 9.

It is to be noted that the controller 530 may determine a combination of the slave parameter and the image parameter to be subjected to control, in accordance with an operation on the basis of an input to the master apparatus 20 by the user. In the present embodiment, the combination of the slave parameter and the image parameter to be subjected to control is one of a combination of the operation magnification and the image magnification described above, and a combination of the operation offset and the image offset described above, which respectively correspond to the decrease control by the magnification controller 531 and the offset control by the offset controller 533 described above. For example, the controller 530 may switch the control mode between the decrease control by the magnification controller 531 and the offset control by the offset controller 533 described above in accordance with the operation described with reference to FIG. 5. The controller 530 may manage the control mode by ON or OFF of the offset control flag, for example, as described above. With such a configuration, the user is able to switch the control mode without using an input device other than the master apparatus 20.

It is to be noted that an operation for determining the combination of the slave parameter and the image parameter to be subjected to control is not limited to the example described with reference to FIG. 5. For example, the decrease control may be performed in a case where the master position has reached an upper movable range limit of the operation region described with reference to FIGS. 6 and 9 (the slave position is in contact with the imaging unit 32 side in the operation region).

2-4. Operation of Control Apparatus

Figure 11:
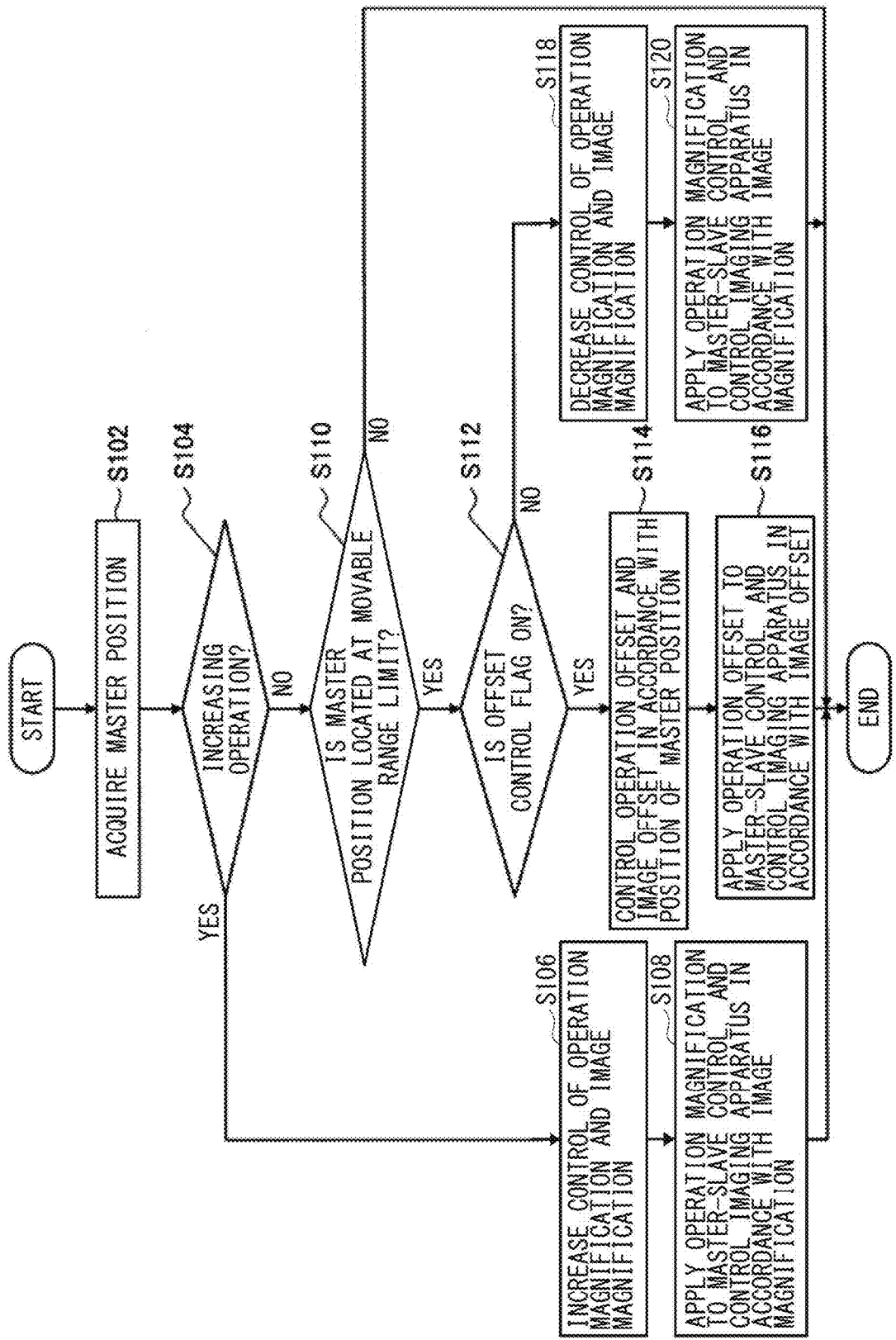
FIG. 11 is a flowchart illustrating an operation of the control apparatus 50 according to the same embodiment.

The functional configuration of the control apparatus 50 according to the present embodiment has been described above. Next, description is given of an operation of the control apparatus 50 according to the present embodiment. FIG. 11 is a flowchart illustrating the operation of the control apparatus 50 according to the present embodiment. It is to be noted that FIG. 11 mainly illustrates processing related to characteristics of the present embodiment, and the control apparatus 50 according to the present embodiment may perform processing not illustrated in FIG. 11 (for example, master-slave control processing in a case where it is not detected that the movable range limit has been reached).

Referring to FIG. 11, the master position is first acquired (S102). It is to be noted that information about the master position may be transmitted from the master apparatus 20 to the control apparatus 50, or may be specified on the basis of information from the master apparatus 20 received by the communication unit 510.

Next, the controller 530 determines whether or not the increasing operation is performed on the basis of the master position (S104). The increasing operation may be an operation of superimposing a button for the increasing operation displayed on the display apparatus 40 and the slave position on each other on the screen, as described with reference to FIG. 5, for example.

In a case where the increasing operation is performed (YES in S104), the magnification controller 531 of the controller 530 performs increase control of the operation magnification and the image magnification (S106). The master-slave controller 535 of the controller 530 then applies the operation magnification to the master-slave control, and the imaging controller 537 of the controller 530 controls the imaging apparatus 30 in accordance with the image magnification (S108).

In contrast, in a case where the increasing operation is not performed (NO in S104), the detector 520 detects whether or not the master position has reached the movable range limit (whether or not the master apparatus 20 has reached the movable range limit) (S110). In a case where it is not detected that the master position has reached the movable range limit (NO in S110), the processing ends.

In a case where the detector 520 detects that the master position has reached the movable range limit, and the offset control flag is ON (YES in S110 and YES in S112), the processing proceeds to step S114. In the step S114, the offset controller 533 of the controller 530 controls both the operation offset and the image offset in accordance with the master position. Thereafter, the master-slave controller 535 applies the operation offset to the master-slave control, and the imaging controller 537 controls the imaging apparatus 30 in accordance with the image offset (S116).

In a case where the detector 520 detects that the master position has reached the movable range limit, and the offset control flag is OFF (YES in S110 and NO in S112), the processing proceeds to step S118. In the step S118, the magnification controller 531 performs decrease control of the operation magnification and the image magnification. Thereafter, the master-slave controller 535 applies the operation magnification to the master-slave control, and the imaging controller 537 controls the imaging apparatus 30 in accordance with the image magnification (S120).

2-5. Effects

The first embodiment of the present disclosure has been described above. According to the first embodiment described above, the controller 530 of the control apparatus 50 detects whether or not the master apparatus 20 has reached the movable range limit, and controls the slave parameter and the image parameter on the basis of a detection result of whether or not the movable range limit has been reached. Such a configuration makes it possible to continue an operation intended by the user without suspending remote control of the slave apparatus 10 and without using an input device other than the master apparatus, and reduce a burden on the user.

3. Second Embodiment

In the first embodiment described above, an example in which the master-slave system 1000 includes one slave apparatus 10 and one master apparatus 20 has been described. However, the present technology is not limited to the example, and the number of slave apparatuses and the number of master apparatuses included in the master-slave system may be plural.

As a second embodiment of the present disclosure, a master-slave system 2000 including two slave apparatuses and two master apparatuses is described below. It is to be noted that a configuration of the master-slave system 2000 according to the present embodiment is partially substantially the same as the configuration of the master-slave system 1000 according to the first embodiment described above, and is described while redundant description thereof is omitted as appropriate.

3-1. System Configuration

Figure 12:
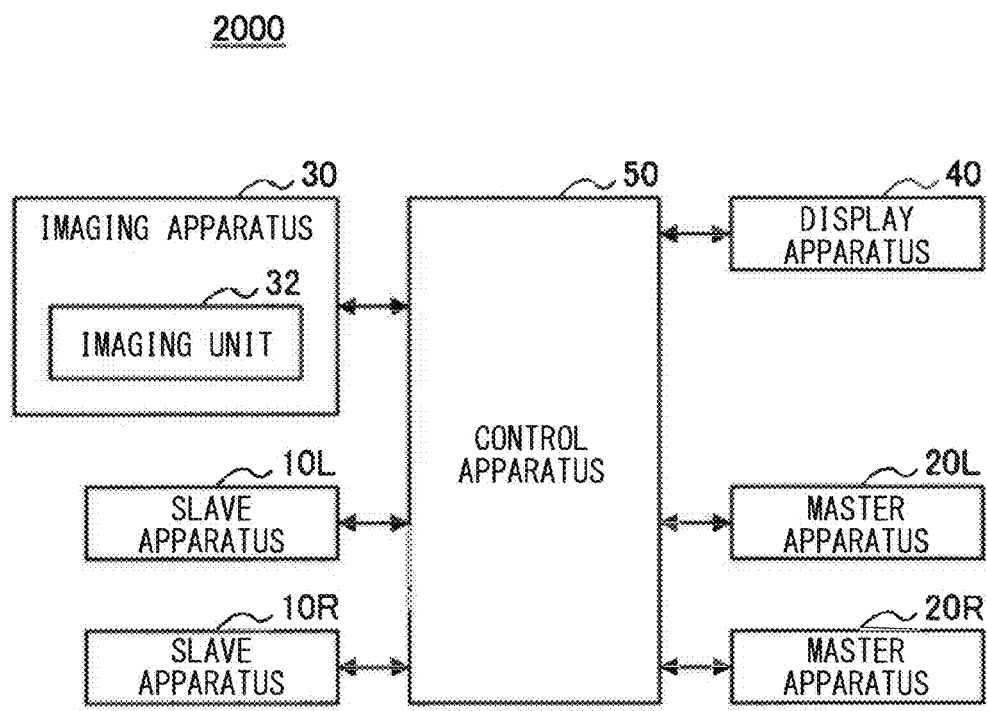
FIG. 12 is a schematic configuration diagram of a master-slave system 2000 according to a second embodiment of the present disclosure.

FIG. 12 is a schematic configuration diagram of the master-slave system 2000 according to the second embodiment of the present disclosure. As illustrated in FIG. 12, the master-slave system 2000 is a master-slave mode operation system including slave apparatuses 10L and 10R, master apparatuses 20L and 20R, the imaging apparatus 30, the display apparatus 40, and the control apparatus 50.

In the master-slave system 2000 illustrated in FIG. 12, the slave apparatus 10L and the master apparatus 20L correspond to each other, and the slave apparatus 10R and the master apparatus 20R correspond to each other.

The slave apparatus 10L and the slave apparatus 10R are slave-side apparatuses in the master-slave system 2000. The slave apparatus 10L may be controlled by the control apparatus 50 in accordance with an input operation to the master apparatus 20L, and the slave apparatus 10R may be controlled by the control apparatus 50 in accordance with an input operation to the master apparatus 20R. It is to be noted that configurations of the slave apparatus 10L and the slave apparatus 10R may be similar to the configuration of the slave apparatus 10 according to the first embodiment described with reference to FIG. 2, for example.

The master apparatus 20L and the master apparatus 20R are master-side apparatuses in the master-slave system 2000. The master apparatus 20L may be used for an operation of the slave apparatus 10L, and the master apparatus 20R may be used for an operation of the slave apparatus 10R. For example, the master apparatus 20L may be operated by the left hand of the user, and the master apparatus 20R may be operated by the right hand of the user. It is to be noted that configurations of the master apparatus 20L and the master apparatus 20R may be similar to the configuration of the master apparatus 20 according to the first embodiment described with reference to FIG. 3, for example.

The configurations of the imaging apparatus 30 and the display apparatus 40 according to the present embodiment are the same as the configurations of the imaging apparatus 30 and the display apparatus 40 according to the first embodiment, and are not described here.

The control apparatus 50 according to the present embodiment is an apparatus that controls each of other apparatuses included in the master-slave system 2000. A functional configuration of the control apparatus 50 according to the present embodiment is similar to that of the control apparatus 50 according to the first embodiment illustrated in FIG. 10, but functions of some blocks may be different. Referring to FIG. 10, the functional configuration of the control apparatus 50 according to the present embodiment that is different from that of the control apparatus 50 according to the first embodiment is mainly described below.

3-2. Configuration of Control Apparatus

The communication unit 510 according to the present embodiment is a communication interface that mediates communication between the control apparatus 50 according to the present embodiment and another apparatus, as with the communication unit 510 according to the first embodiment.

The detector 520 according to the present embodiment detects whether or not the master apparatus has reached the movable range limit on the basis of information from the master apparatus 20 received by the communication unit 510, as with the detector 520 according to the first embodiment. However, as described above, the master-slave system 2000 according to the present embodiment includes a plurality of master apparatuses 20L and 20R. Accordingly, the detector 520 according to the present embodiment may independently detect whether or not each of the plurality of master apparatuses 20L and 20R has reached the movable range limit.

The controller 530 controls the slave apparatuses 10L and 10R, the imaging apparatus 30, and the display apparatus 40 illustrated in FIG. 12, as with the controller 530 according to the first embodiment. In addition, the controller 530 according to the present embodiment controls both the slave parameter and the image parameter on the basis of a detection result, by the detector 520, of whether or not the master apparatus 20L or the master apparatus 20R has reached the movable range limit, as with the controller 530 according to the first embodiment. Of functions of the controller 530 illustrated in FIG. 10, functions as the imaging controller 537 and the display controller 539 according to the present embodiment are substantially the same as the functions of the imaging controller 537 and the display controller 539 according to the first embodiment. The following describes functions of the magnification controller 531, the offset controller 533, and the master-slave controller 535 according to the present embodiment that are different from those in the first embodiment.

The magnification controller 531 according to the present embodiment performs control of the operation magnification and the image magnification common to left and right sides, as with the magnification controller 531 according to the first embodiment. The magnification controller 531 according to the present embodiment may perform the decrease control of the operation magnification and the image magnification in a case where the detector 520 detects that at least one of the master apparatus 20L or the master apparatus 20R has reached the movable range limit.

The offset controller 533 according to the present embodiment performs control of the operation offset and the image offset common to the left and right sides, as with the offset controller 33 according to the first embodiment. The offset controller 533 according to the present embodiment may perform control of the operation offset and the image offset in a case where the detector 520 detects that at least one of the master apparatus 20L or the master apparatus 20R has reached the movable range limit. In addition, in a case where the detector 520 detects that the master apparatus 20L has reached the movable range limit, the offset controller 533 according to the present embodiment may perform control of the operation offset and the image offset on the basis of a master position of the master apparatus 20L (hereinafter also referred to as "left master position"). Further, in a case where the detector 520 detects that the master apparatus 20R has reached the movable range limit, the offset controller 533 according to the present embodiment may perform control of the operation offset and the image offset on the basis of a master position of the master apparatus 20R (hereinafter also referred to as "right master position").

The master-slave controller 535 according to the present embodiment performs the master-slave control on the basis of the master position, the operation magnification controlled by the magnification controller 531, and the operation offset controlled by the magnification controller 531, as with the master-slave controller 535 according to the first embodiment. However, as described above, the master-slave system 2000 according to the present embodiment includes the plurality of slave apparatuses 10L and 10R and the plurality of master apparatuses 20L and 20R. Accordingly, the master-slave controller 535 according to the present embodiment may control the slave apparatus 10L on the basis of the master position of the master apparatus 20L, and may control the slave apparatus 10R on the basis of the master position of the master apparatus 20R.

The respective functions possessed by the controller 530 have been described above. Incidentally, the controller 530 according to the present embodiment may determine a combination of the slave parameter and the image parameter to be subjected to control, in accordance with an operation on the basis of an input to the master apparatus by the user, as with the controller 530 according to the first embodiment described above. For example, the controller 530 according to the present embodiment may switch the control mode between the decrease control by the magnification controller 531 and the offset control by the offset controller 533 described above in accordance with the operation described with reference to FIG. 5.

However, as described above, the master-slave system 2000 according to the present embodiment includes the plurality of master apparatuses 20L and 20R; therefore, a combination thereof makes it possible to easily input a more complicated operation than the example described in the first embodiment. Accordingly, the controller 530 according to the present embodiment may determine the combination of the slave parameter and the image parameter to be subjected to control, in accordance with an operation on the basis of inputs to the plurality of master apparatuses 20L and 20R.

For example, the controller 530 according to the present embodiment may switch the control mode (that is, determine the combination of the slave parameter and the image parameter to be subjected to control) on the basis of a relationship between the left master position and the right master position. For example, the controller 530 according to the present embodiment may switch the control mode in accordance with whether or not a distance from the left master position to the right master position is small (for example, the distance is equal to or less than a predetermined threshold value).

Alternatively, the controller 530 according to the present embodiment may switch the control mode on the basis of a relationship between a slave position of the slave apparatus 10L (hereinafter also referred to as "left slave position") and a slave position of the slave apparatus 10R (hereinafter also referred to as "right slave position"). For example, the controller 530 according to the present embodiment may switch the control mode in accordance with whether or not a distance from the left slave position to the right slave position is small (for example, the distance is equal to or less than a predetermined threshold value).

Figure 13:
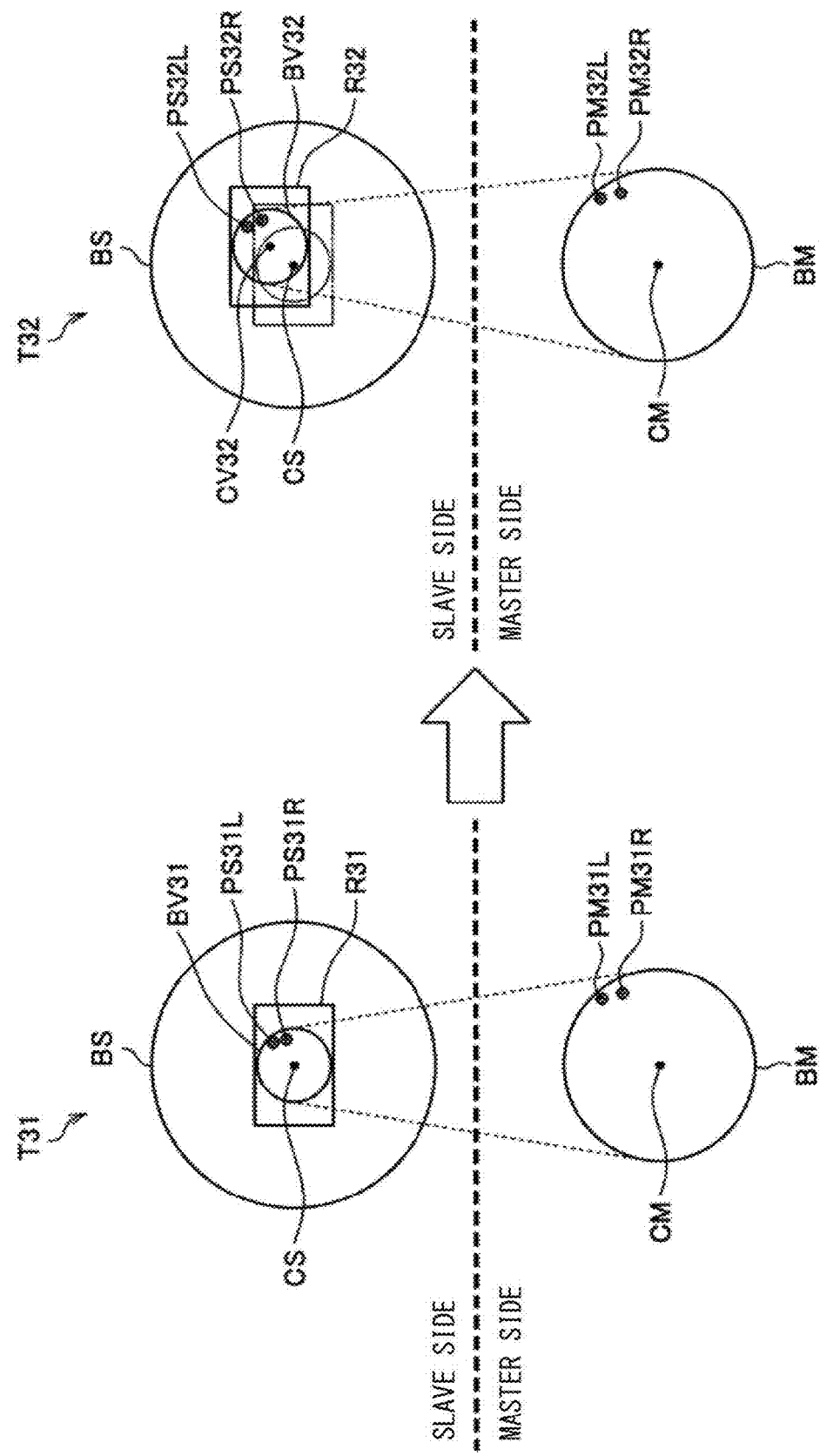
FIG. 13 is a conceptual diagram illustrating an example of offset control according to the same embodiment.

With reference to FIG. 13, the following describes, as one example, an example in which the offset control is performed in a case where the detector 520 detects that at least one of the master apparatus 20L or the master apparatus 20R has reached the movable range limit and the distance from the left master position to the right master position is small.

FIG. 13 is a conceptual diagram illustrating an example of the offset control according to the present embodiment. Of components illustrated in FIG. 13, the same components as those described with reference to FIG. 4 are denoted by the same reference numerals, and thus redundant description thereof is omitted. It is to be noted that for ease of description, the example illustrated in FIG. 13 indicates an example in which a movable range of the slave apparatus 10L and a movable range of the slave apparatus 10R coincide with each other and a movable range of the master apparatus 20L and a movable range of the master apparatus 20R coincide with each other, but the present technology is not limited to the example.

In a state T31 illustrated in FIG. 13, a boundary of each of operation regions of the slave apparatus 10L and the slave apparatus 10R respectively corresponding to the movable ranges of the master apparatus 20L and the master apparatus 20R is a boundary BV31. In addition, the center of each of the operation regions in the state T31 coincides with the center CS of each of the movable ranges of the slave apparatus 10L and the slave apparatus 10R. In addition, in the example illustrated in FIG. 13, a center of the imaging range R31 of which an image is captured by imaging by the imaging unit 32 of the imaging apparatus 30 coincides with the center CS of each of the movable ranges of the slave apparatus 10L and the slave apparatus 10R and the center of each of the operation regions.

The left master position of the master apparatus 20L and the right master position of the master apparatus 20R in the state T31 are respectively represented as a left master position PM31L and a right master position PM31R. In addition, in the state T31, the slave apparatus 10L and the slave apparatus 10R are controlled to respectively move the left master position of the slave apparatus 10L and the right master position of the slave apparatus 10R to a left slave position PS31L and a right slave position PS31R corresponding to the left master position PM31L and the right master position PM31R.

In addition, in the state T31 illustrated in FIG. 13, the left master position PM31L is in contact with a boundary BM of the movable range of the master apparatus 20L, and the master apparatus 20L has reached the movable range limit. Further, in the state T31 illustrated in FIG. 13, the right master position MP31R is not in contact with a boundary BM of the movable range of the master apparatus 20R, but exists near the left master position PM31L.

Accordingly, in the example illustrated in FIG. 13, transition from the state T31 to a state T32 takes place by offset control on the basis of detection of whether or not the left master position PM31L has reached the movable range limit. It is to be noted that FIG. 13 illustrates an example in which the user does not move the master position from the state T31 to the state T32, and the left master position MP31L and the right master position PM31R in the state T31 are the same as a left master position PM32L and a right master position PM32R in the state T32.

In the state T32, the operation regions of the slave apparatuses 10L and 10R corresponding to the movable ranges of the master apparatuses 20L and 20R are moved to a position different from the operation regions in the state T31. Specifically, a center CV32 of each of the operation regions in the state T32 is moved in a direction from the center of each of the operation regions in the state T31 (the center CS of each of the movable ranges of the slave apparatuses 10L and 10R) toward the left slave position PS31L. In addition, similarly, a boundary BV32 of each of the operation regions in the state T32 is also moved in a direction similar to that of the center CV32 of each of the operation regions. It is to be noted that in the example illustrated in FIG. 13, in transition from the state T31 to the state T32, the operation magnification is not changed; therefore, the size of each of the operation regions in the state T31 (the size of the boundary BV31) is the same as the size of each of the operation region in the state T32 (the size of the boundary BV32).

The example in which the offset control is performed by the controller 530 according to the present embodiment has been described above. It is to be noted that in the example described above, in a case where the detector 520 detects that at least one of the master apparatus 20L or the master apparatus 20R has reached the movable range limit and a distance from the left master position to the right master position is large, the decrease control of the operation magnification and the image magnification may be performed.

In addition, the method of determining the combination of the slave parameter and the image parameter to be subjected to control in accordance with an operation on the basis of inputs to the plurality of master apparatuses 20L and 20R is not limited to the example described above, and various method may be adopted. For example, in a case where both the left master position and the right master position have reached the movable range limit, the combination of the slave parameter and the image parameter to be subjected to control may be determined in accordance with a positional relationship between the left master position and the right master position. For example, in a case where the left master position has reached the movable range limit on the right side and the right master position has reached the movable range limit on the left side, the decrease control of the operation magnification and the image magnification may be performed. Further, in a case where the left master position has reached the movable range limit on the left side and the right master position has reached the movable range limit on the right side, the increase control of the operation magnification and the image magnification may be performed.

3-3. Operation of Control Apparatus

Figure 14:
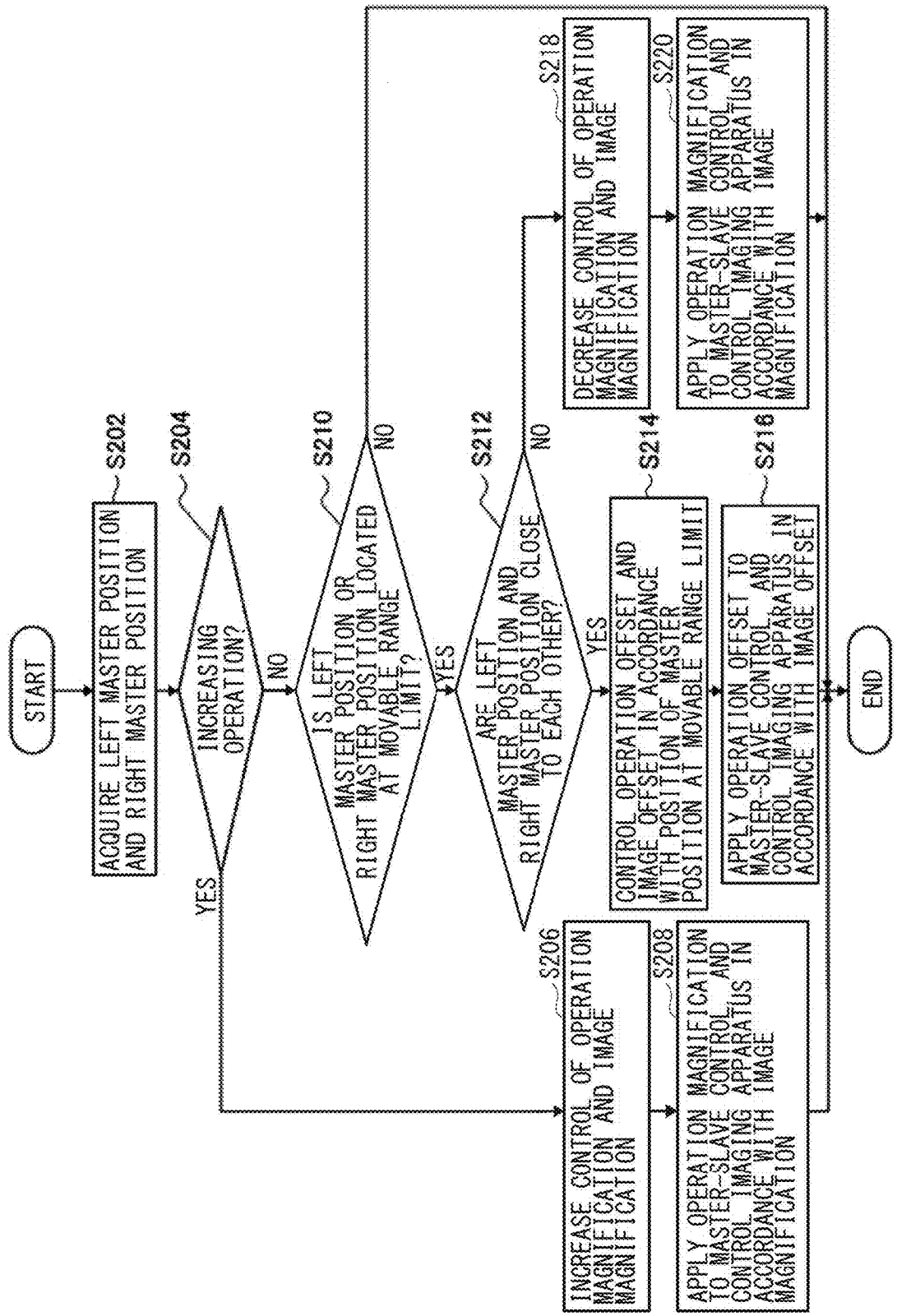
FIG. 14 is a flowchart illustrating an operation of the control apparatus 50 according to the same embodiment.

The functional configuration of the control apparatus 50 according to the present embodiment has been described above. Next, description is given of an operation of the control apparatus 50 according to the present embodiment. FIG. 14 is a flowchart illustrating the operation of the control apparatus 50 according to the present embodiment. It is to be noted that FIG. 14 mainly illustrates processing related to characteristics of the present embodiment, and the control apparatus 50 according to the present embodiment may perform processing not illustrated in FIG. 14 (for example, master-slave control processing in a case where it is not detected that the movable range limit has been reached).

Referring to FIG. 14, the left master position and the right master position are first acquired (S202). Next, the controller 530 determines whether or not the increasing operation is performed on the basis of the left master position and the right master position (S204). The increasing operation may be an operation of superimposing a button for the increasing operation displayed on the display apparatus 40 and the slave position on each other on the screen, as described with reference to FIG. 5, for example.

In a case where the increasing operation is performed (YES in S204), the magnification controller 531 of the controller 530 performs increase control of the operation magnification and the image magnification (S206). The master-slave controller 535 of the controller 530 then applies the operation magnification to the master-slave control, and the imaging controller 537 of the controller 530 controls the imaging apparatus 30 in accordance with the image magnification (S208).

In contrast, in a case where the increasing operation is not performed (NO in S204), the detector 520 detects whether or not the left master position or the right master position has reached the movable range limit (S210). In a case where neither the left master position nor the right master position has reached the movable range limit (NO in S210), the processing ends.

In a case where the detector 520 detects that the left master position or the right master position has reached the movable range limit and the left master position and the right master position are close to each other (YES in S210 and YES in S212), the processing proceeds to step S214. In the step S214, the offset controller 533 of the controller 530 controls both the operation offset and the image offset in accordance with a master position detected to have reached the movable range limit of the left master position and the right master position. Thereafter, the master-slave controller 535 applies the operation magnification to the master-slave control, and the imaging controller 537 controls the imaging apparatus 30 in accordance with the image magnification (S216).

In a case where the detector 520 detects that the left master position or the right master position has reached the movable range limit and the left master position and the right master position are not close to each other (YES in S210 and NO in S212), the processing proceeds to step S218. In the step S218, the magnification controller 531 performs the decrease control of the operation magnification and the image magnification. Thereafter, the master-slave controller 535 applies the operation magnification to the master-slave control, and the imaging controller 537 controls the imaging apparatus 30 in accordance with the image magnification (S220).

4. Modification Examples

The embodiments of the present disclosure have been described above. The following describes some modification examples according to the present disclosure. It is to be noted that, the respective modification examples described below may be separately applied to each of the embodiments of the present disclosure, or may be applied to each of the embodiments of the present disclosure in combination. In addition, the respective modification examples may be applied instead of the configurations described in the embodiments of the present disclosure described above, or may be applied in addition to the configuration described in the embodiments of the present disclosure described above.

<4-1. Modification Example 1>

In the embodiments described above, description has been given of an example in which the image magnification is applied to control of the zoom magnification of the imaging apparatus 30 and the image offset is applied to movement of the imaging unit 32 included in the imaging apparatus 30; however, the present technology is not limited to the example. For example, in a case where the display controller 539 crops (cuts) a partial region (a display range) of a captured image to generate a display image, the display controller 539 may determine a cropped region (the display range) on the basis of the image magnification and the image offset.

In such a case, the image magnification may be a ratio of the size of the captured image to the size of the cropped region. In addition, the image offset may be used to determine the position of the cropped region.

In addition, in a case where decrease control of the operation magnification and the image magnification is performed, the controller 530 may divide the display image and generate a display image to have display regions with different image magnifications. For example, the display controller 539 may generate a display image to have the decreased image magnification in a portion around the slave position and the maintained image magnification in a portion other than the portion. Such an example is described with reference to FIGS. 15 to 17. Each of FIGS. 15 to 17 is an explanatory diagram for describing an example in which a display image is generated to have the increased image magnification in a portion around the slave position and the maintained image magnification in a portion other than the portion.

Of components illustrated in FIGS. 15 and 16, the same components as those described with reference to FIG. 4 are denoted by the same reference numerals, and thus redundant description thereof is omitted.

Figure 15:
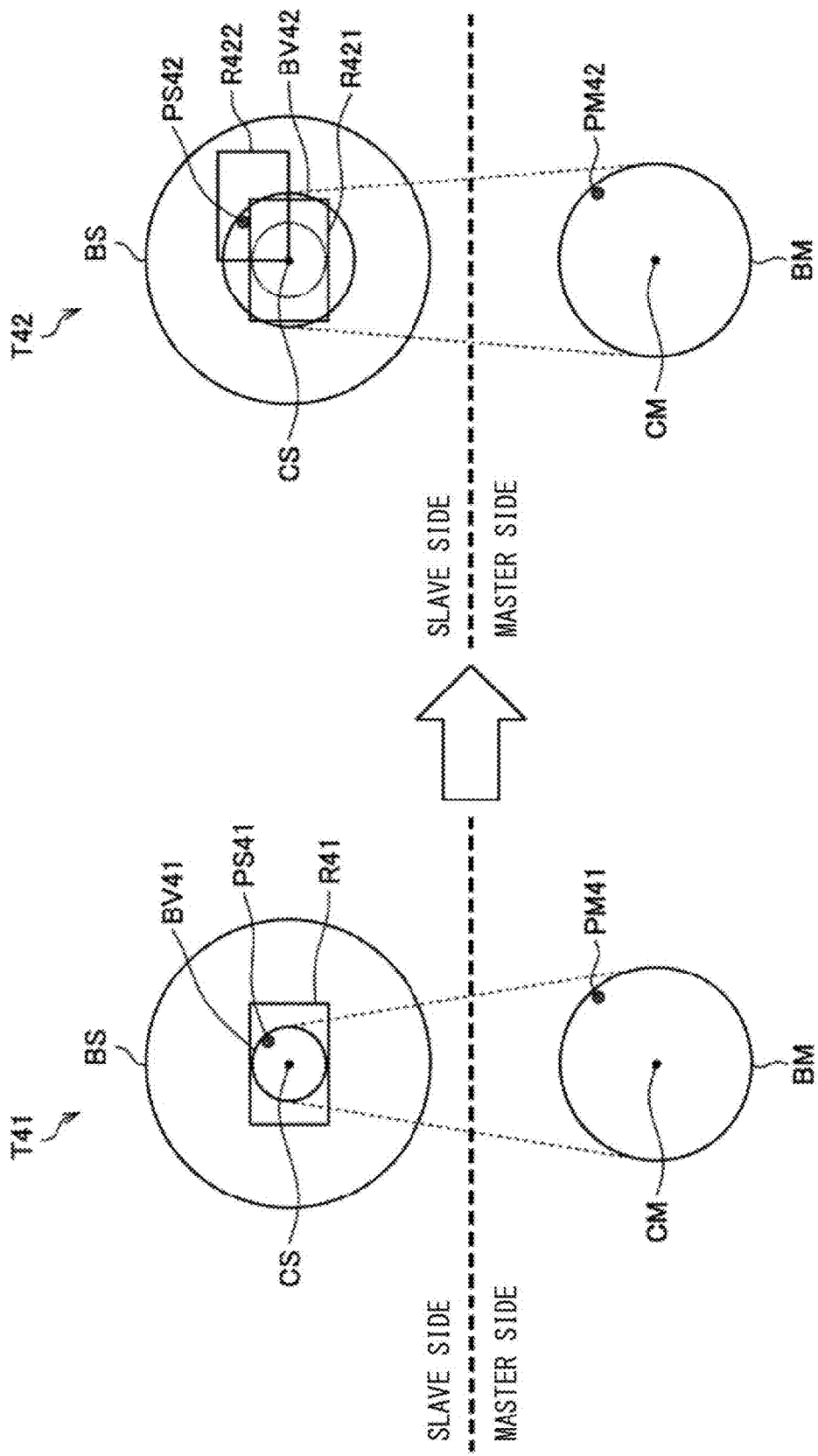
FIG. 15 is an explanatory diagram for describing a modification example 1.
Figure 16:
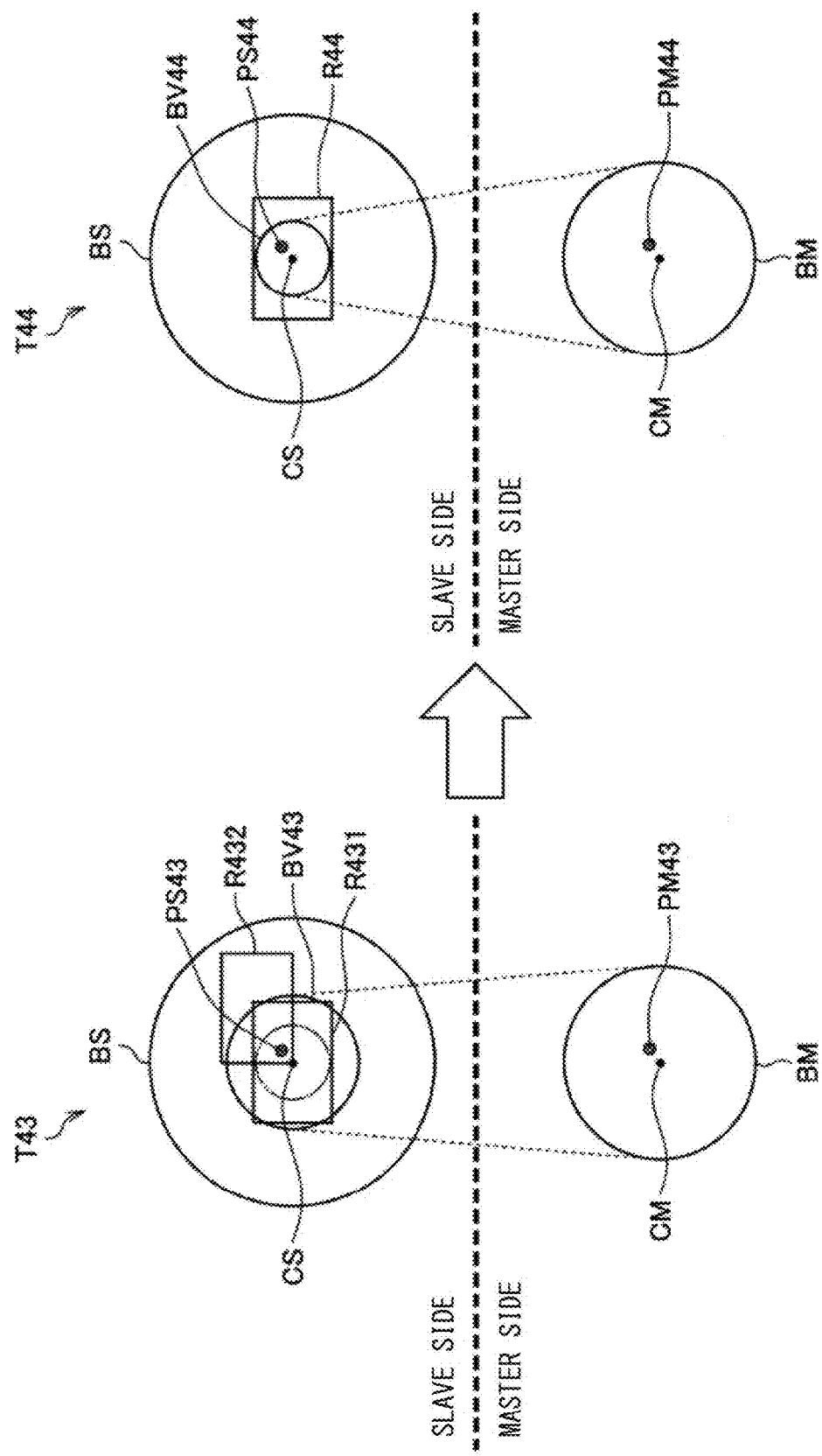
FIG. 16 is an explanatory diagram for describing the modification example 1.

In a state T41 illustrated in FIG. 15, the boundary of the operation region of the slave apparatus 10 corresponding to the movable range of the master apparatus 20 is a boundary BV41. In addition, FIG. 15 also illustrates a display range R41 displayed on the display apparatus 40. It is to be noted that although FIG. 15 does not illustrate the imaging range, the imaging range is at least larger than the display range R41, and may include the entire movable range of the slave apparatus 10, for example. In the example illustrated in FIG. 15, the display range R41 in the state T41 includes the entire operation region of the slave apparatus 10. In addition, in the example illustrated in FIG. 15, a center of the imaging range R41 coincides with the center CS of the movable range of the contact section 112 and the center of the operation region.

In addition, the operation body 210 included in the master apparatus 20 is able to move the movable range inside the boundary BM, and the position of the operation body 210 in the state T41 is indicated as a master position PM41. In addition, in the state T41, the slave apparatus 10 is controlled to move the contact section 112 of the slave apparatus 10 to a slave position PS41 corresponding to the master position PM11.

In the state T41 in FIG. 11, the master apparatus 20 has reached the movable range limit; therefore, the controller 530 may decrease the operation magnification. However, in the example illustrated in FIG. 15, the controller 530 may set two image magnifications including an image magnification in which the image magnification is maintained and an image magnification in which the image magnification is decreased.

In the example illustrated in FIG. 15, transition from the state T41 to a state T42 takes place by such decrease control. It is to be noted that FIG. 15 illustrates an example in which the user does not move the master position from the state T41 to the state T42, and the master position PM41 in the state T41 is the same as a master position PM42 in the state T42.

It is to be noted that decrease control of the operation magnification may be similar to the decrease control of the operation magnification described with reference to FIG. 4, for example. Accordingly, in the state T42, the operation region of the slave apparatus 10 corresponding to the movable range of the master apparatus 20 is larger than the operation region in the state T41, and a boundary BV42 of the operation region in the state T42 exists outside the boundary BV41 in the state T41. In addition, a slave position PS42 in the state T42 is moved to a position different from the slave position PS41 in the state T41 in accordance with enlargement of the operation region. Specifically, the slave position PS42 in the state T42 is moved in a direction away from the center of the operation region in the state T41 of the contact section 112 (the center CS of the movable range of the contact section 112).

However, as described above, in FIG. 15, the controller 530 may set two image magnifications. In the state T42, a first display range R421 and a second display range R422 are illustrated. The first display range R421 is based on the image magnification in which the image magnification is maintained before and after the decrease control, and the second display range R422 is based on the image magnification decreased after the decrease control from the image magnification before the decrease control.

Next, as in a state T43 illustrated in FIG. 16, in a case where a master position PM43 is moved, a slave position PS43 is also moved in accordance with such movement of the master position PM43. In the state T43 illustrated in FIG. 16, the operation magnification is maintained; therefore, a boundary BV43 of the operation region in the state T43 coincides with the boundary BV42 of the operation region in the state T42. Here, as in the state T43, in a case where the slave position PS43 is included in the first display range R431, the controller 530 may perform increase control.

In the example illustrated in FIG. 16, transition from the state T43 to a state T44 takes place by such increase control. It is to be noted that FIG. 16 illustrates an example in which the user does not move the master position from the state T43 to the state T44, and the master position PM43 in the state T43 is the same as a master position PM44 in the state T44.

In the state T44, the operation magnification is increased by the increase control, and the size of the boundary BV44 of the operation region is restored to the same size as that of the boundary BV41 of the operation region in the state T41 illustrated in FIG. 15, for example. In addition, in the state T44, a slave position PS44 is located at a position corresponding to the master position PM41. Further, in the state T44, the controller 530 sets, as a cropped region, a display range R44 on the basis of the image magnification in which the image magnification is maintained.

FIG. 17 schematically illustrates images displayed on the display apparatus 40 in the states T41 to T44 described with reference to FIGS. 15 and 16 as display images G41 to G44, respectively. Referring to FIG. 17, the display image G41 displayed in the state T41 includes an image of the display range R41.

In addition, in the state T42, two display ranges exist as described above; therefore, a screen displayed on the display apparatus 40 is divided. Specifically, the display image G42 displayed in the state T42 includes an image of a second display range R422 in which the image magnification is decreased, in a portion on the upper right of an image of the first display range R421 in which the image magnification is maintained. Similarly, the display image G43 displayed in the state T43 includes an image of a second display region R432 in which the image magnification is decreased, in a portion on the upper right of an image of a first display range R431 in which the image magnification is maintained.

Further, in the state T44, only one display range exists; therefore, division of the screen ends. The display image G44 displayed in the state T44 includes an image of the display range R44 having the same image magnification as that in the display range R41 in the state T41.

Description has been given of an example in which in a case where the decrease control of the operation magnification and the image magnification is performed, the controller 530 divides the screen (the display image) and generates a display image to have display regions with different image magnifications. According to the example described above, it is possible to decrease and check the image magnification in a portion around the slave position and perform an operation while maintaining the image magnification in a central portion. Further, in a case where the slave position is returned to inside the movable range, the increase control of the operation magnification and the image magnification is performed, and ends division of the screen, which makes it possible to perform a smooth operation without necessity of performing an additional operation. It is to be noted that a method of dividing the screen (the display image) is not limited to the example illustrated in FIG. 17.

<4-2. Modification Example 2>

Figure 18:
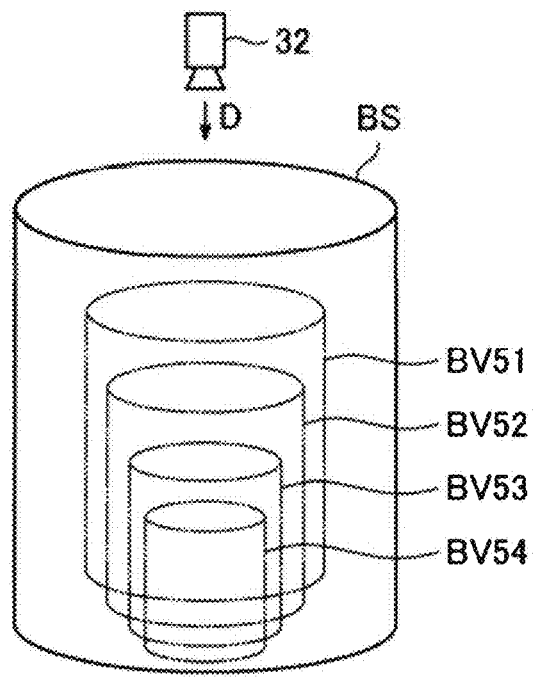
FIG. 18 is an explanatory diagram for describing a modification example 2.

In the embodiments described above, description has been given of an example in which switching between control of the operation magnification and the image magnification and control of the operation offset and the image offset is performed in accordance with an operation by the user; however, the present technology is not limited to the example. The control of the operation magnification and the image magnification and the control of the operation offset and the image offset may be performed simultaneously. Such an example is described as a modification example 2 with reference to FIG. 18. FIG. 18 is an explanatory diagram for describing the modification example 2.

FIG. 18 illustrates a movable range BS of the slave apparatus 10 and the imaging unit 32. In addition, FIG. 18 illustrates operation regions BV51 to BV54 of the slave apparatus 10 that may be achieved by control by the controller 530. The controller 530 may perform the offset control to move the operation region along an imaging direction D of the imaging unit 32 and also perform the decrease control or the increase control, thereby achieving transition among the operation regions BV51 to BV54.

For example, in a case where it is detected that the master apparatus 20 has reached the movable range limit, if the slave position is located on the imaging unit 32 side (top side in FIG. 18) of the operation region of the slave apparatus 10, the controller 530 may perform the increase control, and also perform the offset control to move the operation region in an upward direction in FIG. 18. In addition, in a case where it is detected that the master apparatus 20 has reached the movable range limit, if the slave position is located on side opposite to the imaging unit 32 (bottom side in FIG. 18) of the operation region of the slave apparatus 10, the controller 530 may perform the decrease control and also perform the offset control to move the operation region in a downward direction in FIG. 18. Such control may be effective in a case where finer work is performed on back side (bottom side in FIG. 18). In addition, in such a case, the controller 530 performs focusing control of the imaging unit 32 in accordance with the operation offset in the imaging direction D, which makes it possible to always focus on the center of the operation region, for example.

<4-3. Modification Example 3>

In the embodiments described above, description has been given of an example in which the movable range of the master apparatus 20 includes only a movable range that is a region where the master apparatus 20 is physically operable; however, the present technology is not limited to the example. For example, the movable range of the master apparatus 20 may include a first movable range and a second movable range. The first movable range is a region where the master apparatus 20 is physically operable, and the second movable range is a region that is smaller than the first movable range and exists in the first movable range. The first movable range is also referred to as "mechanical movable range (mechanical movable range)". The second movable range is a region determined by software, for example. Accordingly, hereinafter, the second movable range is also referred to as "software movable range (movable range on software)".

Figure 19:
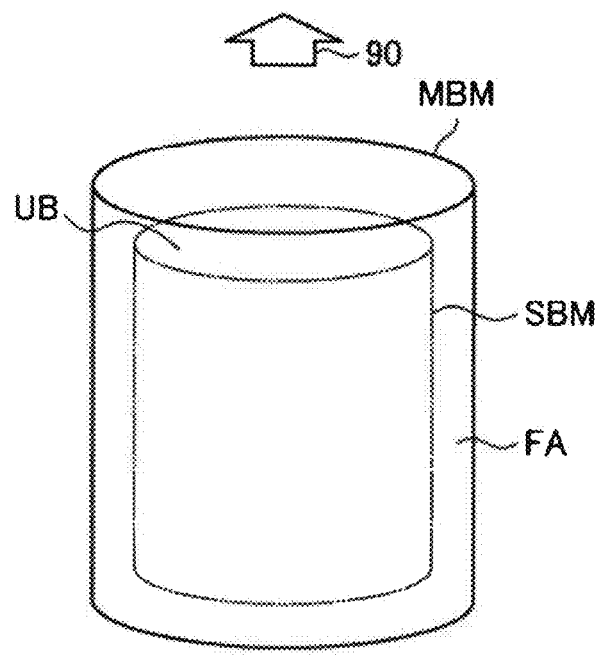
FIG. 19 is an explanatory diagram for describing a modification example 3.

In addition, in the embodiments described above, description has been given of an example in which whether or not the master apparatus 20 has reached the movable range limit is detected on the basis of only the mechanical movable range; however, the present technology is not limited to the example. For example, whether or not the master apparatus 20 has reached the movable range limit may be detected on the basis of the mechanical movable range and the software movable range. Specifically, in a case where the master position is located in a region between the mechanical movable range and the software movable range, the detector 520 may detect that the master position has reached the movable range limit. Such an example is described as a modification example 3 with reference to FIG. 19. FIG. 19 is an explanatory diagram for describing the mechanical movable range and the software movable range. FIG. 19 illustrates a mechanical boundary MBM and a software boundary SBM of the master apparatus 20.

The mechanical movable range is a region inside the mechanical boundary MBM illustrated in FIG. 19. The mechanical movable range may be calculated, as a region where a front end of the master apparatus 20 (for example, a front end of the operation body 210) is physically operable, from a length of a link included in the master apparatus 20 and a range of a rotatable angle of a joint, and the like, for example. The user is able to freely move the operation body 210 within the mechanical movable range. It is to be noted that in a case where the user moves the operation boy 210 around the mechanical boundary MBM to move the operation body 210 outside the mechanical movable range, there is a possibility that the operation body 210 is broken. Accordingly, it is desirable to prevent the operation body 210 from being moved outside the mechanical movable range by the user.

Accordingly, in the present modification example, it is sufficient if the software boundary SBM for narrowing the movable range of the master apparatus 20 is provided inside the mechanical boundary MBM. The software movable range is a region inside the software boundary SBM illustrated in FIG. 19. The software boundary SBM is set as a region smaller than the mechanical boundary MBM, for example, as illustrated in FIG. 19. Specifically, the software boundary SBM may be calculated as a region where the mechanical boundary MBM is narrowed by a predetermined region.

It is to be noted that in the present modification example, in a case where the master apparatus 20 is located in a feedback region FA between the mechanical movable range and the software movable range (between the mechanical boundary MBM and the software boundary SBM illustrated in FIG. 19), the detector 520 detects that the master apparatus 20 has reached the movable range limit. The detector 520 calculates the position of the front end of the operation body 210 from a measurement value of an encoder provided at a joint included in the master apparatus 20, for example. In a case where the calculated position of the front end of the operation body 210 is located at a position in the feedback region FA, the detector 520 detects that the master apparatus 20 has reached the movable range limit. In contrast, in a case where the calculated position of the front end of the operation body 210 is not located at a position in the feedback region FA, the detector 520 detects that the master apparatus 20 has not reached the movable range limit. It is to be noted that even in a case where the calculated position of the front end of the operation body 210 is in contact with the software boundary SBM, the detector 520 may detect that the master apparatus 20 has reached the movable range limit.

Further, in the present modification example, in a case where it is detected, on the basis of the feedback region FA, that the master apparatus 20 has reached the movable range limit, the controller 530 performs force feedback control for moving the operation body 210 in a direction opposite to a moving direction by the user. For example, in a case where it is detected that the operation body 210 has been moved into the feedback region FA to reach the movable range limit, the controller 530 moves the operation body 210 into the software movable range by the force feedback control. At this time, it is desirable that the controller 530 provide the operation body 210 with force larger than force inputted to the operation body 210 by the user.

With such a configuration, the operation body 210 is not moved outside the mechanical movable range. This makes it possible to prevent physical breakage of the master apparatus 20 caused by the operation body 210 moved outside the mechanical movable range. Further, preventing physical breakage of the master apparatus 20 makes it possible to improve safety in a case where the user operates the operation body 210.

In addition, such a configuration makes it possible for the controller 530 to provide the user with a feeling as if the operation body 210 is pushed back. Further, the user has the feeling as if the operation body 210 is pushed back, which makes it possible for the user to intuitively understand that it is not possible to move the operation body 210 beyond a position where the operation body 210 is pushed back.

<4-4. Modification Example 4>

In the embodiments described above, description has been given of an example in a case where the boundary BM of the movable range of the master apparatus 20 has the shape of a column, the decrease control is performed if the operation body 210 has reached a side surface of the column and it is thereby detected that the master apparatus 20 has reached the movable range limit; however, the present technology is not limited to the example. For example, in a case where the operation body 210 has reached one region of the boundary BM of the movable range of the master apparatus 20 existing in a direction corresponding to a direction away from a contact target and it is thereby detected that the master apparatus 20 has reached the movable range limit, the controller 530 may perform the decrease control.

Examples of the contact target include affected sites (such as skin, an organ and a blood vessel) of a patient in surgery. The direction away from the contact target is a direction where the contact section 112 of the slave apparatus 10 moves away from the contact target existing on the slave apparatus 10 side. Specifically, in a case where the contact section 112 is located above the contact target, the direction away from the contact target is a direction where the contact section 112 is moved upward. In addition, in a case where the contact section 112 is located below the contact target, the direction where the contact section 112 moves away from the contact target is a direction where the contact section 112 is moved downward. It is to be noted that the following describes an example in which the direction away from the contact target is a direction where the contact section 112 is moved upward; however, the direction away from the contact target is not limited to the example.

A direction corresponding to the direction away from the contact target is, for example, a direction where the user moves the operation body 210 in a case where the contact section 112 of the slave apparatus 10 is moved in a direction away from the contact target existing on the slave apparatus 10 side. Specifically, in a case where the contact section 112 is moved away from the contact target in a direction the contact section 112 is moved upward, the direction corresponding to the direction away from the contact target is a direction where the operation body 210 is moved upward. In addition, in a case where the contact section 112 is moved away from the contact target in a direction where the contact section 112 is moved downward, the direction corresponding to the direction away from the contact target is a direction where the operation body 210 is moved downward. It is to be noted that the following describes an example in which the direction corresponding to the direction away from the contact target is an upward-moving direction of the operation body 210; however, the direction corresponding to the direction away from the contact target is not limited to the example.

For example, as illustrated in FIG. 19, it is assumed that the boundary BM of the movable range of the master apparatus 20 has the shape of a column; a direction indicated by an arrow 90 is the direction away from the contact target; and a bottom surface UB of the software boundary SBM is one region. At this time, in a case where the operation body 210 has reached the bottom surface UB of the software boundary SBM and it is thereby detected that the master apparatus 20 has reached the movable range limit, the controller 530 performs the decrease control. Such a configuration makes it possible to enlarge the operation region and enlarge the imaging range without necessity of an additional operation by the user. Accordingly, the user is able to move the operation body 210 while looking at an image indicating a wide range.

It is to be noted that the shape of the boundary BM of the movable range of the master apparatus 20 is not limited to the column, and may be any shape. For example, the boundary BM of the movable range of the master apparatus 20 may have the shape of a sphere, or a shape such as a truncated cone, a quadrangular prism, or a triangular prism. In a case where the boundary BM of the movable range of the master apparatus 20 has the shape of a sphere, a partial region in the direction away from the contact target may be set as the one region.

In addition, displaying an image indicating a wide range by moving the operation body 210 upward makes it possible for the user to recognize a state around the operation body 210 in a wider range than in a case where an image indicating a narrow range is displayed. Accordingly, the user moves the operation body 210 upward and then moves the operation body 210 from side to side, which makes it possible to move the operation body 210 more safely than in a case where the operation body 210 is moved from side to side without moving the operation body 210 upward.

Here, control by the controller 530 in a case where the boundary BM of the movable range of the master apparatus 20 includes the mechanical boundary MBM and the software boundary SBM is described with reference to FIGS. 20 to 27. Specifically, the following describes an example of the decrease control in a case where the operation body 210 has reached the boundary BM of the movable range of the master apparatus 20 existing in a vertically upward-moving direction of the operation body 210 when the operation body 210 is moved upward and it is thereby detected that the master apparatus 20 has reached the movable range limit. Further, an example of the offset control and the increase control in a case where the operation of the operation body 210 and the increasing operation are performed after the decrease control is also described.

4-4-1. Decrease Control at Time of Movable Range Limit

Figure 20:
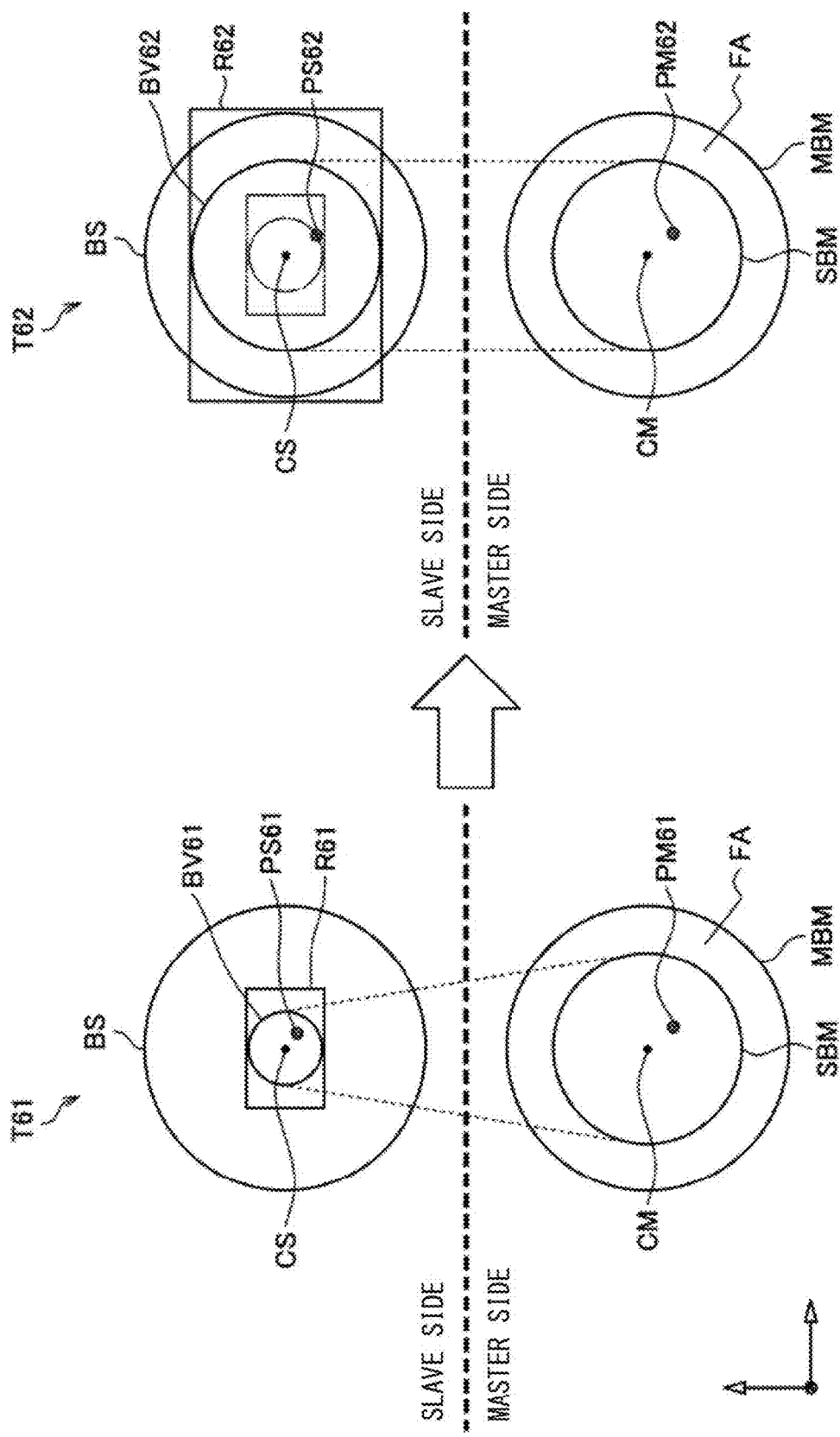
FIG. 20 is an explanatory diagram for describing a modification example 4.
Figure 21:
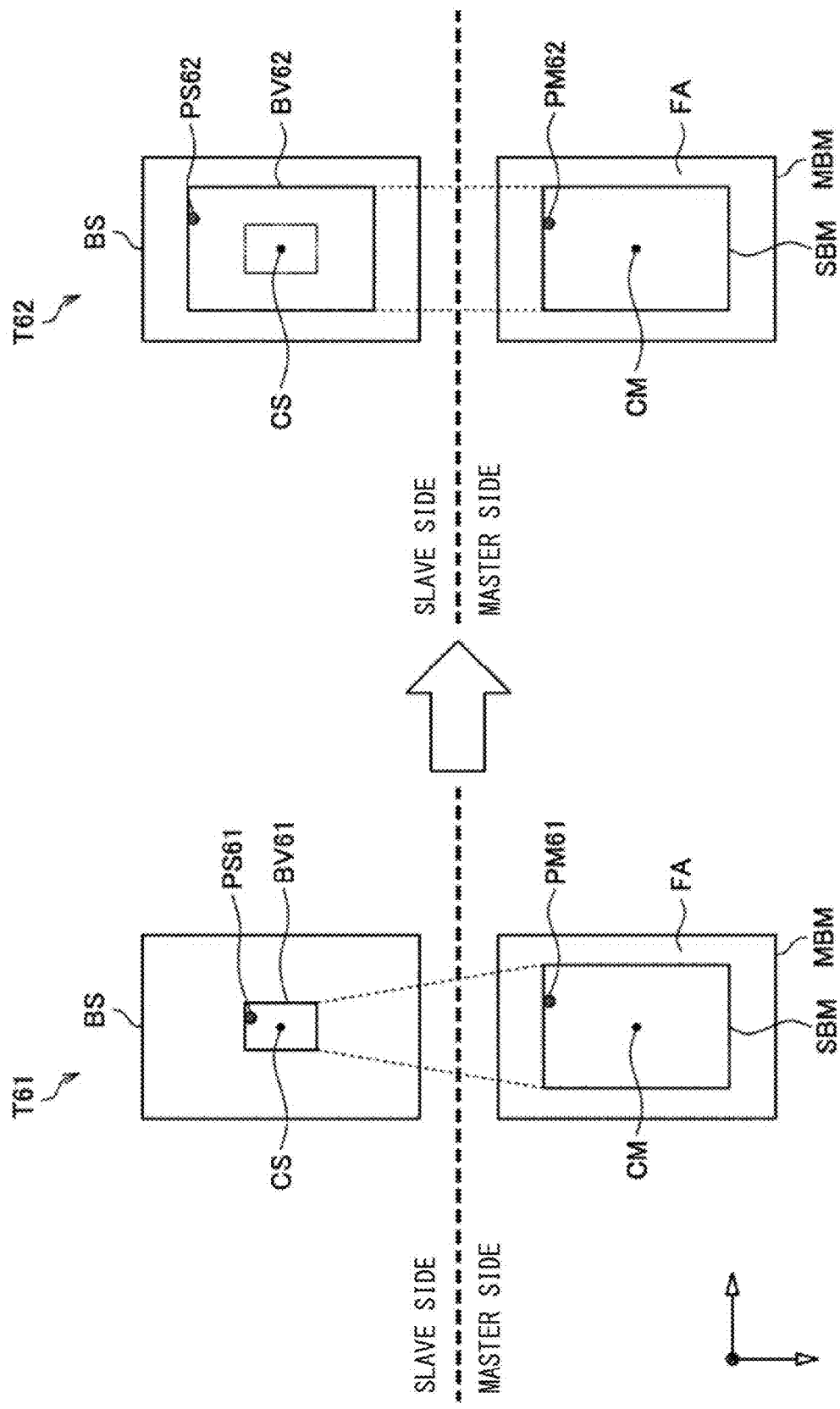
FIG. 21 is an explanatory diagram for describing the modification example 4.

First, with reference to FIGS. 20 and 21, description is given of the decrease control by the controller 530 in a case where the operation body 210 is moved upward and it is thereby detected that the master apparatus 20 has reached the movable range limit. FIG. 20 is a diagram for describing the decrease control in a case where the operation body 210 is moved upward and it is thereby detected that the master apparatus 20 has reached the movable range limit. FIG. 21 is a diagram in a case where FIG. 20 is viewed from a Y-axis direction.

FIGS. 20 and 21 illustrate the center CM of the software movable range of the operation body 210 of the master apparatus 20, the mechanical boundary MBM of the movable range of the master apparatus 20, the software boundary SMB, and the feedback region FA. In addition, FIG. 21 illustrates the center CS of the movable range of the contact section 112 included in the slave apparatus 10 and the boundary BS of the movable range of the contact section 112. It is to be noted that the following describes an example in which it is detected that the master apparatus 20 has reached the movable range limit in a case where the position of the front end of the operation body 210 is in contact with the software boundary SBM.

As described above, the control apparatus 50 may control the slave apparatus 10 to move the contact section 112 of the slave apparatus 10 to a position corresponding to the master position on the basis of the operation magnification and the operation offset. In the example illustrated in FIGS. 20 and 21, the operation magnification may be controlled by the control apparatus 50 without changing the operation offset. In the example illustrated in FIGS. 20 and 21, the operation offset is 0; however, a state in which the operation offset is added in advance may be adopted. The size of the operation region of the slave apparatus 10 corresponding to the movable range of the master apparatus 20 may be then changed in accordance with control of the operation magnification.

In a state T61 illustrated in FIGS. 20 and 21, the boundary of the operation region of the slave apparatus 10 corresponding to the movable range of the master apparatus 20 is a boundary BV61. In addition, the center of the operation region in the state T61 coincides with the center CS of the movable range of the contact section 112.

In addition, FIG. 20 also illustrates an imaging range of which an image is captured by the imaging unit 32 of the imaging apparatus 30. In the example illustrated in FIGS. 20 and 21, an imaging range R61 in the state T61 includes the entire operation region of the slave apparatus 10. In addition, in the example illustrated in FIGS. 20 and 21, a center of the imaging range R61 coincides with the center CS of the movable range of the contact section 112 and the center of the operation region.

In addition, the operation body 210 of the master apparatus 20 is movable in the movable range inside the software boundary SBM, and the position of the operation body 210 in the state T61 is indicated as a master position PM61. In addition, in the state T61, the slave apparatus 10 is controlled to move the position of the contact section 112 of the slave apparatus 10 to a slave position PS61 corresponding to the master position PM61.

As illustrated in FIG. 21, the master position PM61 in the state T61 is in contact with the software boundary SBM; therefore, the operation body 210 has reached the movable range limit. In the state T61 in FIG. 21, the operation body 210 has reached the movable range limit; therefore, the slave position PS61 is in contact with the boundary BV61 of the operation region of the slave apparatus 10 corresponding to the movable range of the master apparatus 20. Accordingly, in a case where it is detected that the master apparatus 20 has reached the movable range limit, the controller 530 performs the decrease control for decreasing both the operation magnification and the image magnification.

In the example illustrated in FIGS. 20 and 21, transition from the state T61 to a state T62 takes place by the decrease control by the controller 530. It is to be noted that FIGS. 20 and 21 illustrate an example in which the user does not move the master position from the state T61 to the state T62, and the master position PM61 in the state T61 is the same as a master position PM62 in the state T62.

In the state T62, the operation region of the slave apparatus 10 corresponding to the movable range of the master apparatus 20 is larger than the operation region in the state T61, and a boundary BV62 of the operation region in the state T62 exists outside the boundary BV61 in the state T61. It is to be noted that in the example illustrated in FIGS. 20 and 21, in transition from the state T61 to the state T62, the operation offset is not changed; therefore, the center of the operation region in the state T62 also coincides with the center CS of the movable range of the contact section 112.

As described above, the control apparatus 50 according to the present modification example controls the slave apparatus 10 to maintain a relationship between the master position in the movable range of the master apparatus 20 and the slave position in the operation region calculated from the operation magnification and the operation offset of the slave apparatus 10 while performing the decrease control. Accordingly, a slave position PS62 in the state T62 is moved to a position different from the slave position PS61 in the state T61 in accordance with enlargement of the operation region. Specifically, the slave position PS62 in the state T62 is moved in a direction away from the center of the operation region in the state T61 of the contact section 112 (the center CS of the movable range of the contact section 112). Such a moving direction corresponds to a direction from the center CM of the movable range of the master apparatus 20 to the master position PM62; therefore, such control is considered to be control that gives less discomfort to the user and reflects an intention of the user.

In addition, as described above, the control apparatus 50 according to the present modification example controls the image magnification together with the operation magnification. An imaging range R62 in the state T62 is larger than the imaging range R61 in the state T61. As described above, the control apparatus 50 according to the present modification example performs the decrease control to cause the change rate of the operation magnification and the change rate of the image magnification to be substantially the same as each other; therefore, even in the state T62, the imaging range R62 includes the entire operation region of the slave apparatus 10. It is to be noted that in the example illustrated in FIGS. 20 and 21, the image offset is not changed in transition from the state T61 to the state T62; therefore, the center of the imaging range R62 in the state T62 also coincides with the center CS of the movable range of the contact section 112 and the center of the operation region. With such a configuration, the user does not lose track of the slave position PS62 (that is, the contact section 112 of the slave apparatus 10) while performing the decrease control.

4-4-2. Increase Control and Offset Control After Decrease Control

Figure 22:
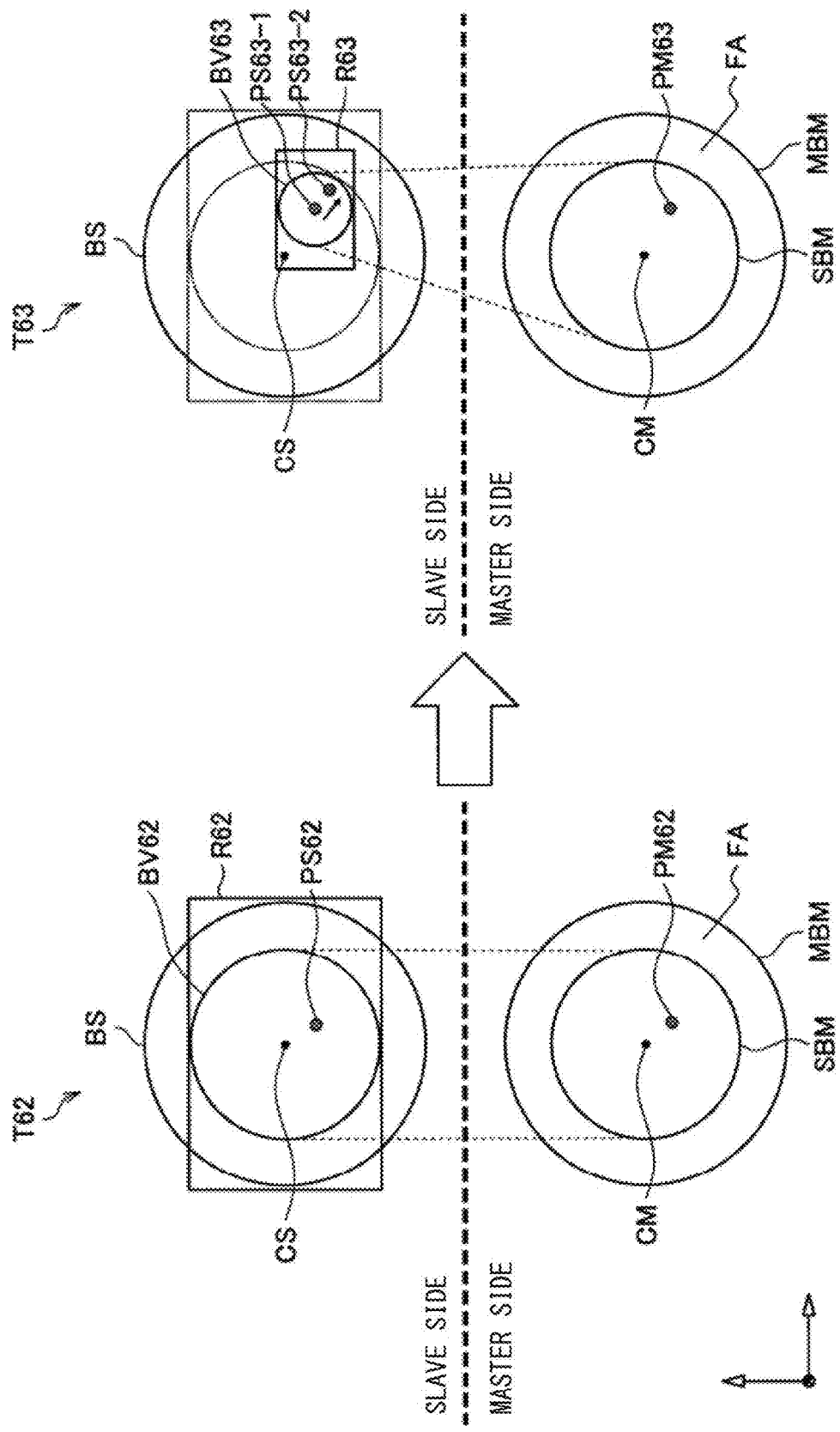
FIG. 22 is an explanatory diagram for describing the modification example 4.
Figure 23:
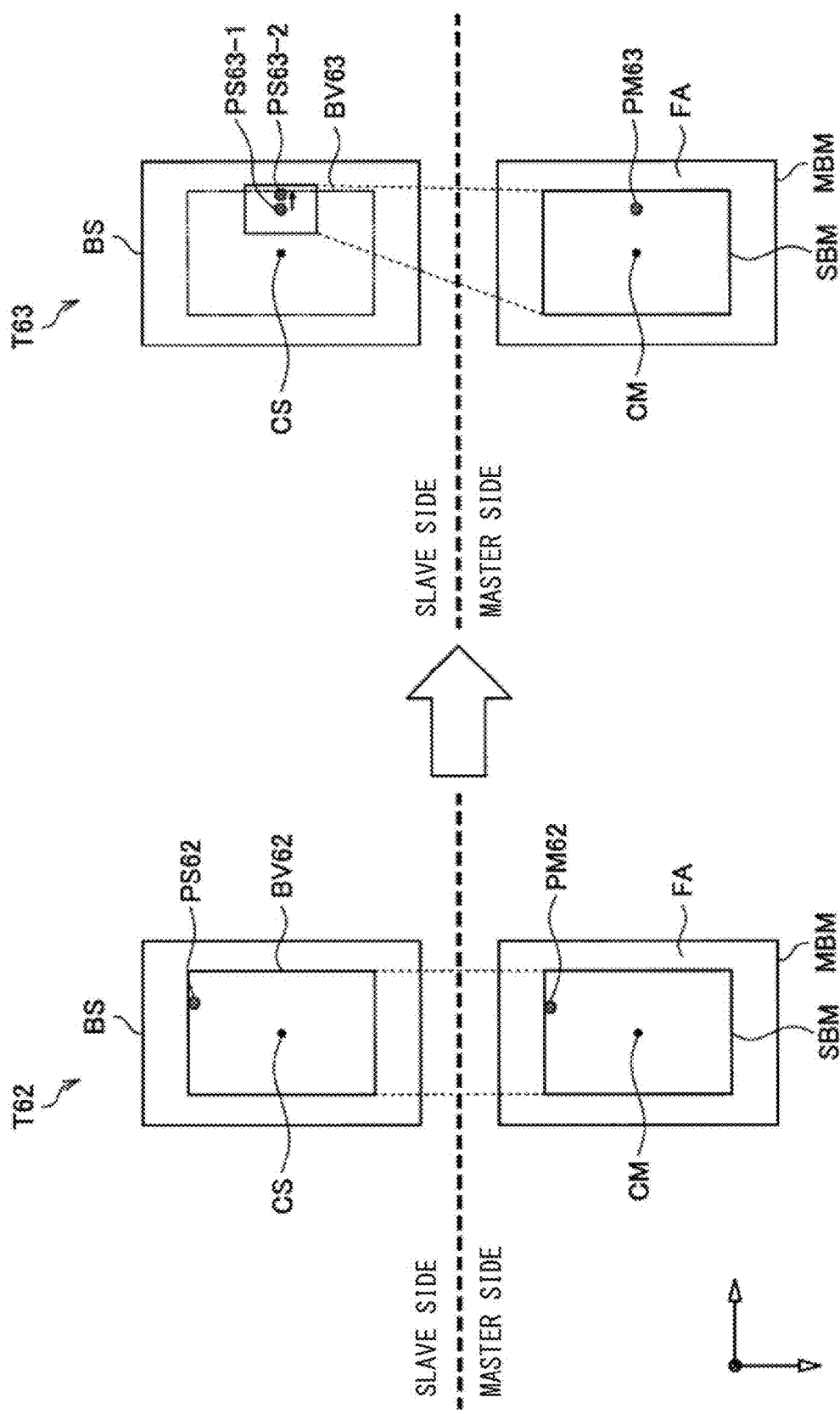
FIG. 23 is an explanatory diagram for describing the modification example 4.

Next, description is given of the increase control and the offset control by the controller 530 in a case where the operation of the operation body 210 and the increasing operation are performed after the decrease control with reference to FIGS. 22 and 23. FIG. 22 is a diagram for describing the increase control and the offset control in a case where the operation of the operation body 210 and the increasing operation are performed after the decrease control in a case where the operation body 210 is moved upward and it is thereby detected that the master apparatus 20 has reached the movable range limit. FIG. 23 is a diagram in a case where FIG. 22 is viewed from the Y-axis direction. It is to be noted that, of components illustrated in FIGS. 22 and 23, the same components as those described with reference to FIGS. 20 and 21 are denoted by the same reference numerals, and thus redundant description thereof is omitted. In addition, the state T62 illustrated in FIGS. 22 and 23 indicates the same state as the state T62 illustrated in FIGS. 20 and 21.

In the example illustrated in FIGS. 22 and 23, transition from the state T62 to a state T63 takes place by the operation of the operation body 210 and the increasing operation by the user. For example, the user first operates the operation body 210 to move the master position. Specifically, the user moves the operation body 210 in an X-axis direction and a Z-axis direction to move the master position from the master position PM62 in the state T62 to a master position PM63 in the state T63. The slave position of the slave apparatus 10 is moved from the slave position PS62 in the state T62 to a slave position PS63-1 in the state T63 with movement of the master position.

After the movement of the master position, the user inputs the increasing operation to the master apparatus 20. The user operates, for example, a foot pedal to input the increasing operation to the master apparatus 20. In a case where the increasing operation is inputted by the user, the controller 530 performs the increase control for increasing both the operation magnification and the image magnification. It is to be noted that the increasing operation may be automatically performed by the controller 530. For example, the controller 530 may perform the increase control when it is detected that the user stops movement of the operation body 210.

Further, the controller 530 further performs control of an offset corresponding to the slave position of the slave apparatus while performing the increase control. For example, as with the first embodiment described above, it is assumed that the master-slave system 1000 includes one slave apparatus 10 and one master apparatus 20. In this case, the controller 530 sets the operation offset to cause the position of a front end of the slave apparatus 10 (for example, the front end of the contact section 112) and the position of the center of the operation region to be the same as each other. Specifically, as illustrated in the state T63 in FIG. 22, the controller 530 sets the operation offset to cause the slave position PS63-1 and the position of a center of an operation region BV63 to be the same as each other. It is to be noted that the position of the front end of the slave apparatus 10 may be calculated from a measurement value of an encoder provided at a joint included in the slave apparatus 10, for example.

In control of the offset, the controller 530 sets the image offset to be the same as the operation offset. Specifically, as illustrated in the state T63 in FIG. 22, the controller 530 sets the image offset to cause the slave position PS63-1 and the position of a center of an imaging region R63 to be the same as each other. Accordingly, the increase control and the offset control are performed to cause the position of the front end of the slave apparatus 10 and the position of the center of the imaging range R63 to coincide with each other. With such a configuration, the user does not lose track of a slave position PS63 (that is, the contact section 112 of the slave apparatus 10) while performing the increase control.

In addition, as with the second embodiment described above, it is assumed that the master-slave system 2000 includes two slave apparatuses 10 and two master apparatuses 20. In this case, the controller 530 sets a center of each of the slave apparatus 10R and the slave apparatus 10L as the position of the operation offset. Specifically, the controller 530 sets the operation offset to cause the position of a center of a straight line joining the position of a front end of the slave apparatus 10R and the position of a front end of the slave apparatus 10L and the position of center of the operation region (the center of BV63) to be the same as each other. It is to be noted that the position of the front end of the slave apparatus 10R may be calculated from a measurement value of an encoder provided at a joint included in the slave apparatus 10R, for example. In addition, the position of the front end of the slave apparatus 10L may be calculated from a measurement value of an encoder provided at a joint included in the slave apparatus 10L, for example.

Further, the controller 530 sets the image offset to be the same as the operation offset. Accordingly, the increase control and the offset control are performed to cause the position of the center of the straight line joining the position of the front end of the slave apparatus 10R and the position of the front end of the slave apparatus 10L and the position of the center of the imaging range R63 to coincide with each other. With such a configuration, the user does not lose track of the slave position PS63 (that is, the contact section 112 of the slave apparatus 10) while performing the increase control.

A state after the increase control and the offset control is the state T63 illustrated in FIGS. 22 and 23. As illustrated in FIGS. 22 and 23, change in the operation magnification in the increase control causes the size of the operation region in the state T62 (the size of the boundary BV62) and the size of the operation region in the state T63 (the size of a boundary BV63) to be different from each other. Specifically, the operation magnification is increased by the increase control, which causes the size of the boundary BV63 to be smaller than the boundary BV62 in the state T62. Accordingly, the operation region of the slave apparatus 10 corresponding to the movable range of the master apparatus 20 in the state T63 becomes smaller than the operation region in the state T62.

In addition, as illustrated in FIGS. 22 and 23, change in the image magnification by the increase control causes the size of the imaging range R62 in the state T62 and the imaging range R63 in the state T63 to be different from each other. Specifically, the image magnification is increased by the increase control, which causes the imaging range R63 in the state T63 to be smaller than the imaging range R62 in the state T62. As described above, the control apparatus 50 according to the present modification example performs the increase control to cause the change rate of the operation magnification and the change rate of the image magnification to be substantially the same as each other; therefore, even in the state T63, the imaging range R63 includes the entire operation region of the slave apparatus 10. With such a configuration, the user does not lose track of the slave position PS63 (that is, the contact section 112 of the slave apparatus 10) while performing the increase control.

In addition, as illustrated in FIGS. 22 and 23, the operation region in the state T63 of the slave apparatus 10 corresponding to the movable range of the master apparatus 20 is moved to a position different from the operation region in the state T62 by change in the operation offset by the offset control. Specifically, the center of the operation region in the state T63 is moved in a direction from the center of the operation region (the center CS of the movable range of the contact section 112) in the state T62 toward the slave position PS63-1. In addition, similarly, the boundary BV63 of the operation region of the slave apparatus 10 corresponding to the movable range of the master apparatus 20 in the state T63 is also moved in a direction similar to the center of the operation region.

In addition, as illustrated in FIGS. 22 and 23, the imaging range R63 in the state T63 is moved to a position different from the imaging range R62 in the state T62 by change in the image offset by the offset control. As described above, in the present modification example, the image offset is controlled to cause the moving direction and the movement amount of the operation region in actual space to be substantially the same as the moving direction and the movement amount of the imaging range. Accordingly, even in the state T63, the imaging range R63 includes the entire operation region of the slave apparatus 10, and the center of the imaging range R63 in the state T63 coincides with the center of the operation region. With such a configuration, the user does not lose track of the slave position PS63 (that is, the contact section 112 of the slave apparatus 10) while performing the offset control.

It is to be noted that the controller 530 may move the position of the slave position PS63-1 of the slave apparatus 10 while performing the increase control. For example, the controller 530 moves the slave position PS63-1 to cause a positional relationship between the center of the software boundary SBM and the master position PM63 of the master apparatus 20 and a positional relationship between the center of the operation region BV63 and the slave position PS63-1 of the slave apparatus 10 to correspond to each other. Specifically, as illustrated in FIGS. 22 and 23, the controller 530 moves the slave position PS63-1 to a slave position PS63-2. With such a configuration, it is less likely to give the user discomfort regarding a positional relationship between the master position PM63 of the master apparatus 20 and the slave position PS63-2 of the slave apparatus 10 after the increase control.

4-4-3. Operation of Control Apparatus 50

Figure 24:
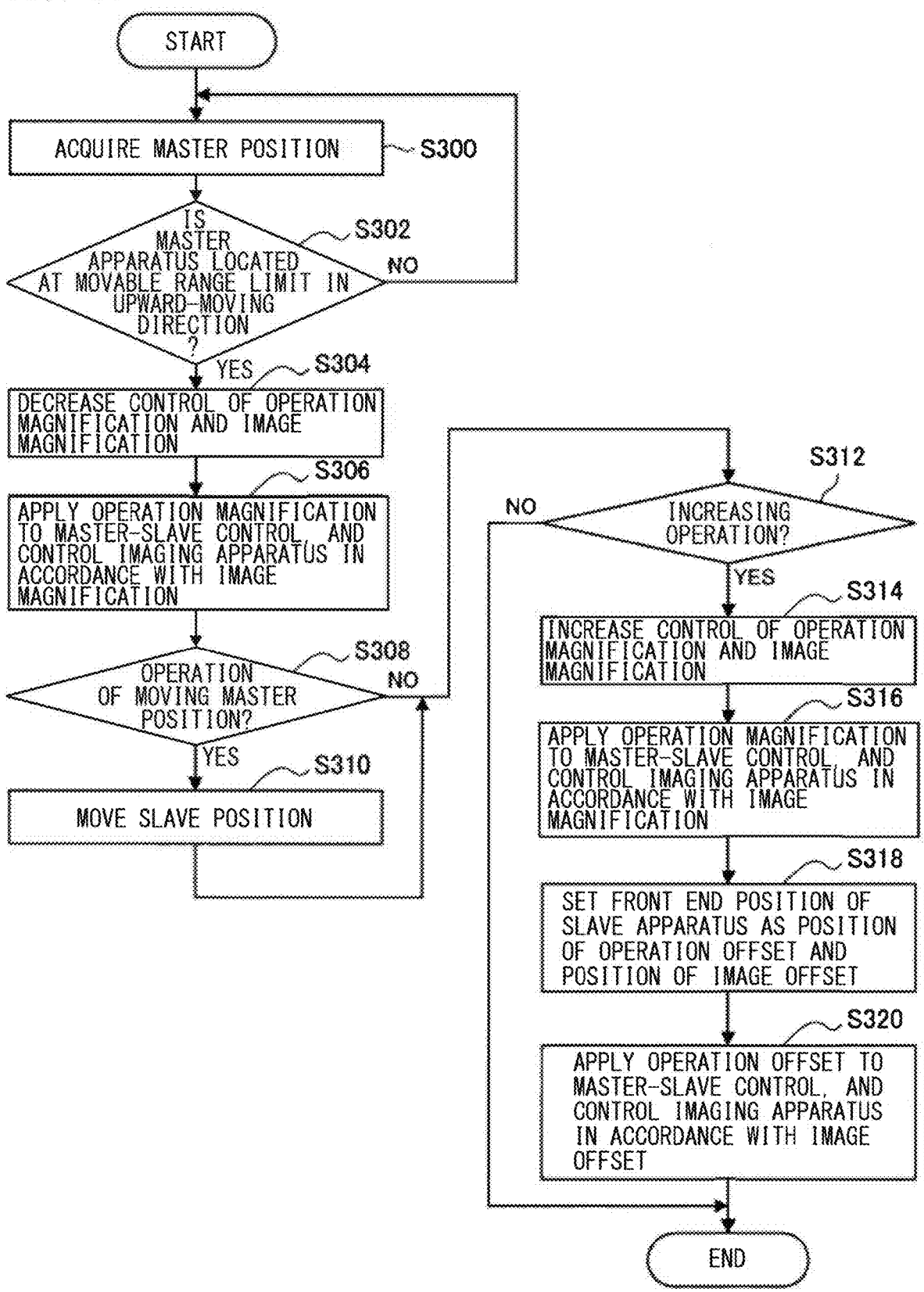
FIG. 24 is an explanatory diagram for describing the modification example 4.
Figure 25:
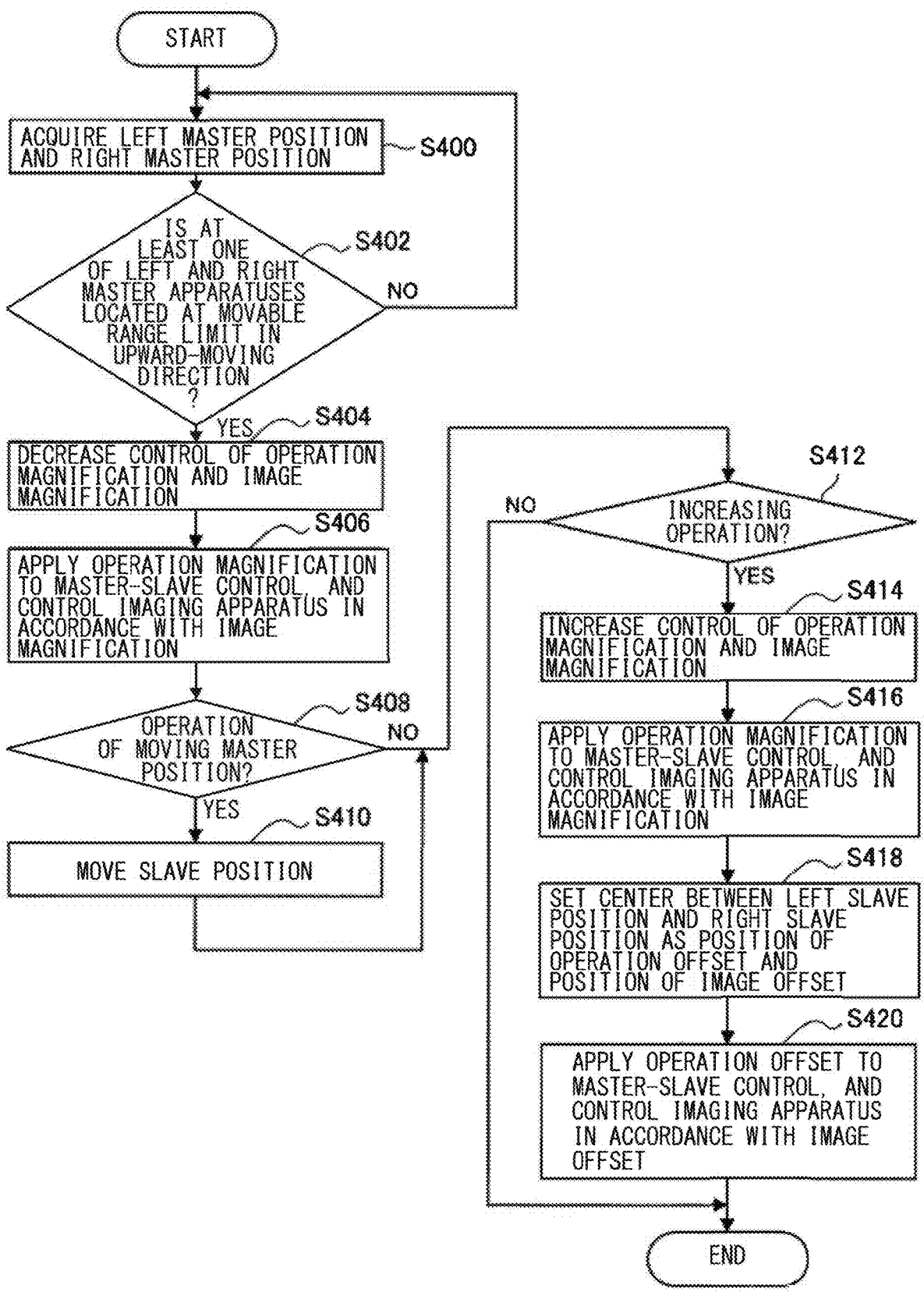
FIG. 25 is an explanatory diagram for describing the modification example 4.

Here, with reference to FIGS. 24 and 25, description is given of an operation of the control apparatus 50 in a case where detection of whether or not the movable range limit has been reached, the decrease control, the increase control, and the offset control described above are performed.

(Flow of Processing in Case of Master-Slave System 1000)

FIG. 24 is a flowchart illustrating an operation of the control apparatus 50 in the master-slave system 1000 including one slave apparatus 10 and one master apparatus 20.

Referring to FIG. 24, the master position is first acquired (S300). It is to be noted that information about the master position may be transmitted from the master apparatus 20 to the control apparatus 50, or may be specified on the basis of information from the master apparatus 20 received by the communication unit 510.

Next, the controller 530 determines whether or not it is detected that the master apparatus 20 has reached the movable range limit in the upward-moving direction of the operation body 210 (S302). In a case where it is not detected that the master apparatus 20 has reached the movable range limit (NO in S302), acquirement of the master position (S300) and detection of whether or not the movable range limit has been reached (S302) are repeated.

In contrast, in a case where it is detected that the master apparatus 20 has reached the movable range limit (YES in S302), the magnification controller 531 of the controller 530 performs the decrease control of the operation magnification and the image magnification (S304). The master-slave controller 535 of the controller 530 then applies the operation magnification to the master-slave control, and the imaging controller 537 of the controller 530 controls the imaging apparatus 30 in accordance with the image magnification (S306).

After control of the imaging apparatus 30, the controller 530 determines whether or not an operation of moving the master position by the user is performed (S308). In a case where the operation of moving the master position by the user is not performed (NO in S308), the controller 530 determines whether or not the increasing operation by the user is performed (S312).

In contrast, in a case where the operation of moving the master position by the user is performed (YES in S308), the master-slave controller 535 of the controller 530 moves the slave position of the slave apparatus 10 in accordance with the master position (S310). Thereafter, the controller 530 determines whether or not the increasing operation by the user is performed (S312).

In a case where the increasing operation is not performed (NO in S312), the processing ends. In contrast, in a case where the increasing operation is performed (YES in S312), the magnification controller 531 of the controller 530 performs the increase control of the operation magnification and the image magnification (S314). Next, the master-slave controller 535 of the controller 530 applies the operation magnification to the master-slave control, and the imaging controller 537 of the controller 530 controls the imaging apparatus 30 in accordance with the image magnification (S316). Next, the offset controller 533 of the controller 530 sets the front end position of the slave apparatus 10 as the position of the operation offset and the position of the image offset (S318). Thereafter, the master-slave controller 535 applies the operation offset to the master-slave control, and the imaging controller 537 controls the imaging apparatus 30 in accordance with the image offset (S320).

(Flow of Processing in Case of Master-Slave System 2000)

FIG. 25 is a flowchart illustrating an operation of the control apparatus 50 in the master-slave system 2000 including two slave apparatuses 10 and two master apparatuses 20.

Referring to FIG. 25, the left master position and the right master position are first acquired (S400). Next, the controller 530 determines whether or not it is detected that at least one of the master apparatus 20R or the master apparatus 20L has reached the movable range limit in the upward-moving direction, on the basis of the left master position and the right master position (S402).

In a case where it is not detected that the movable range limit has not been reached (NO in S402), acquirement of the left master position and the right master position (S400) and detection of whether or not the movable range limit has been reached (S402) are repeated.

In contrast, in a case where it is detected that the movable range limit has been reached (YES in S402), the magnification controller 531 of the controller 530 performs the decrease control of the operation magnification and the image magnification (S404). Thereafter, the master-slave controller 535 of the controller 530 applies the operation magnification to the master-slave control, and the imaging controller 537 of the controller 530 controls the imaging apparatus 30 in accordance with the image magnification (S406).

After control of the imaging apparatus 30, the controller 530 determines whether or not the operation of moving the master position by the user is performed (S408). In a case where the operation of moving the master position by the user is not performed (NO in S408), the controller 530 determines whether or not the increasing operation by the user is performed (S412).

In contrast, in a case where the operation of moving the master position by the user is performed (YES in S408), the master-slave controller 535 of the controller 530 moves the slave position of the slave apparatus 10 in accordance with the master position (S410). Thereafter, the controller 530 determines whether or not the increasing operation by the user is performed (S412).

In a case where the increasing operation is not performed (NO in S412), the processing ends. In contrast, in a case where the increasing operation is performed (YES in S412), the magnification controller 531 of the controller 530 performs the increase control of the operation magnification and the image magnification (S414). Next, the master-slave controller 535 of the controller 530 applies the operation magnification to the master-slave control, and the imaging controller 537 of the controller 530 controls the imaging apparatus 30 in accordance with the image magnification (S416). Next, the offset controller 533 of the controller 530 sets the position of a center of a straight line joining the left slave position and the right slave position as the position of the operation offset and the position of the image offset (S418). Thereafter, the master-slave controller 535 applies the operation offset to the master-slave control, and the imaging controller 537 controls the imaging apparatus 30 in accordance with the image offset (S420).

<4-5. Modification Example 5>

In the modification example 4 described above, description has been given of an example in which the control apparatus 50 performs processing until the increase control and the offset control in order of detection of whether or not the movable range limit has been reached, the decrease control, the increase control, and the offset control; however, the present technology is not limited to the example. In a case where after the increase control and the offset control, it is detected that the master apparatus 20 has reached the movable range limit, the control apparatus 50 may perform the decrease control again.

The following describes control by the controller 530 in performing the decrease control again in a case where after the increase control and the offset control, it is detected that the master apparatus 20 has reached the movable range limit. Specifically, description is given of the decrease control in a case where the operation body 210 is moved upward and it is thereby detected that the master apparatus 20 has reached the movable range limit.

Figure 26:
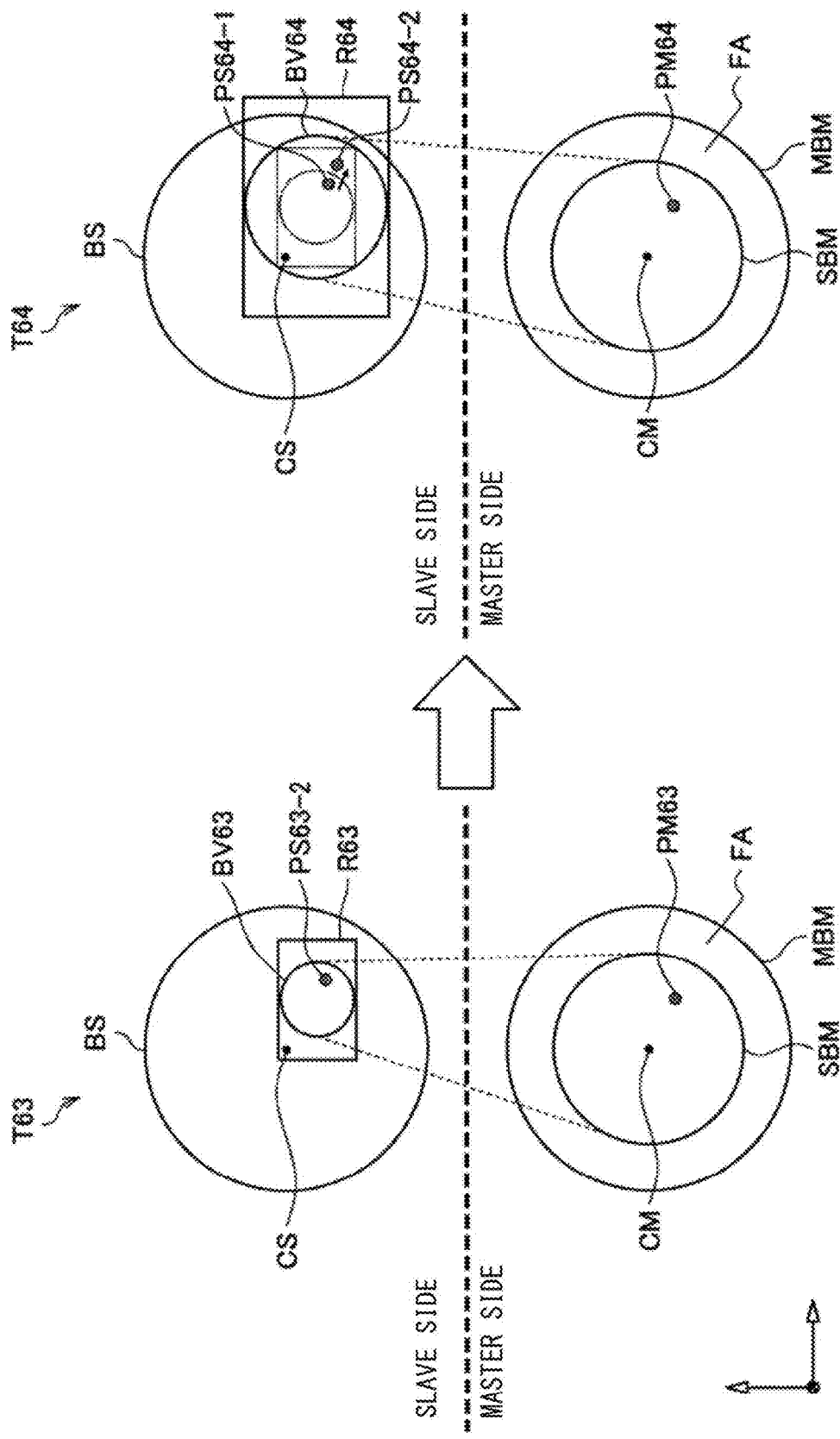
FIG. 26 is an explanatory diagram for describing a modification example 5.

FIG. 26 is a diagram for describing the decrease control in a case where after the increase control, the operation body 210 is moved upward and it is thereby detected that the master apparatus 20 has reached the movable range limit. FIG. 27 is a diagram in a case where FIG. 26 is viewed from the Y-axis direction. It is to be noted that, of components illustrated in FIGS. 26 and 27, the same components as those described with reference to FIGS. 20 to 23 are denoted by the same reference numerals, and thus redundant description thereof is omitted. In addition, the state T63 illustrated in FIGS. 26 and 27 indicates the same state as the state T63 illustrated in FIGS. 22 and 23.

In the example illustrated in FIGS. 26 and 27, transition from the state T63 to a state T64 takes place by the decrease control in a case where after the increase control and the offset control, the operation body 210 is moved upward and it is thereby detected that the master apparatus 20 has reached the movable range limit. For example, the user performs the operation of moving the operation body 210 upward after the increase control and the offset control by the controller 530. Specifically, the user moves the operation body 210 upward in a Z direction to move the master position from the master position PM63 in the state T63 to a master position PM64 in the state T64. The slave position of the slave apparatus 10 is moved from the slave position PS63-2 in the state T63 to a slave position PS64-1 in the state T64 with movement of the master position.

As illustrated in FIGS. 26 and 27, the master position PM64 in the state T64 is in contact with the software boundary SBM; therefore, the operation body 210 has reached the movable range limit. In the state T64 in FIG. 27, the operation body 210 has reached the movable range limit; therefore, the slave position PS64-1 is in contact with a boundary BV64 of the operation region of the slave apparatus 10 corresponding to the movable range of the master apparatus 20. In a case where it is detected that the master apparatus 20 has reached the movable range limit in such a manner, the controller 530 performs the decrease control for decreasing both the operation magnification and the image magnification.

A state after the decrease control is the state T64 illustrated in FIGS. 26 and 27. As illustrated in FIGS. 26 and 27, change in the operation magnification by the decrease control causes the size of the operation region in the state T63 (the size of the boundary BV63) and the size of the operation region in the state T64 (the size of the boundary BV64) to be different from each other. Specifically, the operation magnification is decreased by the decrease control, which causes the size of the boundary BV64 to be larger than the boundary BV63 in the state T63. Accordingly, the operation region of the slave apparatus 10 corresponding to the movable range of the master apparatus 20 in the state T64 becomes larger than the operation region in the state T63.

In addition, as illustrated in FIGS. 26 and 27, change in the image magnification by the decrease control causes the size of the imaging range R63 in the state T63 and the size of an imaging range R64 in the state T64 to be different from each other. Specifically, the image magnification is decreased by the increase control, which causes the imaging range R64 in the state T64 to be larger than the imaging range R63 in the state T63. As described above, the control apparatus 50 according to the present modification example performs the increase control to cause the change rate of the operation magnification and the change rate of the image magnification to be substantially the same as each other; therefore, even in the state T64, the imaging range R64 includes the entire operation region of the slave apparatus 10. With such a configuration, the user does not lose track of a slave position PS64 (that is, the contact section 112 of the slave apparatus 10) while performing the decrease control.

It is to be noted that as with the example illustrated in FIGS. 26 and 27, the control apparatus 50 may not change the operation offset in the offset control. In a case where the operation offset is not changed, the operation region in the state T64 of the slave apparatus 10 corresponding to the movable range of the master apparatus 20 remains at the same position as the operation region in the state T63. Specifically, the center of the operation region in the state T64 remains at the same position as the center of the operation region in the state T63. In addition, similarly, the center of the boundary BV64 of the operation region of the slave apparatus 10 corresponding to the movable range of the master apparatus 20 in the state T64 remains at the same position as the center of the boundary BV63 of the operation region in the state T63.

It is to be noted that in a case where the decrease control is performed in a state in which the operation offset in the offset control is not changed, the boundary BV64 of the operation region of the slave apparatus 10 may extend off the boundary BS of the movable range of the slave apparatus 10. Accordingly, the control apparatus 50 calculates the operation magnification and the image magnification and performs the decrease control to prevent the boundary BV64 of the operation region of the slave apparatus 10 from extending off the boundary BS of the movable range of the slave apparatus 10.

In addition, as with the example illustrated in FIGS. 26 and 27, the control apparatus 50 may not change the image offset in the offset control. In a case where the image offset is not changed, the imaging range R64 in the state T64 remains at the same position as the imaging range R63 in the state T63. As described above, in the present modification example, the image offset is controlled to cause the moving direction and the movement amount of the operation region in actual space to be substantially the same as the moving direction and the movement amount of the imaging range. Accordingly, even in the state T64, the imaging range R64 includes the entire operation region of the slave apparatus 10, and the center of the imaging range R64 in the state T64 coincides with the center of the operation region. With such a configuration, the user does not lose track of the slave position PS64 (that is, the contact section 112 of the slave apparatus 10) while performing the offset control.

It is to be noted that the controller 530 may move the position of the slave position PS64-1 of the slave apparatus 10 while performing the decrease control. For example, the controller 530 moves the slave position PS64-1 to cause a positional relationship between the center of the software boundary SBM and the master position PM64 of the master apparatus 20 and a positional relationship between the center of the operation region BV64 and the slave position PS64-1 of the slave apparatus 10 to correspond to each other. Specifically, as illustrated in FIGS. 26 and 27, the controller 530 moves the slave position PS64-1 to a slave position PS64-2. With such a configuration, it is less likely to give the user discomfort regarding a positional relationship between the master position PM64 of the master apparatus 20 and the slave position PS64-2 of the slave apparatus 10 after the increase control.

It is to be noted that in a case where after the increase control and the offset control, it is detected that the master apparatus 20 has reached the movable range limit, the control apparatus 50 may perform the offset control in addition to the decrease control. For example, the control apparatus 50 performs the decrease control and the offset control to restore a state before the increase control and the offset control to the same state.

As one example, there is an example in which the control apparatus 50 performs the decrease control and the offset control to restore the state T63 that is a state after the increase control and the offset control illustrated in FIGS. 22 and 23 to the same state as the state T62 that is the state before the increase control and the offset control. Specifically, the controller 530 performs the decrease control for changing the operation magnification and the image magnification to cause the sizes of the operation region and the imaging range after the decrease control to be respectively the same as the sizes of the operation region (a region inside the boundary BV62) and the imaging range R62 in the state T62. In addition, the controller 530 performs the offset control for changing the operation offset and the image offset to cause the positions of the centers of the operation region and the imaging range after the offset control to be the same as the positions of the centers of the operation region (the region inside the boundary BV62) and the imaging range R62 in the state T62. Such a configuration makes it possible for the control apparatus 50 to restore the state to the same state as the state before the increase control and the offset control.

5. Hardware Configuration Example

The embodiments of the present disclosure have been described above. Finally, a hardware configuration according to an embodiment of the present disclosure is described with reference to FIG. 28. FIG. 28 is a block diagram illustrating an example of a hardware configuration of the control apparatus 50 according to the embodiment of the present disclosure. Information processing by the control apparatus 50 according to the embodiment of the present disclosure is achieved in cooperation between software and hardware described below.

As illustrated in FIG. 28, the control apparatus 50 includes a CPU (Central Processing Unit) 901, a ROM (Read Only Memory) 902, a RAM (Random Access Memory) 903, and a host bus 904a. In addition, the control apparatus 50 includes a bridge 90, an external bus 904b, an interface 905, an input apparatus 906, an output apparatus 907, a storage apparatus 908, a drive 909, a coupling port 911, and a communication apparatus 913. The control apparatus 50 may include a processing circuit such as a DSP or an ASIC instead of or together with the CPU 901.

The CPU 901 functions as an arithmetic processing apparatus and a control apparatus, and controls an overall operation of the control apparatus 50 in accordance with various programs. In addition, the CPU 901 may be a microprocessor. The ROM 902 stores programs, arithmetic parameters, and the like to be used by the CPU 901. The RAM 903 temporarily stores programs used in execution of the CPU 901, parameters appropriately changed in the execution, and the like. The CPU 901 may form the detector 520 and the controller 530, for example.

The CPU 901, the ROM 902, and the RAM 903 are coupled to each other by the host bus 904a including a CPU bus or the like. The host bus 904a is coupled to the external bus 904b such as a PCI (Peripheral Component Interconnect/Interface) bus via the bridge 904. It is to be noted that the host bus 904a, the bridge 904, and the external bus 904b do not necessarily have to be separately included, and the functions thereof may be implemented in a single bus.

The input apparatus 906 is achieved by an apparatus through which a user inputs information, such as a mouse, a keyboard, a touch panel, a button, a microphone, a switch, and a lever, for example. In addition, the input apparatus 906 may be a remote control apparatus using infrared rays or other electric waves, or an external coupling apparatus such as a mobile phone or a PDA supporting an operation of the control apparatus 50, for example. Further, the input apparatus 906 may include an input control circuit or the like that generates an input signal on the basis of information inputted by the user using an input means described above and outputs the generated input signal to the CPU 901, for example. The user of the control apparatus 50 operates the input apparatus 906, which makes it possible to input various kinds of data to the control apparatus 50, or instruct the control apparatus 50 to perform a processing operation.

The output apparatus 907 includes an apparatus that is able to visually or aurally notify a user of acquired information. Examples of such an apparatus include a display apparatus such as a CRT display apparatus, a liquid crystal display apparatus, a plasma display apparatus, an EL display apparatus and a lamp, an audio output apparatus such as a speaker and headphones, a printer apparatus, and the like. The output apparatus 907 outputs results acquired through various kinds of processing performed by the control apparatus 50, for example. Specifically, the display apparatus visually displays results acquired through various kinds of processing performed by the control apparatus 50, in various forms such as text, images, tables, and graphs. Meanwhile, the audio output apparatus converts audio signals including reproduced audio data, acoustic data, and the like into analog signals, and aurally outputs the analog signals.

The storage apparatus 908 is an apparatus for data storage that is formed as an example of a storage unit of the control apparatus 50. For example, the storage apparatus 908 is achieved by a magnetic storage unit device such as HDD, a semiconductor storage device, an optical storage device, a magneto-optical storage device, or the like. The storage apparatus 908 may include a storage medium, a recording apparatus that records data in the storage medium, a reading apparatus that reads out data from the storage medium, a deletion apparatus that deletes data recorded in the storage medium, and the like. This storage apparatus 908 stores a program to be executed by the CPU 901, various kinds of data, various kinds of data acquired from the outside, and the like.

The drive 909 is a reader/writer for a storage medium, and is incorporated in or externally attached to the control apparatus 50. The drive 909 reads out information recorded in a removable storage medium such as a magnetic disk, an optical disk, a magneto-optical disk, or a semiconductor memory mounted thereon, and outputs the information to the RAM 903. In addition, the drive 909 is also able to write information into the removable storage medium.

The coupling port 911 is an interface coupled to an external device, and is a coupling port to an external device that is able to transmit data through a USB (Universal Serial Bus) or the like, for example.

The communication apparatus 913 is a communication interface including, for example, a communication device or the like for coupling to a network 920. Examples of the communication apparatus 913 include a communication card and the like for wired or wireless LAN (Local Area Network), LTE (Long Term Evolution), Bluetooth (registered trademark), or WUSB (Wireless USB). In addition, the communication apparatus 913 may be a router for optical communication, a router for ADSL (Asymmetric Digital Subscriber Line), a modem for various kinds of communication, or the like. For example, this communication apparatus 913 is able to transmit and receive signals and the like to and from the Internet and another communication device in accordance with a predetermined protocol such as TCP/IP, for example. The communication apparatus 913 may form the communication unit 510, for example.

It is to be noted that the network 920 is a wired or wireless transmission path for information transmitted from an apparatus coupled to the network 920. For example, the network 920 may include a public network such as the Internet, a telephone network, or a satellite communication network, and various LANs (Local Area Networks) including Ethernet (registered trademark), WAN (Wide Area Network), and the like. In addition, the network 920 may include a private network such as IP-VPN (Internet Protocol-Virtual Private Network).

The above has described an example of the hardware configuration that makes it possible to achieve the function of the control apparatus 50 according to the embodiment of the present disclosure. The respective components described above may be achieved by using general-purpose members, or may be achieved by hardware specific to the functions of the respective components. It is thus possible to appropriately change hardware configurations to be utilized in accordance with a technical level at the time of carrying out the embodiment of the present disclosure.

It is to be noted that it is possible to create a computer program for achieving each function of the control apparatus 50 according to the embodiment of the present disclosure as described above and install the computer program in a PC or the like. In addition, it is also possible to provide a computer-readable recording medium having such a computer program stored therein. The recording medium is, for example, a magnetic disk, an optical disk, a magneto-optical disk, a flash memory, or the like. In addition, the computer program described above may be distributed, for example, via a network without using a recording medium.

6. Conclusion

As described above, according to the embodiments of the present disclosure, it is possible to further reduce a burden on a user performing an operation of the master-slave system.

A preferred embodiment(s) of the present disclosure has/have been described above in detail with reference to the accompanying drawings, but the technical scope of the present disclosure is not limited to such an embodiment(s). A person skilled in the art may find various alterations and modifications within the scope of the appended claims, and it should be understood that they will naturally come under the technical scope of the present disclosure.

For example, in the embodiments described above, an example in which the button for the increasing operation or the operation of switching the control mode are included in the display image displayed on the display apparatus 40 has been described; however, the present technology is not limited to the example. For example, as long as the user knows a position for such an operation, the button may not be displayed. Alternatively, the button may be translucently displayed.

In addition, in the embodiments described above, an example in which the increasing operation and the operation of switching the control mode are operations on the basis of an input to the master apparatus 20 by the user has been described; however, the present technology is not limited to the example. The increasing operation and the operation of switching the control mode may be operations using any other input device such as a foot pedal.

In addition, in a case where an obstacle exists at a destination of the imaging unit 32 or a destination of the slave position, movement of the imaging unit 32 or movement of the slave position may be controlled to avoid the obstacle.

In addition, the effects described herein are merely illustrative and exemplary, and not limitative. That is, the technology according to the present disclosure may exert other effects that are apparent to those skilled in the art from the description herein, in addition to the effects described above or in place of the effects described above.

It is to be noted that the following configurations also fall within the technical scope of the present disclosure.

(1)

A control apparatus including:
  a detector that detects whether or not a master apparatus used for an operation of a slave apparatus is located at a movable range limit; and
  a controller that controls, on the basis of a detection result, a slave parameter related to control of the slave apparatus and an image parameter related to an image displayed on the basis of imaging.

(2)

The control apparatus according to (1), in which
  the slave parameter includes an operation magnification indicating a ratio of a movement amount for the slave apparatus to a movement amount for the master apparatus,
  the image parameter includes an image magnification indicating a magnification related to the image, and
  the controller controls the operation magnification and the image magnification substantially simultaneously.

(3)
The control apparatus according to (2), in which the controller controls the operation magnification and the image magnification to cause a change rate of the operation magnification and a change rate of the image magnification to be substantially the same as each other.
(4)
The control apparatus according to (2) or (3), in which the controller performs decrease control for decreasing the operation magnification and the image magnification in a case where it is detected that the master apparatus is located at the movable range limit.
(5)
The control apparatus according to (4), in which the controller continuously performs the decrease control while it is detected that the master apparatus is located at the movable range limit.
(6)
The control apparatus according to (4), in which the controller performs the decrease control in a case where it is detected that the master apparatus has reached one region of a boundary of a movable range of the master apparatus existing in a direction corresponding to a direction away from a contact target.
(7)
The control apparatus according to any one of (2) to (4), in which the controller performs increase control for increasing the operation magnification and the image magnification in accordance with a predetermined increasing operation.
(8)
The control apparatus according to (7), in which the controller further performs control of an offset corresponding to a position of the slave apparatus while performing the increase control.
(9)
The control apparatus according to (7), in which the increasing operation includes an operation on the basis of an input to the master apparatus by a user.
(10)
The control apparatus according to any one of (1) to (9), in which
the slave parameter includes an operation offset indicating an offset distance from a point in the slave apparatus corresponding to an origin point in the master apparatus to an origin point in the slave apparatus,
the image parameter includes an image offset indicating an offset of the image, and
the controller controls the operation offset and the image offset substantially simultaneously.
(11)
The control apparatus according to (10), in which the controller controls the operation offset and the image offset to cause a moving direction and a movement amount of a slave apparatus corresponding to a movable range of the master apparatus in actual space to be substantially the same as a moving direction and a movement amount of a display range on the image.
(12)
The control apparatus according to (10) or (11), in which the controller controls the operation offset and the image offset in a case where it is detected that the master apparatus is located at the movable range limit.
(13)
The control apparatus according to (12), in which the controller continuously performs control of the operation offset and the image offset while it is detected that the master apparatus is located at the movable range limit.
(14)
The control apparatus according to any one of (1) to (13), in which
a movable range of the master apparatus includes a first movable range and a second movable range, the first movable range being a region where the master apparatus is physically operable, and the second movable range being a region that is smaller than the first movable range and exists inside the first movable range, and
in a case where the master apparatus is located in a region between the first movable range and the second movable range, the detector detects that the master apparatus is located at the movable range limit.
(15)
The control apparatus according to (14), in which in a case where it is detected that the master apparatus is located at the movable range limit, the controller moves the master apparatus into the second movable range.
(16)
The control apparatus according to any one of (1) to (15), in which the controller performs control of the slave parameter and the image parameter to cause a center of an operation region of the slave apparatus corresponding to a movable range of the master apparatus to coincide with a center of the image.
(17)
The control apparatus according to any one of (1) to (16), in which the controller determines a combination of the slave parameter and the image parameter to be controlled, in accordance with an operation on the basis of an input to the master apparatus by a user.
(18)
The control apparatus according to (17), in which the controller determines a combination of the slave parameter and the image parameter to be controlled, in accordance with an operation on the basis of inputs to a plurality of the master apparatuses by a user.
(19)
The control apparatus according to any one of (1) to (18), in which
the detector detects whether or not a plurality of the master apparatus is located at the movable range limit, and
in a case where it is detected that at least one of the plurality of the master apparatuses is located at the movable range limit, the controller controls the slave parameter and the image parameter.
(20)
A control method including:
detecting whether or not a master apparatus used for an operation of a slave apparatus is located at a movable range limit, and
controlling, on the basis of a detection result, a slave parameter related to control of the slave apparatus and an image parameter related to an image displayed on the basis of imaging.
(21)
A master-slave system including:
a slave apparatus;
a master apparatus used for an operation of the slave apparatus; and
a control apparatus including a detector and a controller, the detector that detects whether or not the master apparatus is located at a movable range limit, and the controller that controls, on the basis of a detection result, a slave parameter related to control of the slave apparatus and an image parameter related to an image displayed on the basis of imaging.

REFERENCE SIGNS LIST

10: slave apparatus
20: master apparatus
30: imaging apparatus
32: imaging unit
40: display apparatus
50: control apparatus
110: front end section
112: contact section
210: operation body
220: force sensor
510: communication unit
520: detector
530: controller
531: magnification controller
533: offset controller
535: master-slave controller
537: imaging controller
539: display controller
1000: master-slave system

The invention claimed is:

1. A control apparatus comprising:
circuitry configured to
 detect whether or not a master apparatus used for an operation of a slave apparatus is located at a movable range limit; and
 control, on the basis of a detection result, a slave parameter related to control of the slave apparatus and an image parameter related to an image displayed on the basis of imaging, wherein
 the slave parameter includes an operation magnification indicating a ratio of a movement amount for the slave apparatus to a movement amount for the master apparatus,
 the image parameter includes an image magnification indicating a magnification related to the image, and
 the circuitry is further configured to control the operation magnification and the image magnification substantially simultaneously, and perform decrease control for decreasing the operation magnification and the image magnification under a condition that it is detected that the master apparatus is located at the movable range limit.

2. The control apparatus according to claim 1, wherein the circuitry is further configured to control the operation magnification and the image magnification to cause a change rate of the operation magnification and a change rate of the image magnification to be substantially the same as each other.

3. The control apparatus according to claim 1, wherein the circuitry is further configured to continuously perform the decrease control while it is detected that the master apparatus is located at the movable range limit.

4. The control apparatus according to claim 1, wherein the circuitry is further configured to perform the decrease control under a condition that it is detected that the master apparatus has reached one region of a boundary of a movable range of the master apparatus existing in a direction corresponding to a direction away from a contact target.

5. The control apparatus according to claim 1, wherein the circuitry is further configured to perform increase control for increasing the operation magnification and the image magnification in accordance with a predetermined increasing operation.

6. The control apparatus according to claim 5, wherein the circuitry is further configured to perform control of an offset corresponding to a position of the slave apparatus while performing the increase control.

7. The control apparatus according to claim 5, wherein the increasing operation includes an operation on the basis of an input to the master apparatus by a user.

8. The control apparatus according to claim 1, wherein
 a movable range of the master apparatus includes a first movable range and a second movable range, the first movable range being a region where the master apparatus is physically operable, and the second movable range being a region that is smaller than the first movable range and exists inside the first movable range, and
 under a condition that the master apparatus is located in a region between the first movable range and the second movable range, the circuitry is further configured to detect that the master apparatus is located at the movable range limit.

9. The control apparatus according to claim 8, wherein under a condition that it is detected that the master apparatus is located at the movable range limit, the circuitry is further configured to move the master apparatus into the second movable range.

10. The control apparatus according to claim 1, wherein the circuitry is further configured to perform control of the slave parameter and the image parameter to cause a center of an operation region of the slave apparatus corresponding to a movable range of the master apparatus to coincide with a center of the image.

11. The control apparatus according to claim 1, wherein the circuitry is further configured to determine a combination of the slave parameter and the image parameter to be controlled, in accordance with an operation on the basis of an input to the master apparatus by a user.

12. The control apparatus according to claim 11, wherein the circuitry is further configured to determine a combination of the slave parameter and the image parameter to be controlled, in accordance with an operation on the basis of inputs by the user to a plurality of master apparatuses including the master apparatus.

13. The control apparatus according to claim 1, wherein
 the circuitry is further configured to detect whether or not a plurality of master apparatuses, including the master apparatus, is located at the movable range limit, and
 under a condition that it is detected that at least one of the plurality of the master apparatuses is located at the movable range limit, the circuitry is further configured to control the slave parameter and the image parameter.

14. A control apparatus comprising: circuitry configured to
 detect whether or not a master apparatus used for an operation of a slave apparatus is located at a movable range limit; and
 control, on the basis of a detection result, a slave parameter related to control of the slave apparatus and an image parameter related to an image displayed on the basis of imaging, wherein
 the slave parameter includes an operation offset indicating an offset distance from a point in the slave apparatus corresponding to an origin point in the master apparatus to an origin point in the slave apparatus, the image parameter includes an image offset indicating an offset of the image, and the circuitry is further configured to control the operation offset and the image offset substantially simultaneously under a condition that it is detected that the master apparatus is located at the movable range limit.

15. The control apparatus according to claim 14, wherein the circuitry is further configured to control the operation offset and the image offset to cause a moving direction and a movement amount of a slave apparatus corresponding to a movable range of the master apparatus in actual space to be substantially the same as a moving direction and a movement amount of a display range on the image.

16. The control apparatus according to claim 14, wherein the circuitry is further configured to perform control of the operation offset and the image offset while it is detected that the master apparatus is located at the movable range limit.

17. A master-slave system comprising:

a slave apparatus;

a master apparatus used for an operation of the slave apparatus; and a control apparatus including circuitry configured to detect whether or not the master apparatus is located at a movable range limit, and control on the basis of a detection result, a slave parameter related to control of the slave apparatus and an image parameter related to an image displayed on the basis of imaging, wherein the slave parameter includes an operation magnification indicating a ratio of a movement amount for the slave apparatus to a movement amount for the master apparatus, the image parameter includes an image magnification indicating a magnification related to the image, and the circuitry is further configured to control the operation magnification and the image magnification substantially simultaneously, and perform decrease control for decreasing the operation magnification and the image magnification under a condition that it is detected that the master apparatus is located at the movable range limit.

* * * * *